(12) United States Patent
Bamberg et al.

(10) Patent No.: US 8,012,974 B2
(45) Date of Patent: Sep. 6, 2011

(54) PYRROLOPYRAZINYL UREA KINASE INHIBITORS

(75) Inventors: Joe Timothy Bamberg, East Palo Alto, CA (US); Johannes Cornelius Hermann, Jersey City, NJ (US); Remy Lemoine, San Francisco, CA (US); Michael Soth, Glen Rock, NJ (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 12/629,930

(22) Filed: Dec. 3, 2009

(65) Prior Publication Data

US 2010/0144745 A1    Jun. 10, 2010

Related U.S. Application Data

(60) Provisional application No. 61/201,008, filed on Dec. 5, 2008, provisional application No. 61/244,174, filed on Sep. 21, 2009.

(51) Int. Cl.
*A61K 31/495* (2006.01)

(52) U.S. Cl. ........ 514/249; 540/596; 544/350; 546/199; 546/276.7; 548/518; 549/356; 549/510

(58) Field of Classification Search .................. 514/249; 540/596; 544/350; 546/149, 276.7; 548/518; 549/356, 510
See application file for complete search history.

(56) References Cited

FOREIGN PATENT DOCUMENTS

| | | |
|---|---|---|
| WO | 2008/119792 | 10/2008 |
| WO | 2009/106443 | 9/2009 |

OTHER PUBLICATIONS

*Annu. Rev. Immunol.* 16 (1998) pp. 293-322.
Leonard et al., (2000), *J. Allergy Clin. Immnol.* 105:877-888.
*Oncogene* 19 (2000), pp. 5662-5679.
Demoulin et al., (1996), *Mol. Cell. Biol.* 16:4710-6.
Jurlander et al., (1997), *Blood* 89:4146-52.
Kaneko et al., (1997), *Clin Exp. Immun.* 109:185-193.
Nakamura et al., (1996), *J. Biol. Chem.* 271:19483-8.
Kudlacz et al., (2004) *Am. J. Transplant* 4:51-57.
Changelian (2003) *Science* 302:875-878.
Suzuki et al., (2000), *Blood* 96:2172-2180.
Malaviya et al., (1999), *Biochem. Biophys. Res. Commun.* 257:807-813.
Malaviya et al., (1999), *J. Biol. Chem.* 274:27028-27038.
Kirken, (2001), *Transpl. Proc.* 33:3268-3270.
Muller-Ladner et al., (2000), *J. Immunol.* 164:3894-3901.
Trieu et al., (2000), *Biochem Biophys. Res. Commun.* 267:22-25.
Sudbeck et al., (1999), *Clin. Cancer Res.* 5:1569-1582.
Nielsen et al., (1997), *Prac. Natl. Acad. Sci. USA* 94:6764-6769.
Yu et al., (1997), *J. Immunol.* 159:5206-5210.
Catlett-Falcone et al., (1999), *Immunity* 10:105-115.
*J. Immunol.* 168 (2002), pp. 2475-2482.
*Blood* 103 (2004), p. 2009-2018.
*J. Investig. Med.* 44 (1996), pp. 304-311.
*Curr. Opin. Cell Biol.* 9 (1997), pp. 233-239.
Knupp, G., *Chem. Ber.* 1984, 117(6), 2076-98.
*J. Med. Chem.* 2001, 44, 3764.

Primary Examiner — James O. Wilson
Assistant Examiner — Douglas M Willis
(74) Attorney, Agent, or Firm — George W. Johnston; Dennis P. Tramaloni; Jennifer L. Kisko

(57) ABSTRACT

The present invention relates to the use of novel pyrrolopyrazinyl urea derivatives of Formula I,

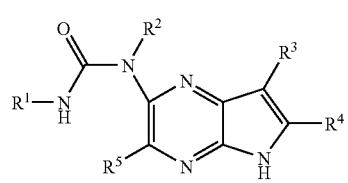

wherein the variables $R^1$, $R^2$, $R^3$, $R^4$, and $R^5$ are defined as described herein, which inhibit JAK and are useful for the treatment of auto-immune and inflammatory diseases.

31 Claims, No Drawings

PYRROLOPYRAZINYL UREA KINASE INHIBITORS

CROSS-REFERENCE TO RELATED APPLICATIONS

This application is entitled to the benefit of U.S. provisional patent application Ser. No. 61/201,008 filed on Dec. 5, 2008 and U.S. provisional patent application Ser. No. 61/244,174 filed on Sep. 21, 2009, the disclosures of which are hereby incorporated by reference in their entirety.

FIELD OF THE INVENTION

The present invention relates to the use of novel pyrrolopyrazinyl urea derivatives which are JAK inhibitors and selectively inhibit JAK3 and are useful for the treatment of autoimmune and inflammatory diseases.

BACKGROUND OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

The JAKs (JAnus Kinases) are a family of cytoplasmic protein tyrosine kinases including JAK1, JAK2, JAK3 and TYK2. Each of the JAKs is preferentially associated with the intracytoplasmic portion of discrete cytokine receptors (*Annu. Rev. Immunol.* 16 (1998), pp. 293-322). The JAKs are activated following ligand binding and initiate signaling by phosphorylating cytokine receptors that, per se, are devoid of intrinsic kinase activity. This phosphorylation creates docking sites on the receptors for other molecules known as STAT proteins (signal transducers and activators of transcription) and the phosphorylated JAKs bind various STAT proteins. STAT proteins, or STATs, are DNA binding proteins activated by phosphorylation of tyrosine residues, and function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Thus, the JAKs and STATs are components of multiple potentially intertwined signal-transduction pathways (*Oncogene* 19 (2000), pp. 5662-5679), which indicates the difficulty of specifically targeting one element of the JAK-STAT pathway without interfering with other signal transduction pathways.

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit for inhibition of JAK3 are discussed in greater detail below.

However, in contrast to the relatively ubiquitous expression of JAK1, JAK2 and Tyk2, JAK3 has a more restricted and regulated expression. Whereas some JAKs (JAK1, JAK2, Tyk2) are used by a variety of cytokine receptors, JAK3 is used only by cytokines that contain a γc in their receptor. JAK3, therefore, plays a role in cytokine signaling for cytokines which receptor was shown to date to use the common gamma chain; IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-alpha. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

In particular, JAK3 has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res.

Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10:105-115).

JAK3 inhibitors are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Non-hematopoietic expression of JAK3 has also been reported, although the functional significance of this has yet to be clarified (*J. Immunol.* 168 (2002), pp. 2475-2482). Because bone marrow transplants for SCID are curative (*Blood* 103 (2004), pp. 2009-2018), it seems unlikely that JAK3 has essential non-redundant functions in other tissues or organs. Hence, in contrast with other targets of immuno-suppressive drugs, the restricted distribution of JAK3 is appealing. Agents that act on molecular targets with expression limited to the immune system might lead to an optimal efficacy:toxicity ratio. Targeting JAK3 would, therefore, theoretically offer immune suppression where it is needed (i.e. on cells actively participating in immune responses) without resulting in any effects outside of these cell populations. Although defective immune responses have been described in various STAT$^{-/-}$ (*J. Investig. Med.* 44 (1996), pp. 304-311; *Curr. Opin. Cell Biol.* 9 (1997), pp. 233-239), the ubiquitous distribution of STATs and the fact that those molecules lack enzymatic activity that could be targeted with small-molecule inhibitors has contributed to their non-selection as key targets for immunosuppression.

In view of the numerous conditions that are contemplated to benefit by treatment involving modulation of the JAK pathways it is immediately apparent that new compounds that modulate JAK pathways and methods of using these compounds should provide substantial therapeutic benefits to a wide variety of patients. Provided herein are novel pyrrolopyrazinyl urea derivatives for use in the treatment of conditions in which targeting of the JAK pathways or inhibition of JAK kinases, particularly JAK3, and are therapeutically useful for the treatment of auto-immune and inflammatory diseases.

SUMMARY OF THE INVENTION

The novel pyrrolopyrazinyl urea derivatives provided herein selectively inhibit JAK3 and are useful for the treatment of auto-immune and inflammatory diseases. The compounds of the invention modulate the JAK pathways and are useful novel pyrrolopyrazinyl urea derivatives for the treatment of auto-immune and inflammatory diseases, wherein preferred compounds selectively inhibit JAK3. For example, the compounds of the invention may inhibit JAK3, wherein preferred compounds are selective for JAK3 of the JAK kinases and are useful novel pyrrolopyrazinyl urea derivatives for the treatment of auto-immune and inflammatory diseases. Furthermore, the compounds of the invention may inhibit JAK3 and JAK2, wherein preferred compounds are selective for JAK3 of the JAK kinases, and are useful novel pyrrolopyrazinyl urea derivatives for the treatment of auto-immune and inflammatory diseases. Similarly, the compounds of the invention may inhibit JAK3 and JAK1, wherein preferred compounds are selective for JAK3 of the JAK kinases, and are useful novel pyrrolopyrazinyl urea derivatives for the treatment of auto-immune and inflammatory diseases.

The application provides a compound of Formula I

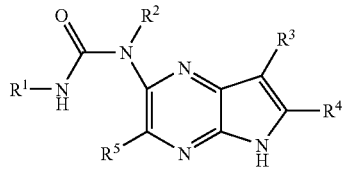

wherein:
$R^1$ is lower alkyl, cycloalkyl, cycloalkyl lower alkyl, phenyl, phenyl lower alkyl, heterocycloalkyl, heterocycloalkyl lower alkyl, heteroaryl, heteroaryl lower alkyl, or spirocycloalkyl, each optionally substituted with one or more $R^{1'}$;
$R^{1'}$ is halogen, lower alkyl, hydroxy, lower hydroxyalkyl, lower alkoxy, lower haloalkyl, amino, —C(=O)N($R^{1a}$)$_2$, —C(=O)O($R^{1a}$), —C(=O)($R^{1a}$), —S(=O)$_2$($R^{1a}$), oxo, cyano, sulfonamido, cycloalkyl, or spirocycloalkyl;
  each $R^{1a}$ is H or $R^{1b}$;
  $R^{1b}$ is lower alkyl, lower haloalkyl, lower alkoxy, lower alkylene, hydroxy lower alkyl, cyano lower alkyl, cycloalkyl, cycloalkyl lower alkyl, spirocycloalkyl, spirocycloalkyl lower alkyl, heterocycloalkyl, heterocycloalkyl lower alkyl, spiroheterocycloalkyl, or spiroheterocycloalkyl lower alkyl, each optionally substituted with one or more $R^{1b'}$;
    $R^{1b'}$ is halogen, hydroxy, lower alkyl, lower alkoxy, lower haloalkyl, or hydroxy lower alkyl;
$R^2$ is H or lower alkyl; and
$R^3$, $R^4$, and $R^5$ are independently selected from the group consisting of H, lower alkyl, halogen, hydroxy, lower hydroxyalkyl, lower alkoxy, and lower haloalkyl;
or a pharmaceutically acceptable salt thereof.

In one variation of Formula I, $R^2$ is H.
In one variation of Formula I, $R^3$ is H.
In one variation of Formula I, $R^2$ is H and $R^3$ is H.
In one variation of Formula I, $R^4$ is H.
In one variation of Formula I, $R^4$ is H, $R^2$ is H and $R^3$ is H.
In one variation of Formula I, $R^5$ is H.
In one variation of Formula I, $R^5$ is H, $R^4$ is H, $R^2$ is H and $R^3$ is H.
In one variation of Formula I, $R^1$ is cycloalkyl.
In one variation of Formula I, $R^1$ is cycloalkyl, $R^5$ is H, $R^4$ is H, $R^2$ is H and $R^3$ is H.
In one variation of Formula I, $R^1$ is cyclohexyl.
In one variation of Formula I, $R^1$ is cyclohexyl, $R^5$ is H, $R^4$ is H, $R^2$ is H and $R^3$ is H.
In one variation of Formula I, $R^{1'}$ is lower alkyl.
In one variation of Formula I, $R^{1'}$ is methyl.
In one variation of Formula I, $R^{1'}$ is lower alkyl, $R^1$ is cyclohexyl, $R^5$ is H, $R^4$ is H, $R^2$ is H and $R^3$ is H.
In one variation of Formula I, $R^{1'}$ is methyl, $R^1$ is cyclohexyl, $R^5$ is H, $R^4$ is H, $R^2$ is H and $R^3$ is H.
In one variation of Formula I, $R^2$ is H and $R^1$ is cycloalkyl.
In one variation of Formula I, $R^2$ is H, $R^3$ is H, and $R^1$ is cycloalkyl.
In one variation of Formula I, $R^4$ is H, $R^2$ is H, $R^3$ is H, and $R^1$ is cycloalkyl.
In one variation of Formula I, $R^5$ is H, $R^4$ is H, $R^2$ is H, $R^3$ is H, and $R^1$ is cycloalkyl.
In one variation of Formula I, $R^1$ is cycloalkyl lower alkyl.
In one variation of Formula I, $R^1$ is phenyl lower alkyl.
In one variation of Formula I, $R^1$ is phenylethyl.

In one variation of Formula I, $R^5$ is H, $R^4$ is H, $R^2$ is H, $R^3$ is H, and $R^1$ is cycloalkyl lower alkyl.

In one variation of Formula I, $R^5$ is H, $R^4$ is H, $R^2$ is H, $R^3$ is H, and $R^1$ is phenyl lower alkyl.

In one variation of Formula I, $R^5$ is H, $R^4$ is H, $R^2$ is H, $R^3$ is H, and $R^1$ is phenylethyl.

The application provides a compound of Formula I

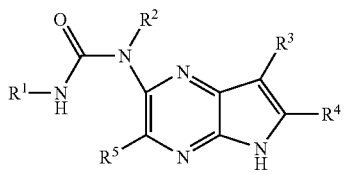

wherein:

$R^1$ is cycloalkyl, cycloalkyl lower alkyl, heterocycloalkyl, or heterocycloalkyl lower alkyl, each optionally substituted with one or more $R^{1'}$;

$R^{1'}$ is halogen, lower alkyl, hydroxy, lower hydroxyalkyl, lower alkoxy, lower haloalkyl, amino, —C(=O)N($R^{1a}$)$_2$, —C(=O)O($R^{1a}$), —C(=O)($R^{1a}$), —S(=O)$_2$($R^{1a}$), oxo, cyano, sulfonamido, cycloalkyl, or spirocycloalkyl;

each $R^{1a}$ is H or $R^{1b}$;

$R^{1b}$ is lower alkyl, lower haloalkyl, lower alkoxy, lower alkylene, hydroxy lower alkyl, cyano lower alkyl, cycloalkyl, cycloalkyl lower alkyl, spirocycloalkyl, spirocycloalkyl lower alkyl, heterocycloalkyl, heterocycloalkyl lower alkyl, spiroheterocycloalkyl, or spiroheterocycloalkyl lower alkyl, each optionally substituted with one or more $R^{1b'}$;

$R^{1b'}$ is halogen, hydroxy, lower alkyl, lower alkoxy, lower haloalkyl, or hydroxy lower alkyl;

$R^2$ is H or lower alkyl; and each of $R^3$, $R^4$, and $R^5$ are independently selected from the group consisting of H, lower alkyl, halogen, hydroxy, lower hydroxyalkyl, lower alkoxy, and lower haloalkyl;

or a pharmaceutically acceptable salt thereof.

In one variation of Formula I, $R^2$ is H, $R^3$ is H, $R^4$ is H, and $R^5$ is H.

In one variation of Formula I, $R^1$ is heterocycloalkyl.

In one variation of Formula I, $R^1$ is heterocycloalkyl, $R^2$ is H, $R^3$ is H, $R^4$ is H, and $R^5$ is H.

In one variation of Formula I, $R^1$ is piperidine.

In one variation of Formula I, $R^1$ is piperidine, $R^2$ is H, $R^3$ is H, $R^4$ is H, and $R^5$ is H.

In one variation of Formula I, $R^{1'}$ is —S(=O)$_2$($R^{1a}$).

In one variation of Formula I, $R^{1'}$ is —S(=O)$_2$($R^{1a}$), $R^2$ is H, $R^3$ is H, $R^4$ is H, and $R^5$ is H.

In one variation of Formula I, $R^{1a}$ is lower alkyl.

In one variation of Formula I, $R^{1a}$ is lower alkyl, $R^2$ is H, $R^3$ is H, $R^4$ is H, and $R^5$ is H.

In one variation of Formula I, $R^1$ is pyrrolidine and $R^{1'}$ is —S(=O)$_2$($R^{1a}$).

In one variation of Formula I, $R^1$ is pyrrolidine and $R^{1'}$ is —S(=O)$_2$($R^{1a}$), $R^2$ is H, $R^3$ is H, $R^4$ is H, and $R^5$ is H.

In one variation of Formula I, $R^1$ is heterocycloalkyl lower alkyl.

In one variation of Formula I, $R^1$ is heterocycloalkyl lower alkyl, $R^2$ is H, $R^3$ is H, $R^4$ is H, and $R^5$ is H.

In one variation of Formula I, $R^1$ is pyrrolidinyl methylene and $R^{1'}$ is —S(=O)$_2$($R^{1a}$).

In one variation of Formula I, $R^1$ is pyrrolidinyl methylene and $R^{1'}$ is —S(=O)$_2$($R^{1a}$), $R^2$ is H, $R^3$ is H, $R^4$ is H, and $R^5$ is H.

The application provides a compound selected from the group consisting of:

1-Cyclohexyl-3-(5H-pyrrolo[2,3-b]pyrazin-2-yl)-urea;
1-Phenyl-3-(5H-pyrrolo[2,3-b]pyrazin-2-yl)-urea;
1-Cyclopentyl-3-(5H-pyrrolo[2,3-b]pyrazin-2-yl)-urea;
1-Cycloheptyl-3-(5H-pyrrolo[2,3-b]pyrazin-2-yl)-urea;
1-Benzyl-3-(5H-pyrrolo[2,3-b]pyrazin-2-yl)-urea;
1-Cyclohexylmethyl-3-(5H-pyrrolo[2,3-b]pyrazin-2-yl)-urea;
1-((1S,2R)-2-Methyl-cyclohexyl)-3-(5H-pyrrolo[2,3-b]pyrazin-2-yl)-urea;
1-(2-Chloro-phenyl)-3-(5H-pyrrolo[2,3-b]pyrazin-2-yl)-urea;
1-((R)-1-Phenyl-ethyl)-3-(5H-pyrrolo[2,3-b]pyrazin-2-yl)-urea;
1-Phenethyl-3-(5H-pyrrolo[2,3-b]pyrazin-2-yl)-urea;
1-((S)-1-Phenyl-ethyl)-3-(5H-pyrrolo[2,3-b]pyrazin-2-yl)-urea;
1-(5H-Pyrrolo[2,3-b]pyrazin-2-yl)-3-o-tolyl-urea;
1-(5H-Pyrrolo[2,3-b]pyrazin-2-yl)-3-(2-trifluoromethyl-phenyl)-urea;
1-Ethyl-3-(5H-pyrrolo[2,3-b]pyrazin-2-yl)-urea;
1-tert-Butyl-3-(5H-pyrrolo[2,3-b]pyrazin-2-yl)-urea;
1-Isopropyl-3-(5H-pyrrolo[2,3-b]pyrazin-2-yl)-urea;
[3-(5H-Pyrrolo[2,3-b]pyrazin-2-yl)-ureido]-acetic acid ethyl ester;
N-Methyl-2-[3-(5H-pyrrolo[2,3-b]pyrazin-2-yl)-ureido]-acetamide;
(S)-3-Methyl-2-[3-(5H-pyrrolo[2,3-b]pyrazin-2-yl)-ureido]-butyric acid methyl ester;
(S)-3,N-Dimethyl-2-[3-(5H-pyrrolo[2,3-b]pyrazin-2-yl)-ureido]-butyramide;
1-((3S,4S)-3-Methyl-tetrahydro-pyran-4-yl)-3-(5H-pyrrolo[2,3-b]pyrazin-2-yl)-urea;
1-(5H-Pyrrolo[2,3-b]pyrazin-2-yl)-3-((1S,2R)-2,5,5-trimethyl-cyclohexyl)-urea;
1-(1-Acetyl-piperidin-3-yl)-3-(5H-pyrrolo[2,3-b]pyrazin-2-yl)-urea;
1-(3,3-Dimethyl-cyclohexyl)-3-(5H-pyrrolo[2,3-b]pyrazin-2-yl)-urea;
1-(3-Methyl-cyclohexyl)-3-(5H-pyrrolo[2,3-b]pyrazin-2-yl)-urea;
1-((1R,2S)-2-Methyl-cyclohexyl)-3-(5H-pyrrolo[2,3-b]pyrazin-2-yl)-urea;
1-(5H-Pyrrolo[2,3-b]pyrazin-2-yl)-3-spiro[2.5]oct-5-yl-urea;
3-Cyclohexyl-1-methyl-1-(5H-pyrrolo[2,3-b]pyrazin-2-yl)-urea;
1-[1-(2-Cyano-acetyl)-piperidin-3-yl]-3-(5H-pyrrolo[2,3-b]pyrazin-2-yl)-urea;
1-(2,2-Dimethyl-cyclopentyl)-3-(5H-pyrrolo[2,3-b]pyrazin-2-yl)-urea;
1-(5H-Pyrrolo[2,3-b]pyrazin-2-yl)-3-[1-(2,2,2-trifluoro-ethyl)-piperidin-3-yl]-urea;
1-(1-Methanesulfonyl-piperidin-3-yl)-3-(5H-pyrrolo[2,3-b]pyrazin-2-yl)-urea;
3-[3-(5H-Pyrrolo[2,3-b]pyrazin-2-yl)-ureido]-piperidine-1-carboxylic acid methyl ester;
1-((S)-1-Acetyl-piperidin-3-yl)-3-(5H-pyrrolo[2,3-b]pyrazin-2-yl)-urea;
1-((1R,3R)-3-Amino-cyclopentyl)-3-(5H-pyrrolo[2,3-b]pyrazin-2-yl)-urea;
1-(5H-Pyrrolo[2,3-b]pyrazin-2-yl)-3-[1-(3,3,3-trifluoro-propionyl)-piperidin-3-yl]-urea;

1-((R)-1-Acetyl-piperidin-3-yl)-3-(5H-pyrrolo[2,3-b]pyrazin-2-yl)-urea;
3-[3-(5H-Pyrrolo[2,3-b]pyrazin-2-yl)-ureido]-piperidine-1-carboxylic acid ethyl Ester;
1-(1-Propionyl-piperidin-3-yl)-3-(5H-pyrrolo[2,3-b]pyrazin-2-yl)-urea;
1-(1-Isobutyryl-piperidin-3-yl)-3-(5H-pyrrolo[2,3-b]pyrazin-2-yl)-urea;
1-[1-(3-Methyl-butyryl)-piperidin-3-yl]-3-(5H-pyrrolo[2,3-b]pyrazin-2-yl)-urea;
1-Cyclohexyl-3-(6-methyl-5H-pyrrolo[2,3-b]pyrazin-2-yl)-urea;
1-Cyclohexyl-3-(7-methyl-5H-pyrrolo[2,3-b]pyrazin-2-yl)-urea;
1-(1-Ethanesulfonyl-piperidin-3-yl)-3-(5H-pyrrolo[2,3-b]pyrazin-2-yl)-urea;
1-[1-(Propane-2-sulfonyl)-piperidin-3-yl]-3-(5H-pyrrolo[2,3-b]pyrazin-2-yl)-urea;
1-((S)-1-Acetyl-pyrrolidin-3-yl)-3-(5H-pyrrolo[2,3-b]pyrazin-2-yl)-urea;
1-((S)-1-Methanesulfonyl-pyrrolidin-3-yl)-3-(5H-pyrrolo[2,3-b]pyrazin-2-yl)-urea;
(S)-3-[3-(5H-Pyrrolo[2,3-b]pyrazin-2-yl)-ureido]-pyrrolidine-1-carboxylic acid methyl ester;
1-((3S,5S)-1-Acetyl-5-methyl-piperidin-3-yl)-3-(5H-pyrrolo[2,3-b]pyrazin-2-yl)-urea;
1-(1-Cyclopropanesulfonyl-piperidin-3-yl)-3-(5H-pyrrolo[2,3-b]pyrazin-2-yl)-urea;
1-[1-(Propane-1-sulfonyl)-piperidin-3-yl]-3-(5H-pyrrolo[2,3-b]pyrazin-2-yl)-urea;
1-((5R,6S)-6-Methyl-spiro[2.5]oct-5-yl)-3-(5H-pyrrolo[2,3-b]pyrazin-2-yl)-urea;
1-((5S,6R)-6-Methyl-spiro[2.5]oct-5-yl)-3-(5H-pyrrolo[2,3-b]pyrazin-2-yl)-urea;
1-Pyridin-2-ylmethyl-3-(5H-pyrrolo[2,3-b]pyrazin-2-yl)-urea;
1-Pyridin-3-ylmethyl-3-(5H-pyrrolo[2,3-b]pyrazin-2-yl)-urea;
1-(2-Pyridin-2-yl-ethyl)-3-(5H-pyrrolo[2,3-b]pyrazin-2-yl)-urea;
1-(2-Pyridin-3-yl-ethyl)-3-(5H-pyrrolo[2,3-b]pyrazin-2-yl)-urea;
1-(2-Isopropyl-cyclohexyl)-3-(5H-pyrrolo[2,3-b]pyrazin-2-yl)-urea;
1-((1S,2R)-2-Methyl-cycloheptyl)-3-(5H-pyrrolo[2,3-b]pyrazin-2-yl)-urea;
1-((1R,2R)-2-Methyl-cyclohexyl)-3-(5H-pyrrolo[2,3-b]pyrazin-2-yl)-urea;
1-((1S,2S)-2-Methyl-cyclohexyl)-3-(5H-pyrrolo[2,3-b]pyrazin-2-yl)-urea;
(R)-3-[3-(5H-Pyrrolo[2,3-b]pyrazin-2-yl)-ureido]-pyrrolidine-1-carboxylic acid methyl ester;
1-((R)-1-Methanesulfonyl-pyrrolidin-3-yl)-3-(5H-pyrrolo[2,3-b]pyrazin-2-yl)-urea;
1-((R)-1-Acetyl-pyrrolidin-3-yl)-3-(5H-pyrrolo[2,3-b]pyrazin-2-yl)-urea;
1-(1-Cyclopropanecarbonyl-piperidin-3-yl)-3-(5H-pyrrolo[2,3-b]pyrazin-2-yl)-urea;
1-(5H-Pyrrolo[2,3-b]pyrazin-2-yl)-3-(1-trifluoromethanesulfonyl-piperidin-3-yl)-urea;
1-(5H-Pyrrolo[2,3-b]pyrazin-2-yl)-3-[1-(2,2,2-trifluoroethanesulfonyl)-piperidin-3-yl]-urea;
1-(2-Ethyl-cyclohexyl)-3-(5H-pyrrolo[2,3-b]pyrazin-2-yl)-urea;
1-(1-Acetyl-3-methyl-piperidin-4-yl)-3-(5H-pyrrolo[2,3-b]pyrazin-2-yl)-urea;
1-(1-Methanesulfonyl-3-methyl-piperidin-4-yl)-3-(5H-pyrrolo[2,3-b]pyrazin-2-yl)-urea;
3-Methyl-4-[3-(5H-pyrrolo[2,3-b]pyrazin-2-yl)-ureido]-piperidine-1-carboxylic acid methyl ester;
1-(1-Methanesulfonyl-pyrrolidin-2-ylmethyl)-3-(5H-pyrrolo[2,3-b]pyrazin-2-yl)-urea;
1-[1-(2-Cyclopropyl-acetyl)-piperidin-3-yl]-3-(5H-pyrrolo[2,3-b]pyrazin-2-yl)-urea;
1-(1-Methanesulfonyl-azepan-3-yl)-3-(5H-pyrrolo[2,3-b]pyrazin-2-yl)-urea;
3-[3-(5H-Pyrrolo[2,3-b]pyrazin-2-yl)-ureido]-azepane-1-carboxylic acid methyl ester;
1-(1-Acetyl-azepan-3-yl)-3-(5H-pyrrolo[2,3-b]pyrazin-2-yl)-urea;
1-[1-(2-Methyl-propane-1-sulfonyl)-piperidin-3-yl]-3-(5H-pyrrolo[2,3-b]pyrazin-2-yl)-urea;
1-(1-Methanesulfonyl-piperidin-4-yl)-3-(5H-pyrrolo[2,3-b]pyrazin-2-yl)-urea;
1-(1-Acetyl-piperidin-4-yl)-3-(5H-pyrrolo[2,3-b]pyrazin-2-yl)-urea;
1-[1-(Butane-2-sulfonyl)-piperidin-3-yl]-3-(5H-pyrrolo[2,3-b]pyrazin-2-yl)-urea;
1-((R)-1-Methanesulfonyl-piperidin-3-yl)-3-(5H-pyrrolo[2,3-b]pyrazin-2-yl)-urea;
1-[(R)-1-(Propane-1-sulfonyl)-piperidin-3-yl]-3-(5H-pyrrolo[2,3-b]pyrazin-2-yl)-urea;
4-[3-(5H-Pyrrolo[2,3-b]pyrazin-2-yl)-ureido]-piperidine-1-carboxylic acid methyl ester;
1-(1R,2R,4S)-Bicyclo[2.2.1]hept-2-yl-3-(5H-pyrrolo[2,3-b]pyrazin-2-yl)-urea;
1-(1R,2S,4S)-Bicyclo[2.2.1]hept-2-yl-3-(5H-pyrrolo[2,3-b]pyrazin-2-yl)-urea;
1-(1-Methyl-cyclohexyl)-3-(5H-pyrrolo[2,3-b]pyrazin-2-yl)-urea;
1-(1-Cyclopropylmethanesulfonyl-piperidin-3-yl)-3-(5H-pyrrolo[2,3-b]pyrazin-2-yl)-urea;
1-((1S,3S)-3-Hydroxymethyl-cyclohexyl)-3-(5H-pyrrolo[2,3-b]pyrazin-2-yl)-urea;
1-[(R)-1-(2-Methyl-propane-1-sulfonyl)-piperidin-3-yl]-3-(5H-pyrrolo[2,3-b]pyrazin-2-yl)-urea;
1-((S)-1-Methanesulfonyl-piperidin-3-yl)-3-(5H-pyrrolo[2,3-b]pyrazin-2-yl)-urea;
1-[(S)-1-(Propane-1-sulfonyl)-piperidin-3-yl]-3-(5H-pyrrolo[2,3-b]pyrazin-2-yl)-urea;
1-[(S)-1-(2-Methyl-propane-1-sulfonyl)-piperidin-3-yl]-3-(5H-pyrrolo[2,3-b]pyrazin-2-yl)-urea;
1-(7-Chloro-5H-pyrrolo[2,3-b]pyrazin-2-yl)-3-cyclohexyl-urea;
1-[(S)-1-(Propane-1-sulfonyl)-pyrrolidin-3-yl]-3-(5H-pyrrolo[2,3-b]pyrazin-2-yl)-urea;
1-[(S)-1-(2-Methyl-propane-1-sulfonyl)-pyrrolidin-3-yl]-3-(5H-pyrrolo[2,3-b]pyrazin-2-yl)-urea;
1-[1-(Propane-1-sulfonyl)-azepan-3-yl]-3-(5H-pyrrolo[2,3-b]pyrazin-2-yl)-urea;
1-[1-(2-Methyl-propane-1-sulfonyl)-azepan-3-yl]-3-(5H-pyrrolo[2,3-b]pyrazin-2-yl)-urea;
1-[(3S,5S)-5-Methyl-1-(propane-1-sulfonyl)-piperidin-3-yl]-3-(5H-pyrrolo[2,3-b]pyrazin-2-yl)-urea;
1-[(3S,5S)-5-Methyl-1-(2-methyl-propane-1-sulfonyl)-piperidin-3-yl]-3-(5H-pyrrolo[2,3-b]pyrazin-2-yl)-urea;
1-((R)-1-Ethanesulfonyl-pyrrolidin-3-yl)-3-(5H-pyrrolo[2,3-b]pyrazin-2-yl)-urea;
1-[(R)-1-(Propane-2-sulfonyl)-pyrrolidin-3-yl]-3-(5H-pyrrolo[2,3-b]pyrazin-2-yl)-urea;
1-[(R)-1-(Propane-1-sulfonyl)-pyrrolidin-3-yl]-3-(5H-pyrrolo[2,3-b]pyrazin-2-yl)-urea;

1-[(R)-1-(2-Methyl-propane-1-sulfonyl)-pyrrolidin-3-yl]-3-(5H-pyrrolo[2,3-b]pyrazin-2-yl)-urea;
1-(5H-Pyrrolo[2,3-b]pyrazin-2-yl)-3-((R)-1-trifluoromethanesulfonyl-pyrrolidin-3-yl)-urea;
1-(1-Methanesulfonyl-piperidin-2-ylmethyl)-3-(5H-pyrrolo[2,3-b]pyrazin-2-yl)-urea;
1-[2-(1-Methanesulfonyl-pyrrolidin-2-yl)-ethyl]-3-(5H-pyrrolo[2,3-b]pyrazin-2-yl)-urea;
2-{2-[3-(5H-Pyrrolo[2,3-b]pyrazin-2-yl)-ureido]-ethyl}-pyrrolidine-1-carboxylic acid methyl ester;
4-[3-(5H-Pyrrolo[2,3-b]pyrazin-2-yl)-ureido]-azepane-1-carboxylic acid methyl ester;
1-(1-Methanesulfonyl-azepan-4-yl)-3-(5H-pyrrolo[2,3-b]pyrazin-2-yl)-urea;
1-[2-(1-Methanesulfonyl-piperidin-3-yl)-ethyl]-3-(5H-pyrrolo[2,3-b]pyrazin-2-yl)-urea;
3-{2-[3-(5H-Pyrrolo[2,3-b]pyrazin-2-yl)-ureido]-ethyl}-piperidine-1-carboxylic acid methyl ester;
1-(1-Acetyl-azepan-4-yl)-3-(5H-pyrrolo[2,3-b]pyrazin-2-yl)-urea;
1-[1-(3-Methyl-butane-1-sulfonyl)-piperidin-3-yl]-3-(5H-pyrrolo[2,3-b]pyrazin-2-yl)-urea;
1-(5H-Pyrrolo[2,3-b]pyrazin-2-yl)-3-[1-(3,3,3-trifluoro-propane-1-sulfonyl)-piperidin-3-yl]-urea;
1-(5H-Pyrrolo[2,3-b]pyrazin-2-yl)-3-[(R)-1-(3,3,3-trifluoro-propane-1-sulfonyl)-pyrrolidin-3-yl]-urea;
1-((3R,5R)-1-Acetyl-5-methyl-piperidin-3-yl)-3-(5H-pyrrolo[2,3-b]pyrazin-2-yl)-urea;
1-[(S)-1-(2,2-Dimethyl-propane-1-sulfonyl)-piperidin-3-yl]-3-(5H-pyrrolo[2,3-b]pyrazin-2-yl)-urea;
1-[(S)-1-(2-Methoxy-ethanesulfonyl)-piperidin-3-yl]-3-(5H-pyrrolo[2,3-b]pyrazin-2-yl)-urea;
1-(1-Methanesulfonyl-5-methyl-azepan-4-yl)-3-(5H-pyrrolo[2,3-b]pyrazin-2-yl)-urea;
4-Methyl-5-[3-(5H-pyrrolo[2,3-b]pyrazin-2-yl)-ureido]-azepane-1-carboxylic acid methyl ester;
1-(1-Acetyl-piperidin-2-ylmethyl)-3-(5H-pyrrolo[2,3-b]pyrazin-2-yl)-urea;
2-{[3-(5H-Pyrrolo[2,3-b]pyrazin-2-yl)-ureido-methyl}-piperidine-1-carboxylic acid methyl ester;
1-[2-(1-Acetyl-piperidin-2-yl)-ethyl]-3-(5H-pyrrolo[2,3-b]pyrazin-2-yl)-urea;
2-{2-[3-(5H-Pyrrolo[2,3-b]pyrazin-2-yl)-ureido]-ethyl}-piperidine-1-carboxylic acid methyl ester;
1-(1-Acetyl-piperidin-4-ylmethyl)-3-(5H-pyrrolo[2,3-b]pyrazin-2-yl)-urea;
1-(1-Methanesulfonyl-piperidin-4-ylmethyl)-3-(5H-pyrrolo[2,3-b]pyrazin-2-yl)-urea;
1-((1S,3S)-3-Methoxymethyl-cyclohexyl)-3-(5H-pyrrolo[2,3-b]pyrazin-2-yl)-urea;
1-(1-Acetyl-5-methyl-azepan-4-yl)-3-(5H-pyrrolo[2,3-b]pyrazin-2-yl)-urea;
1-[2-(1-Methanesulfonyl-piperidin-2-yl)-ethyl]-3-(5H-pyrrolo[2,3-b]pyrazin-2-yl)-urea;
1-[2-(1-Acetyl-piperidin-3-yl)-ethyl]-3-(5H-pyrrolo[2,3-b]pyrazin-2-yl)-urea;
4-{[3-(5H-Pyrrolo[2,3-b]pyrazin-2-yl)-ureido]-methyl}-piperidine-1-carboxylic acid methyl ester;
2-{[3-(5H-Pyrrolo[2,3-b]pyrazin-2-yl)-ureido]-methyl}-pyrrolidine-1-carboxylic acid methyl ester;
1-(5H-Pyrrolo[2,3-b]pyrazin-2-yl)-3-[(S)-1-(1-trifluoromethyl-cyclopropylmethanesulfonyl)-piperidin-3-yl]-urea;
1-Cyclohexyl-3-(7-isopropyl-5H-pyrrolo[2,3-b]pyrazin-2-yl)-urea;
1-[(S)-1-(3-Methyl-oxetan-3-ylmethanesulfonyl)-piperidin-3-yl]-3-(5H-pyrrolo[2,3-b]pyrazin-2-yl)-urea;
1-(1-Acetyl-piperidin-3-ylmethyl)-3-(5H-pyrrolo[2,3-b]pyrazin-2-yl)-urea;
1-(1-Methanesulfonyl-piperidin-3-ylmethyl)-3-(5H-pyrrolo[2,3-b]pyrazin-2-yl)-urea;
1-[2-(1-Acetyl-piperidin-4-yl)-ethyl]-3-(5H-pyrrolo[2,3-b]pyrazin-2-yl)-urea;
1-[2-(1-Acetyl-pyrrolidin-2-yl)-ethyl]-3-(5H-pyrrolo[2,3-b]pyrazin-2-yl)-urea;
1-[1-(Propane-1-sulfonyl)-pyrrolidin-2-ylmethyl]-3-(5H-pyrrolo[2,3-b]pyrazin-2-yl)-urea;
1-[2-(1-Methanesulfonyl-piperidin-4-yl)-ethyl]-3-(5H-pyrrolo[2,3-b]pyrazin-2-yl)-urea;
4-{2-[3-(5H-Pyrrolo[2,3-b]pyrazin-2-yl)-ureido]-ethyl}-piperidine-1-carboxylic acid methyl ester;
1-(1-Ethanesulfonyl-pyrrolidin-2-ylmethyl)-3-(5H-pyrrolo[2,3-b]pyrazin-2-yl)-urea;
1-[1-(Propane-2-sulfonyl)-pyrrolidin-2-ylmethyl]-3-(5H-pyrrolo[2,3-b]pyrazin-2-yl)-urea;
3-{[3-(5H-Pyrrolo[2,3-b]pyrazin-2-yl)-ureido]-methyl}-piperidine-1-carboxylic acid methyl ester;
1-(1-Methanesulfonyl-pyrrolidin-3-ylmethyl)-3-(5H-pyrrolo[2,3-b]pyrazin-2-yl)-urea;
1-(1-Acetyl-pyrrolidin-2-ylmethyl)-3-(5H-pyrrolo[2,3-b]pyrazin-2-yl)-urea;
1-[1-(2-Methyl-propane-1-sulfonyl)-pyrrolidin-2-ylmethyl]-3-(5H-pyrrolo[2,3-b]pyrazin-2-yl)-urea;
1-(5H-Pyrrolo[2,3-b]pyrazin-2-yl)-3-[1-(2,2,2-trifluoro-ethyl)-piperidin-2-ylmethyl]-urea;
1-(5H-Pyrrolo[2,3-b]pyrazin-2-yl)-3-[1-(2,2,2-trifluoro-ethyl)-piperidin-4-ylmethyl]-urea;
(1S,3S)-3-[3-(5H-Pyrrolo[2,3-b]pyrazin-2-yl)-ureido]-cyclohexanecarboxylic acid dimethylamide;
1-(5H-Pyrrolo[2,3-b]pyrazin-2-yl)-3-[1-(2,2,2-trifluoro-ethyl)-piperidin-3-ylmethyl]-urea;
1-(5H-Pyrrolo[2,3-b]pyrazin-2-yl)-3-{2-[1-(2,2,2-trifluoro-ethyl)-piperidin-3-yl]-ethyl}-urea;
3-{[3-(5H-Pyrrolo[2,3-b]pyrazin-2-yl)-ureido]-methyl}-pyrrolidine-1-carboxylic acid methyl ester;
1-(5H-Pyrrolo[2,3-b]pyrazin-2-yl)-3-{2-[1-(2,2,2-trifluoro-ethyl)-pyrrolidin-2-yl]-ethyl}-urea;
(1S,3S)-3-[3-(5H-Pyrrolo[2,3-b]pyrazin-2-yl)-ureido]-cyclopentanecarboxylic acid methylamide; and
(1S,3S)-3-[3-(5H-Pyrrolo[2,3-b]pyrazin-2-yl)-ureido]-cyclopentanecarboxylic acid ethylamide.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating arthritis comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for inhibiting T-cell proliferative disorder comprising administering to a patient in need thereof a therapeutically effective amount of the compound of Formula I.

The application provides the above method, wherein the proliferative disorder is cancer.

The application provides a method for treating a B-cell proliferative disorder comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for preventing or treating all forms of organ rejection, including acute allograft or xenograft rejection and chronic allograft or xenograft rejection, of vascularized or non-vascularized transplants, comprising administering to a patient in need thereof the compound of Formula I.

The application provides a method for inhibiting JAK3 activity comprising administering the compound of Formula I, wherein the compound exhibits an $IC_{50}$ of 50 micromolar or less in an in vitro biochemical assay of JAK3 activity.

In one variation of the above method, the compound exhibits an $IC_{50}$ of 100 nanomolar or less in an in vitro biochemical assay of JAK3 activity.

In one variation of the above method, the compound exhibits an $IC_{50}$ of 10 nanomolar or less in an in vitro biochemical assay of JAK3 activity.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

The application provides a pharmaceutical composition comprising the compound of Formula I, admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides a use of the compound of Formula I in the manufacture of a medicament for the treatment of an inflammatory disorder.

The application provides a use of the compound of Formula I in the manufacture of a medicament for the treatment of an autoimmune disorder.

The application provides a compound of Formula I

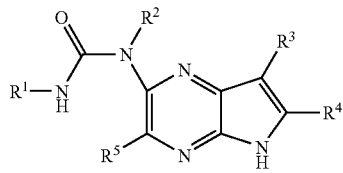

wherein:
$R^1$ is cycloalkyl, cycloalkyl lower alkyl, phenyl lower alkyl, heterocycloalkyl, heterocycloalkyl lower alkyl, heteroaryl, or heteroaryl lower alkyl, each optionally substituted with one or more $R^{1'}$;
$R^{1'}$ is halogen, lower alkyl, hydroxy, lower hydroxyalkyl, lower alkoxy, lower haloalkyl, amino, amido, oxo, cyano, sulfonamido, or cycloalkyl; and
$R^2$ is H or lower alkyl;
each of $R^3$, $R^4$, and $R^5$ are independently selected from the group consisting of H, lower alkyl, halogen, hydroxy, lower hydroxyalkyl, lower alkoxy, and lower haloalkyl;
or a pharmaceutically acceptable salt thereof.

In certain embodiments of Formula I, $R^2$ is H.
In certain embodiments of Formula I, $R^3$ is H.
In certain embodiments of Formula I, $R^2$ is H, and $R^3$ is H.
In certain embodiments of Formula I, $R^4$ is H.
In certain embodiments of Formula I, $R^2$ is H, and $R^4$ is H.
In certain embodiments of Formula I, $R^3$ is H, and $R^4$ is H.
In certain embodiments of Formula I, $R^2$ is H, $R^3$ is H, and $R^4$ is H.
In certain embodiments of Formula I, $R^5$ is H.
In certain embodiments of Formula I, $R^2$ is H, and $R^5$ is H.
In certain embodiments of Formula I, $R^3$ is H, and $R^5$ is H.
In certain embodiments of Formula I, $R^4$ is H, and $R^5$ is H.
In certain embodiments of Formula I, $R^2$ is H, $R^3$ is H, and $R^5$ is H.
In certain embodiments of Formula I, $R^2$ is H, $R^4$ is H, and $R^5$ is H.
In certain embodiments of Formula I, $R^3$ is H, $R^4$ is H, and $R^5$ is H.
In certain embodiments of Formula I, $R^2$ is H, $R^3$ is H, $R^4$ is H, and $R^5$ is H.

In certain variations of any of the above embodiments, $R^1$ is cycloalkyl.
In one variation of the above embodiment, $R^1$ is cyclohexyl.
In one variation of the above embodiment, $R^{1'}$ is lower alkyl.
In one variation of the above embodiment, $R^{1'}$ is methyl.
In certain embodiments of Formula I, $R^2$ is H.
In one variation of the above embodiment, $R^1$ is cycloalkyl lower alkyl.
In one variation of the above embodiment, $R^1$ is phenyl lower alkyl.
In one variation of the above embodiment, $R^1$ is phenylethyl.
In certain embodiments of Formula I, $R^2$ is H, $R^3$ is H, $R^4$ is H, and $R^5$ is H.
In one variation of the above embodiment, $R^1$ is cycloalkyl lower alkyl.
In one variation of the above embodiment, $R^1$ is phenyl lower alkyl.
In one variation of the above embodiment, $R^1$ is phenyl ethyl.

The application provides a compound of Formula I

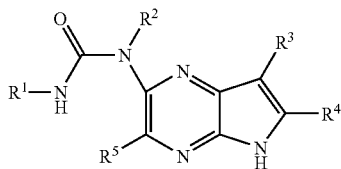

wherein:
$R^1$ is lower alkyl or phenyl, each optionally substituted with one or more $R^{1'}$;
$R^{1'}$ is halogen, lower alkyl, hydroxy, lower hydroxyalkyl, lower alkoxy, lower haloalkyl, amino, amido, oxo, cyano, sulfonamido, or cycloalkyl; and
$R^2$ is H or lower alkyl;
each of $R^3$, $R^4$, and $R^5$ are independently selected from the group consisting of H, lower alkyl, halogen, hydroxy, lower hydroxyalkyl, lower alkoxy, and lower haloalkyl;
or a pharmaceutically acceptable salt thereof.

In certain embodiments of Formula I, $R^2$ is H.
In certain embodiments of Formula I, $R^3$ is H.
In certain embodiments of Formula I, $R^2$ is H, and $R^3$ is H.
In certain embodiments of Formula I, $R^4$ is H.
In certain embodiments of Formula I, $R^2$ is H, and $R^4$ is H.
In certain embodiments of Formula I, $R^3$ is H, and $R^4$ is H.
In certain embodiments of Formula I, $R^2$ is H, $R^3$ is H, and $R^4$ is H.
In certain embodiments of Formula I, $R^5$ is H.
In certain embodiments of Formula I, $R^2$ is H, and $R^5$ is H.
In certain embodiments of Formula I, $R^3$ is H, and $R^5$ is H.
In certain embodiments of Formula I, $R^4$ is H, and $R^5$ is H.
In certain embodiments of Formula I, $R^2$ is H, $R^3$ is H, and $R^5$ is H.
In certain embodiments of Formula I, $R^2$ is H, $R^4$ is H, and $R^5$ is H.
In certain embodiments of Formula I, $R^3$ is H, $R^4$ is H, and $R^5$ is H.
In certain embodiments of Formula I, $R^2$ is H, $R^3$ is H, $R^4$ is H, and $R^5$ is H.
In certain variations of any of the above embodiments, $R^1$ is phenyl or lower alkyl.
In one variation of the above embodiment, $R^1$ is phenyl and $R^{1'}$ is halogen.
In one variation of the above embodiment, $R^1$ is phenyl and $R^{1'}$ is lower haloalkyl.

In one aspect, the application provides a method for treating an inflammatory and/or autoimmune condition comprising administering to a patient in need thereof a therapeutically effective amount of the compound of Formula I.

In one variation of the above method, the above method further comprises administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

In one aspect, the application provides a method for treating an inflammatory condition comprising administering to a patient in need thereof a therapeutically effective amount of the compound of Formula I.

In one aspect, the application provides a method for inhibiting T-cell proliferative disorder comprising administering to a patient in need thereof a therapeutically effective amount of the compound of Formula I.

In one aspect, the application provides a method for inhibiting T-cell proliferative disorder comprising administering to a patient in need thereof a therapeutically effective amount of the compound of Formula I, wherein R is $R^2$.

In one variation of the above method, the proliferative disorder is cancer.

In one aspect, the application provides a method for treating a B-cell proliferative disorder comprising administering to a patient in need thereof a therapeutically effective amount of the compound of Formula I.

In one aspect, the application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

In one aspect, the application provides a method for preventing or treating all forms of organ rejection, including acute allograft or xenograft rejection and chronic allograft or xenograft rejection, of vascularized or non-vascularized transplants, comprising administering to a patient in need thereof a therapeutically effective amount of the compound of Formula I.

In one aspect, the application provides a method for inhibiting JAK3 activity comprising administering a therapeutically effective amount of the compound of Formula I.

In one variation of the above method, the compound exhibits an $IC_{50}$ of 50 micromolar or less in an in vitro biochemical assay of JAK3 activity.

In one variation of the above method, the compound exhibits an $IC_{50}$ of 100 nanomolar or less in an in vitro biochemical assay of JAK3 activity.

In one variation of the above method, the compound exhibits an $IC_{50}$ of 10 nanomolar or less in an in vitro biochemical assay of JAK3 activity.

In one aspect, the application provides a method for treating an inflammatory condition comprising co-administering to a patient in need thereof an anti-inflammatory compound in combination with a therapeutically effective amount of the compound of Formula I.

In one aspect, the application provides a method for treating an immune disorder comprising co-administering to a patient in need thereof an immunosuppressant compound in combination with a therapeutically effective amount of the compound of Formula I.

The application provides a pharmaceutical composition comprising the compound of Formula I, admixed with at least one pharmaceutically acceptable carrier, excipient or diluent.

In one variation, the above pharmaceutical composition further comprises an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

In one aspect, the application provides a use of the compound of Formula I, in the manufacture of a medicament for the treatment of an inflammatory disorder.

In one aspect, the application provides a use of the compound of Formula I, in the manufacture of a medicament for the treatment of an autoimmune disorder.

In one aspect, the application provides a method for treating an inflammatory and/or autoimmune condition comprising administering to a patient in need thereof a therapeutically effective amount of the compound of Formula I.

In one variation of the above method, the above method further comprises administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

In one aspect, the application provides a method for treating an inflammatory condition comprising administering to a patient in need thereof a therapeutically effective amount of the compound of Formula I, wherein R is $R^1$.

In one aspect, the application provides a method for inhibiting T-cell proliferative disorder comprising administering to a patient in need thereof a therapeutically effective amount of the compound of Formula I.

In one aspect, the application provides a method for inhibiting T-cell proliferative disorder comprising administering to a patient in need thereof a therapeutically effective amount of the compound of Formula I, wherein R is $R^2$.

In one variation of the above method, the proliferative disorder is cancer.

In one aspect, the application provides a method for treating a B-cell proliferative disorder comprising administering to a patient in need thereof a therapeutically effective amount of the compound of Formula I.

In one aspect, the application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

In one aspect, the application provides a method for preventing or treating all forms of organ rejection, including acute allograft or xenograft rejection and chronic allograft or xenograft rejection, of vascularized or non-vascularized transplants, comprising administering to a patient in need thereof a therapeutically effective amount of the compound of Formula I.

In one aspect, the application provides a method for inhibiting JAK3 activity comprising administering the compound of Formula I, wherein the compound exhibits an $IC_{50}$ of 50 micromolar or less in an in vitro biochemical assay of JAK3 activity.

In one variation of the above method, the compound exhibits an $IC_{50}$ of 100 nanomolar or less in an in vitro biochemical assay of JAK3 activity.

In one variation of the above method, the compound exhibits an $IC_{50}$ of 10 nanomolar or less in an in vitro biochemical assay of JAK3 activity.

In one aspect, the application provides a method for treating an inflammatory condition comprising co-administering to a patient in need thereof an anti-inflammatory compound in combination with a therapeutically effective amount of the compound of Formula I.

In one aspect, the application provides a method for treating an immune disorder comprising co-administering to a patient in need thereof an immunosuppressant compound in combination with a therapeutically effective amount of the compound of Formula I.

The application provides a pharmaceutical composition comprising the compound of Formula I, admixed with at least one pharmaceutically acceptable carrier, excipient or diluent.

In one variation, the above pharmaceutical composition further comprises an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

In one aspect, the application provides a use of the compound of Formula I, in the manufacture of a medicament for the treatment of an inflammatory disorder.

In one aspect, the application provides a use of the compound of Formula I, in the manufacture of a medicament for the treatment of an autoimmune disorder.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R, R', or Q) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----" drawn through a bond each refer to the point of attachment of a functional group or other chemical moiety to the rest of the molecule of which it is a part. Thus, for example:

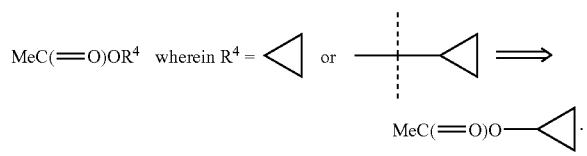

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "come together to form a bicyclic ring system" as used herein means join to form a bicyclic ring system, wherein each ring may be made up of either 4-7 carbon atoms or 4-7 carbon and heteroatoms, and may be saturated or unsaturated.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," "cycloalkylalkyl" and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Compounds of formula I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl", "aryl alkyl", or "aralkyl" are interpreted similarly except R' is an aryl radical. The terms "heteroaryl alkyl" or "heteroarylalkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. The term "lower haloalkyl" denotes a straight or branched chain hydrocarbon residue containing 1 to 6 carbon atoms, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "hydroxyalkyl" as used herein denotes an alkyl radical as herein defined wherein one to three hydrogen atoms on different carbon atoms is/are replaced by hydroxyl groups.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl, bicycloheptyl, or cyclooctyl. "$C_{3-7}$ cycloalkyl" as used herein refers to an cycloalkyl composed of 3 to 7 carbons in the carbocyclic ring.

The term "spirocycloalkyl" as used herein refers to a cycloalkyl as described above wherein one of the ring carbon atoms of the cycloalkyl is a ring carbon atom of second ring which is cycloalkyl, preferably this second ring is a cyclopropyl. For example, spirocycloalkyl may be spiro[2,5]octyl.

The term "halogen" or "halo" as used herein means fluorine, chlorine, bromine, or iodine.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiazoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocycloalkyl", "heterocyclyl" or "heterocycle" as used herein denotes a monovalent saturated cyclic radical, consisting of one or more rings, preferably one to two rings, of three to eight atoms per ring, incorporating one or more ring carbon atoms and one or more ring heteroatoms (chosen from N, O or S($=$O)$_{0-2}$), wherein the point of attachment can be through either a carbon atom or a heteroatom, and which can optionally be independently substituted with one or more, preferably one or two or three substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, azepanyl, thiazolidinyl, isoxazolidinyl, morpholinyl, piperazinyl, piperidinyl, tetrahydropyranyl, thiomorpholinyl, quinuclidinyl and imidazolinyl.

The phrase "organ rejection" includes acute allograft or xenograft rejection and chronic allograft or xenograft rejection in the setting of vascularized and/or non-vascularized (e.g. bone marrow, pancreatic islet cells) transplants.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tent-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), trimethylsilanyl-ethoxymethyl (SEM), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts exemplified compounds according to Formula I.

TABLE I

| COMPOUND | SYSTEMATIC NAME | STRUCTURE | MS Data (M + 1) |
|---|---|---|---|
| I-1 | 1-Cyclohexyl-3-(5H-pyrrolo[2,3-b]pyrazin-2-yl)-urea | 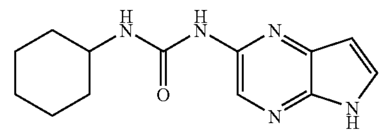 | 260 |
| I-2 | 1-Phenyl-3-(5H-pyrrolo[2,3-b]pyrazin-2-yl)-urea | 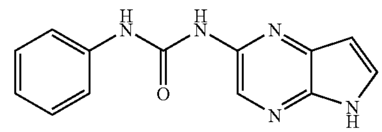 | 254 |
| I-3 | 1-Cyclopentyl-3-(5H-pyrrolo[2,3-b]pyrazin-2-yl)-urea | 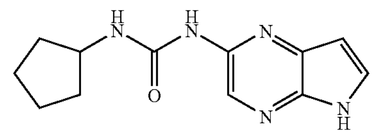 | 246 |
| I-4 | 1-Cycloheptyl-3-(5H-pyrrolo[2,3-b]pyrazin-2-yl)-urea | 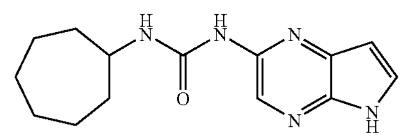 | 274 |
| I-5 | 1-Benzyl-3-(5H-pyrrolo[2,3-b]pyrazin-2-yl)-urea | 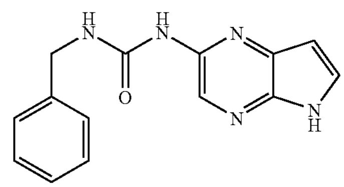 | 282 |
| I-6 | 1-Cyclohexylmethyl-3-(5H-pyrrolo[2,3-b]pyrazin-2-yl)-urea | 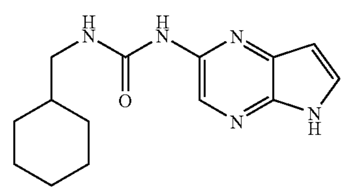 | 274 |
| I-7 | 1-((1S,2R)-2-Methyl-cyclohexyl)-3-(5H-pyrrolo[2,3-b]pyrazin-2-yl)-urea | 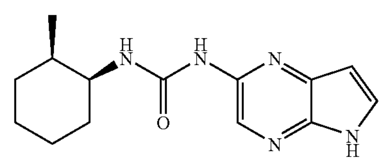 | 274 |
| I-8 | 1-(2-Chloro-phenyl)-3-(5H-pyrrolo[2,3-b]pyrazin-2-yl)-urea | 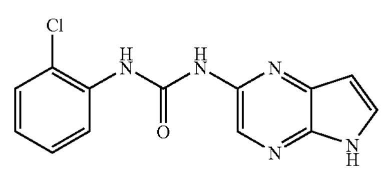 | 288 |

TABLE I-continued

| COMPOUND | SYSTEMATIC NAME | STRUCTURE | MS Data (M + 1) |
|---|---|---|---|
| I-9 | 1-((R)-1-Phenyl-ethyl)-3-(5H-pyrrolo[2,3-b]pyrazin-2-yl)-urea | 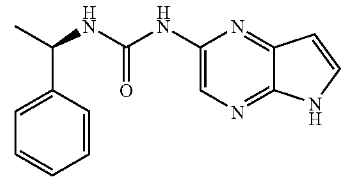 | 282 |
| I-10 | 1-Phenethyl-3-(5H-pyrrolo[2,3-b]pyrazin-2-yl)-urea | 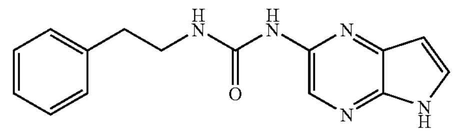 | 282 |
| I-11 | 1-((S)-1-Phenyl-ethyl)-3-(5H-pyrrolo[2,3-b]pyrazin-2-yl)-urea | 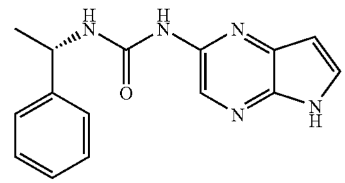 | 282 |
| I-12 | 1-(5H-Pyrrolo[2,3-b]pyrazin-2-yl)-3-o-tolyl-urea | 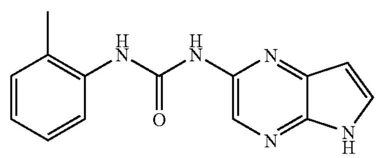 | 268 |
| I-13 | 1-(5H-Pyrrolo[2,3-b]pyrazin-2-yl)-3-(2-trifluoromethyl-phenyl)-urea | 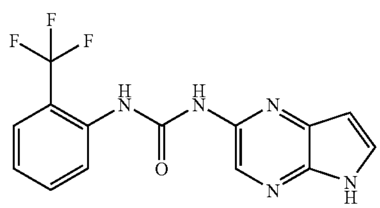 | 322 |
| I-14 | 1-Ethyl-3-(5H-pyrrolo[2,3-b]pyrazin-2-yl)-urea | 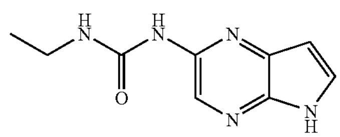 | 206 |
| I-15 | 1-tert-Butyl-3-(5H-pyrrolo[2,3-b]pyrazin-2-yl)-urea | 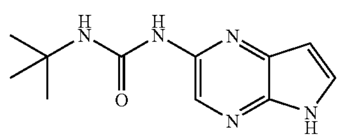 | 234 |
| I-16 | 1-Isopropyl-3-(5H-pyrrolo[2,3-b]pyrazin-2-yl)-urea | 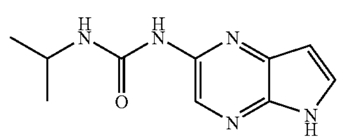 | 220 |
| I-17 | [3-(5H-Pyrrolo[2,3-b]pyrazin-2-yl)-ureido]-acetic acid ethyl ester | 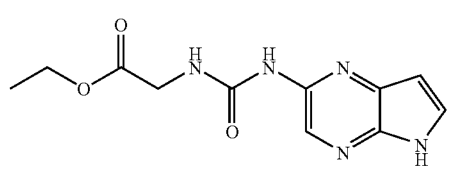 | |

TABLE I-continued

| COMPOUND | SYSTEMATIC NAME | STRUCTURE | MS Data (M + 1) |
|---|---|---|---|
| I-18 | N-Methyl-2-[3-(5H-pyrrolo[2,3-b]pyrazin-2-yl)-ureido]-acetamide | 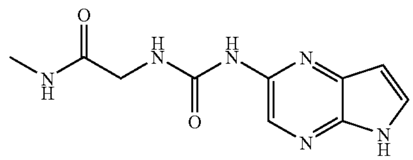 | |
| I-19 | (S)-3-Methyl-2-[3-(5H-pyrrolo[2,3-b]pyrazin-2-yl)-ureido]-butyric acid methyl ester | 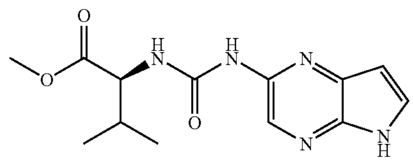 | |
| I-20 | (S)-3,N-Dimethyl-2-[3-(5H-pyrrolo[2,3-b]pyrazin-2-yl)-ureido]-butyramide | 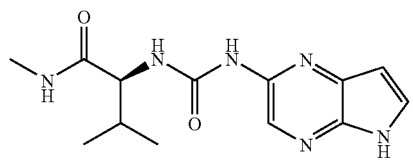 | |
| I-21 | 1-((3S,4S)-3-Methyl-tetrahydro-pyran-4-yl)-3-(5H-pyrrolo[2,3-b]pyrazin-2-yl)-urea | 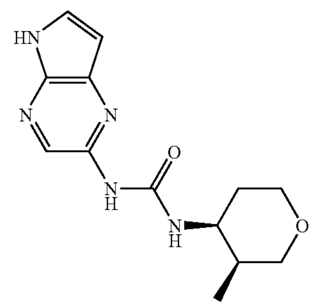 | |
| I-22 | 1-(5H-Pyrrolo[2,3-b]pyrazin-2-yl)-3-((1S,2R)-2,5,5-trimethyl-cyclohexyl)-urea | 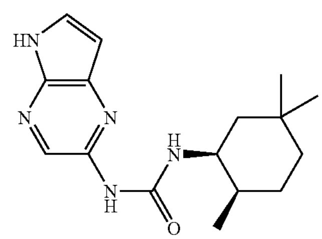 | |
| I-23 | 1-(1-Acetyl-piperidin-3-yl)-3-(5H-pyrrolo[2,3-b]pyrazin-2-yl)-urea | 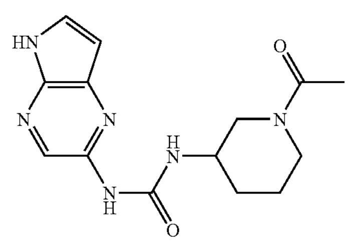 | |
| I-24 | 1-(3,3-Dimethyl-cyclohexyl)-3-(5H-pyrrolo[2,3-b]pyrazin-2-yl)-urea | 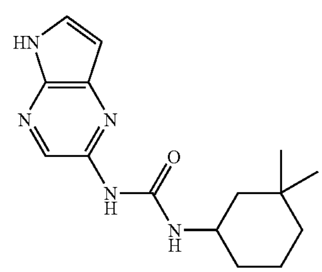 | |

TABLE I-continued

| COMPOUND | SYSTEMATIC NAME | STRUCTURE | MS Data (M + 1) |
|---|---|---|---|
| I-25 | 1-(3-Methyl-cyclohexyl)-3-(5H-pyrrolo[2,3-b]pyrazin-2-yl)-urea | 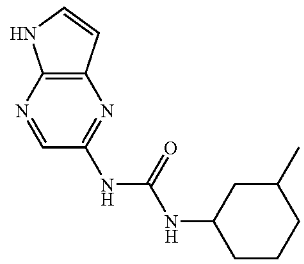 | |
| I-26 | 1-((1R,2S)-2-Methyl-cyclohexyl)-3-(5H-pyrrolo[2,3-b]pyrazin-2-yl)-urea | 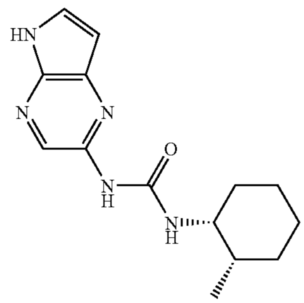 | |
| I-27 | 1-(5H-Pyrrolo[2,3-b]pyrazin-2-yl)-3-spiro[2.5]oct-5-yl-urea | 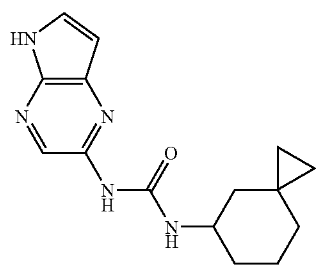 | |
| I-28 | 3-Cyclohexyl-1-methyl-1-(5H-pyrrolo[2,3-b]pyrazin-2-yl)-urea | 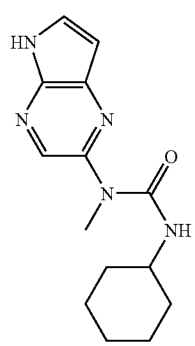 | |
| I-29 | 1-[1-(2-Cyano-acetyl)-piperidin-3-yl]-3-(5H-pyrrolo[2,3-b]pyrazin-2-yl)-urea | 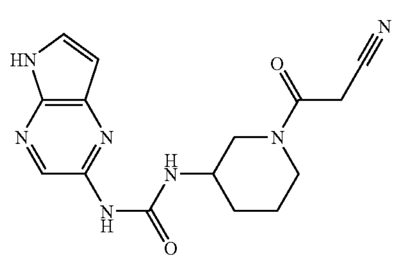 | |

TABLE I-continued

| COMPOUND | SYSTEMATIC NAME | STRUCTURE | MS Data (M + 1) |
|---|---|---|---|
| I-30 | 1-(2,2-Dimethyl-cyclopentyl)-3-(5H-pyrrolo[2,3-b]pyrazin-2-yl)-urea | 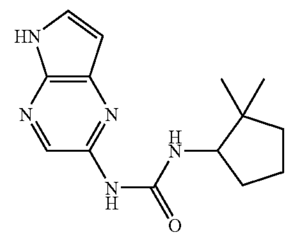 | |
| I-31 | 1-(5H-Pyrrolo[2,3-b]pyrazin-2-yl)-3-[1-(2,2,2-trifluoro-ethyl)-piperidin-3-yl]-urea | 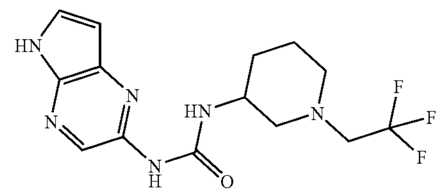 | |
| I-32 | 1-(1-Methanesulfonyl-piperidin-3-yl)-3-(5H-pyrrolo[2,3-b]pyrazin-2-yl)-urea | 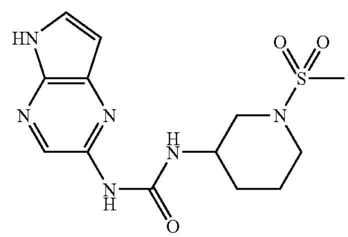 | |
| I-33 | 3-[3-(5H-Pyrrolo[2,3-b]pyrazin-2-yl)-ureido]-piperidine-1-carboxylic acid methyl ester | 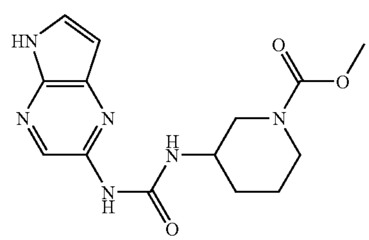 | |
| I-34 | 1-((S)-1-Acetyl-piperidin-3-yl)-3-(5H-pyrrolo[2,3-b]pyrazin-2-yl)-urea | 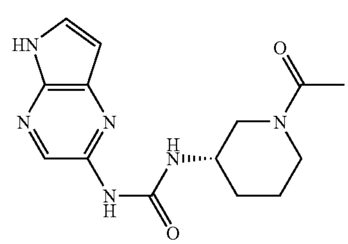 | |
| I-35 | 1-((1R,3R)-3-Amino-cyclopentyl)-3-(5H-pyrrolo[2,3-b]pyrazin-2-yl)-urea | 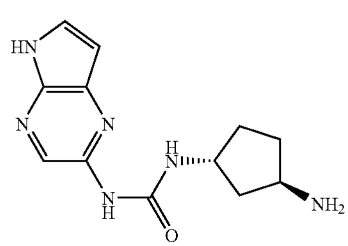 | |

TABLE I-continued

| COMPOUND | SYSTEMATIC NAME | STRUCTURE | MS Data (M + 1) |
|---|---|---|---|
| I-36 | 1-(5H-Pyrrolo[2,3-b]pyrazin-2-yl)-3-[1-(3,3,3-trifluoro-propionyl)-piperidin-3-yl]-urea | 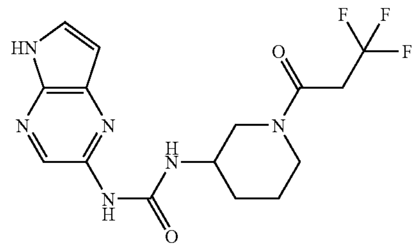 | |
| I-37 | 1-((R)-1-Acetyl-piperidin-3-yl)-3-(5H-pyrrolo[2,3-b]pyrazin-2-yl)-urea | 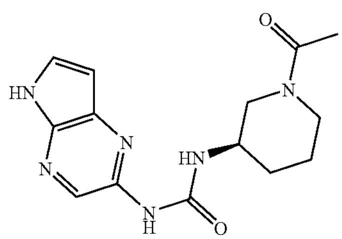 | |
| I-38 | 3-[3-(5H-Pyrrolo[2,3-b]pyrazin-2-yl)-ureido]-piperidine-1-carboxylic acid ethyl ester | 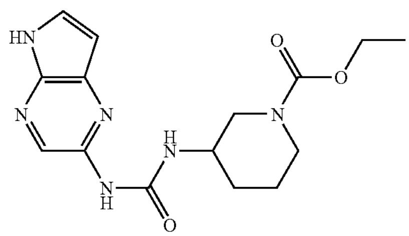 | |
| I-39 | 1-(1-Propionyl-piperidin-3-yl)-3-(5H-pyrrolo[2,3-b]pyrazin-2-yl)-urea | 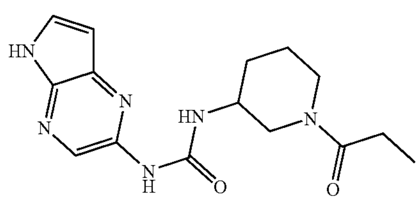 | |
| I-40 | 1-(1-Isobutyryl-piperidin-3-yl)-3-(5H-pyrrolo[2,3-b]pyrazin-2-yl)-urea | 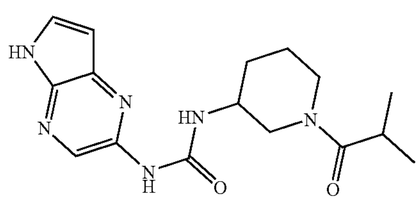 | |
| I-41 | 1-[1-(3-Methyl-butyryl)-piperidin-3-yl]-3-(5H-pyrrolo[2,3-b]pyrazin-2-yl)-urea | 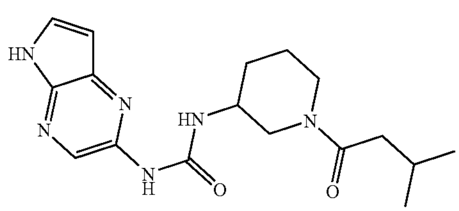 | |

TABLE I-continued

| COMPOUND | SYSTEMATIC NAME | STRUCTURE | MS Data (M + 1) |
|---|---|---|---|
| I-42 | 1-Cyclohexyl-3-(6-methyl-5H-pyrrolo[2,3-b]pyrazin-2-yl)-urea | 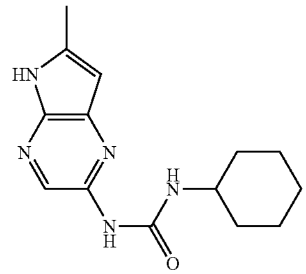 | |
| I-43 | 1-Cyclohexyl-3-(7-methyl-5H-pyrrolo[2,3-b]pyrazin-2-yl)-urea | 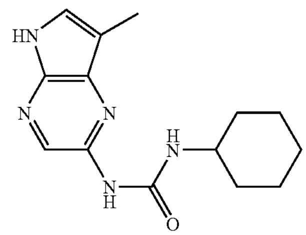 | |
| I-44 | 1-(1-Ethanesulfonyl-piperidin-3-yl)-3-(5H-pyrrolo[2,3-b]pyrazin-2-yl)-urea | 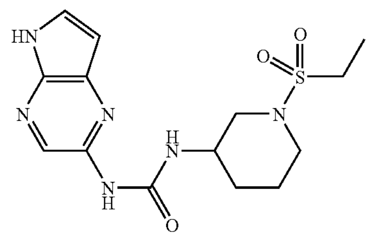 | |
| I-45 | 1-[1-(Propane-2-sulfonyl)-piperidin-3-yl]-3-(5H-pyrrolo[2,3-b]pyrazin-2-yl)-urea | 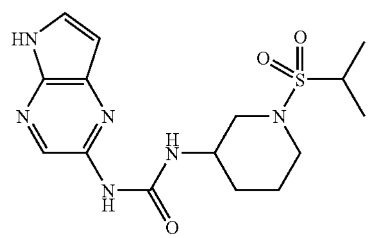 | |
| I-46 | 1-((S)-1-Acetyl-pyrrolidin-3-yl)-3-(5H-pyrrolo[2,3-b]pyrazin-2-yl)-urea | 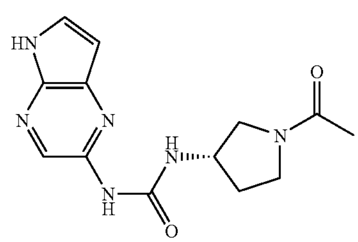 | |
| I-47 | 1-((S)-1-Methanesulfonyl-pyrrolidin-3-yl)-3-(5H-pyrrolo[2,3-b]pyrazin-2-yl)-urea | 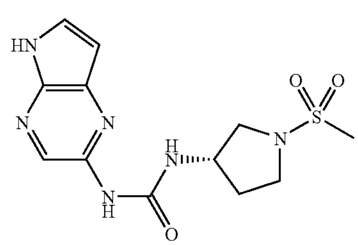 | |

TABLE I-continued

| COMPOUND | SYSTEMATIC NAME | STRUCTURE | MS Data (M + 1) |
|---|---|---|---|
| I-48 | (S)-3-[3-(5H-Pyrrolo[2,3-b]pyrazin-2-yl)-ureido]-pyrrolidine-1-carboxylic acid methyl ester | 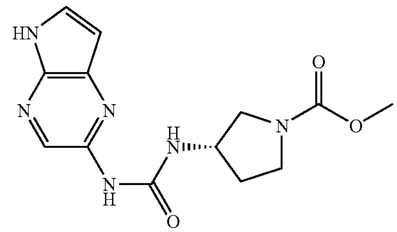 | |
| I-49 | 1-((3S,5S)-1-Acetyl-5-methyl-piperidin-3-yl)-3-(5H-pyrrolo[2,3-b]pyrazin-2-yl)-urea | 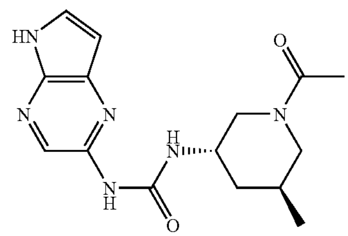 | |
| I-50 | 1-(1-Cyclopropanesulfonyl-piperidin-3-yl)-3-(5H-pyrrolo[2,3-b]pyrazin-2-yl)-urea | 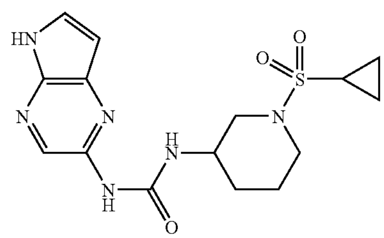 | |
| I-51 | 1-[1-Propane-1-sulfonyl)-piperidin-3-yl]-3-(5H-pyrrolo[2,3-b]pyrazin-2-yl)-urea | 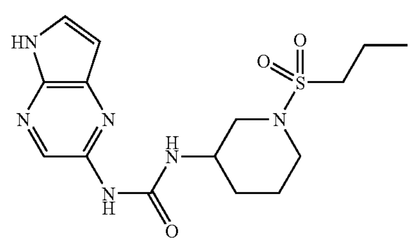 | |
| I-52 | 1-((5R,6S)-6-Methyl-spiro[2.5]oct-5-yl)-3-(5H-pyrrolo[2,3-b]pyrazin-2-yl)-urea | 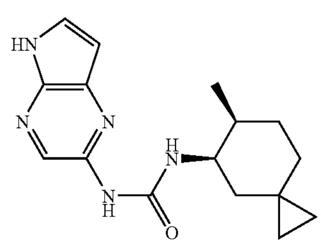 | |
| I-53 | 1-((5S,6R)-6-Methyl-spiro[2.5]oct-5-yl)-3-(5H-pyrrolo[2,3-b]pyrazin-2-yl)-urea | 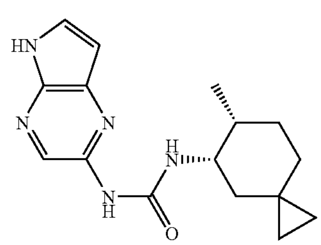 | |

TABLE I-continued

| COMPOUND | SYSTEMATIC NAME | STRUCTURE | MS Data (M + 1) |
|---|---|---|---|
| I-54 | 1-Pyridin-2-ylmethyl-3-(5H-pyrrolo[2,3-b]pyrazin-2-yl)-urea | 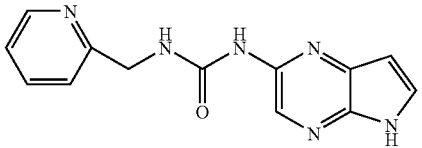 | |
| I-55 | 1-Pyridin-3-ylmethyl-3-(5H-pyrrolo[2,3-b]pyrazin-2-yl)-urea | 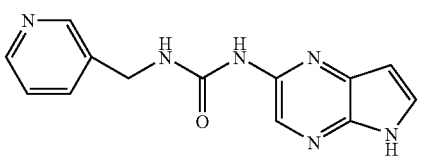 | |
| I-56 | 1-(2-Pyridin-2-yl-ethyl)-3-(5H-pyrrolo[2,3-b]pyrazin-2-yl)-urea | 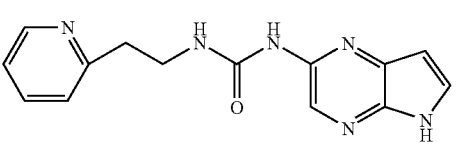 | |
| I-57 | 1-(2-Pyridin-3-yl-ethyl)-3-(5H-pyrrolo[2,3-b]pyrazin-2-yl)-urea | 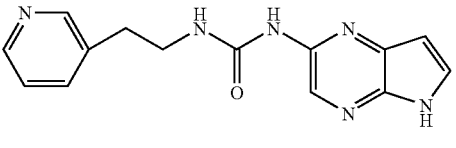 | |
| I-58 | 1-(2-Isopropyl-cyclohexyl)-3-(5H-pyrrolo[2,3-b]pyrazin-2-yl)-urea | 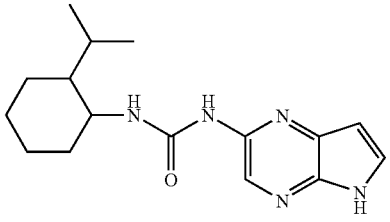 | |
| I-59 | 1-((1S,2R)-2-Methyl-cycloheptyl)-3-(5H-pyrrolo[2,3-b]pyrazin-2-yl)-urea | 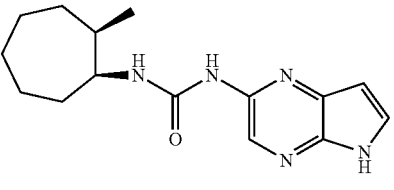 | |
| I-60 | 1-((1R,2R)-2-Methyl-cyclohexyl)-3-(5H-pyrrolo[2,3-b]pyrazin-2-yl)-urea | 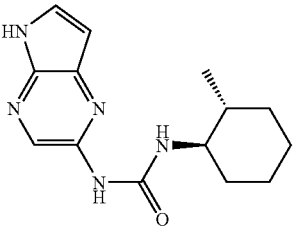 | |
| I-61 | 1-((1S,2S)-2-Methyl-cyclohexyl)-3-(5H-pyrrolo[2,3-b]pyrazin-2-yl)-urea | 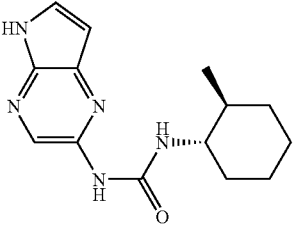 | |

TABLE I-continued

| COMPOUND | SYSTEMATIC NAME | STRUCTURE | MS Data (M + 1) |
|---|---|---|---|
| I-62 | (R)-3-[3-(5H-Pyrrolo[2,3-b]pyrazin-2-yl)-ureido]-pyrrolidine-1-carboxylic acid methyl ester | 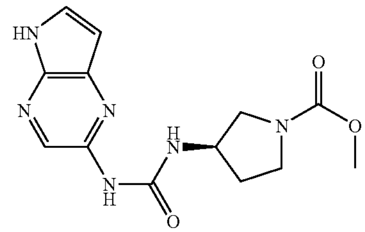 | |
| I-63 | 1-((R)-1-Acetyl-Methanesuflonyl-pyrrolidin-3-yl)-3-(5H-pyrrolo[2,3-b]pyrazin-2-yl)-urea | 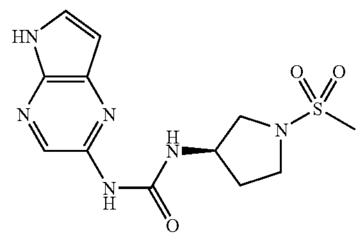 | |
| I-64 | 1-((R)-1-Acetyl-pyrolidin-3-yl)-3-(5H-pyrrolo[2,3-b]pyrazin-2-yl)-urea | 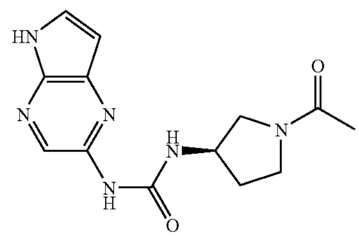 | |
| I-65 | 1-(1-Cyclopropanecarbonyl-piperidin-3-yl)-3-(5H-pyrrolo[2,3-b]pyrazin-2-yl)-urea | 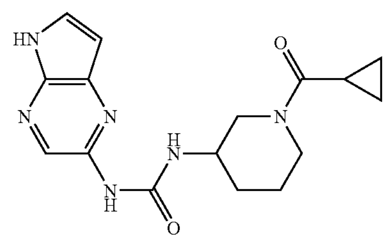 | |
| I-66 | 1-(5H-Pyrrolo[2,3-b]pyrazin-2-yl)-3-(1-trifluoromethanesulfonyl-piperidin-3-yl)-urea | 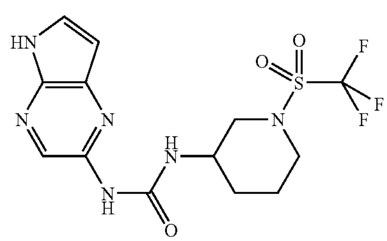 | |
| I-67 | 1-(5H-Pyrrolo[2,3-b]pyrazin-2-yl)-3-[1-(2,2,2-trifluoro-ethanesulfonyl)-piperidin-3-yl]-urea | 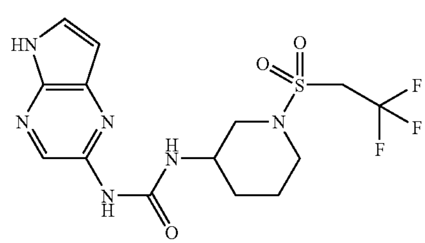 | |

TABLE I-continued

| COMPOUND | SYSTEMATIC NAME | STRUCTURE | MS Data (M + 1) |
|---|---|---|---|
| I-68 | 1-(2-Ethyl-cyclohexyl)-3-(5H-pyrrolo[2,3-b]pyrazin-2-yl)-urea | 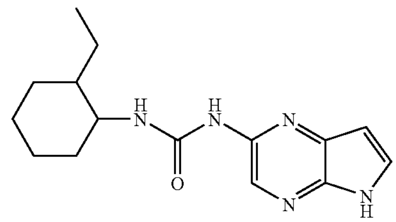 | |
| I-69 | 1-(1-Acetyl-3-methyl-piperidin-4-yl)-3-(5H-pyrrolo[2,3-b]pyrazin-2-yl)-urea | 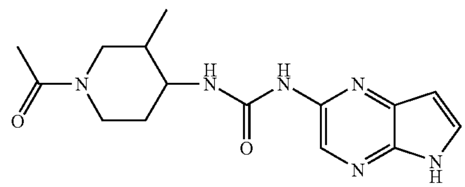 | |
| I-70 | 1-(1-Methanesulfonyl-3-methyl-piperidin-4-yl)-3-(5H-pyrrolo[2,3-b]pyrazin-2-yl)-urea | 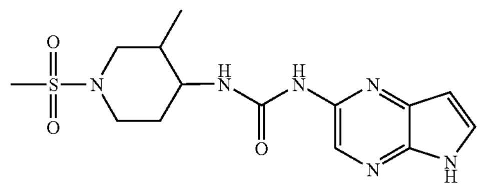 | |
| I-71 | 3-Methyl-4-[3-(5H-pyrrolo[2,3-b]pyrazin-2-yl)-ureido]-piperidine-1-carboxylic acid methyl ester | 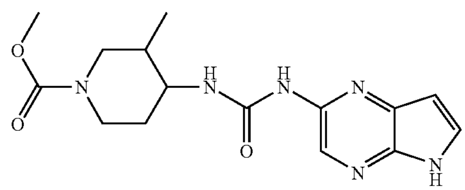 | |
| I-72 | 1-(1-Methanesulfonyl-pyrrolidin-2-ylmethyl)-3-(5H-pyrrolo[2,3-b]pyrazin-2-yl)-urea | 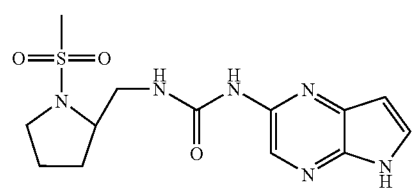 | |
| I-73 | 1-[1-(2-Cyclopropyl-acetyl)-piperidin-3-yl]-3-(5H-pyrrolo[2,3-b]pyrazin-2-yl)-urea | 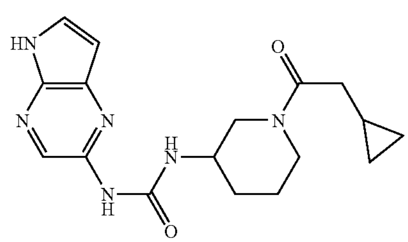 | |
| I-74 | 1-(1-Methanesulfonyl-azepan-3-yl)-3-(5H-pyrrolo[2,3-b]pyrazin-2-yl)-urea | 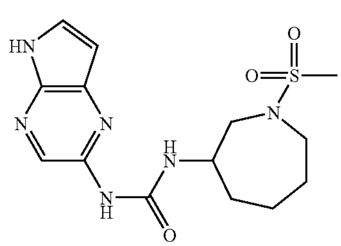 | |

TABLE I-continued

| COMPOUND | SYSTEMATIC NAME | STRUCTURE | MS Data (M + 1) |
|---|---|---|---|
| I-75 | 3-[3-(5H-Pyrrolo[2,3-b]pyrazin-2-yl)-ureido]-azepane-1-carboxylic acid methyl ester | 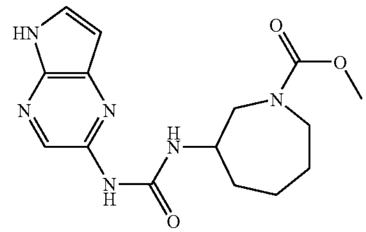 | |
| I-76 | 1-(1-Acetyl-azepan-3-yl)-3-(5H-pyrrolo[2,3-b]pyrazin-2-yl)-urea | 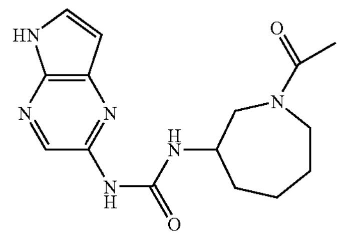 | |
| I-77 | 1-[1-(2-Methyl-propane-1-sulfonyl)-piperidin-3-yl]-3-(5H-pyrrolo[2,3-b]pyrazin-2-yl)-urea | 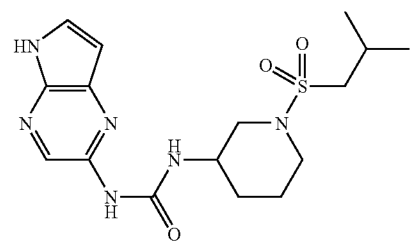 | |
| I-78 | 1-(1-Methanesulfonyl-piperidin-4-yl)-3-(5H-pyrrolo[2,3-b]pyrazin-2-yl)-urea | 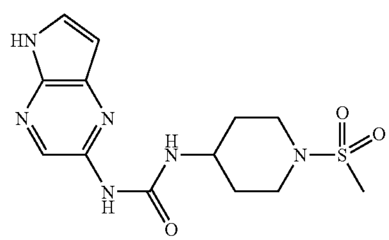 | |
| I-79 | 1-(1-Acetyl-piperidin-4-yl)-3-(5H-pyrrolo[2,3-b]pyrazin-2-yl)-urea | 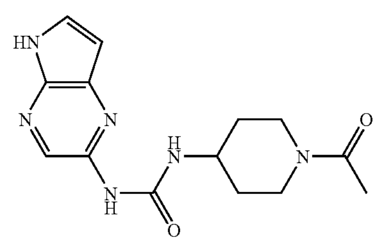 | |
| I-80 | 1-[1-(Butane-2-sulfonyl)-piperidin-3yl]-3-(5H-pyrrolo[2,3-b]pyrazin-2-yl)-urea | 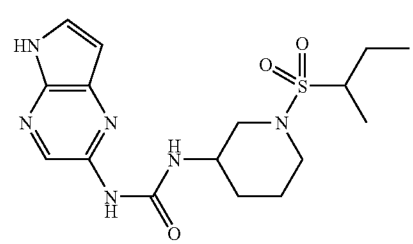 | |

TABLE I-continued

| COMPOUND | SYSTEMATIC NAME | STRUCTURE | MS Data (M + 1) |
|---|---|---|---|
| I-81 | 1-((R)-1-Methanesulfonyl-piperidin-3-yl)-3-(5H-pyrrolo[2,3-b]pyrazin-2-yl)-urea | 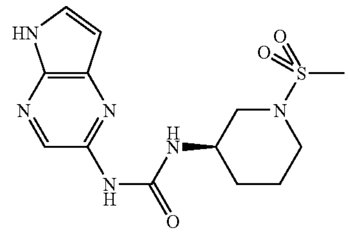 | |
| I-82 | 1-[(R)-1-(Propane-1-sulfonyl)-piperidin-3-yl]-3-(5H-pyrrolo[2,3-b]pyrazin-2-yl)-urea | 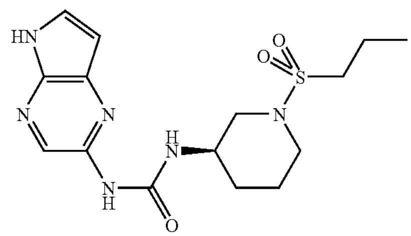 | |
| I-83 | 4-[3-(5H-Pyrrolo[2,3-b]pyrazin-2-yl)-uriedo]-piperidine-1-carboxylic acid methyl ester | 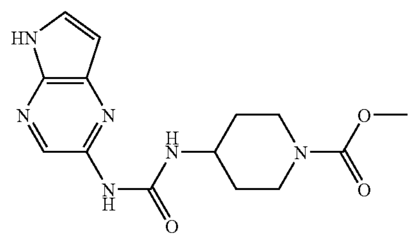 | |
| I-84 | 1-(1R,2R,4S)-Bicyclo[2.2.1]hept-2-yl-3-(5H-pyrrolo[2,3-b]pyrazin-2-yl)-urea | 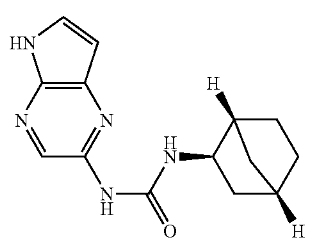 | |
| I-85 | 1-(1R,2S,4S)-Bicyclo[2.2.1]hept-2-yl-3-(5H-pyrrolo[2,3-b]pyrazin-2-yl)-urea | 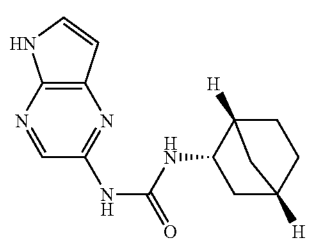 | |
| I-86 | 1-(1-Methyl-cyclohexyl)-3-(5H-pyrrolo[2,3-b]pyrazin-2-yl)-urea | 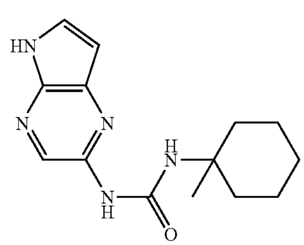 | |

TABLE I-continued

| COMPOUND | SYSTEMATIC NAME | STRUCTURE | MS Data (M + 1) |
|---|---|---|---|
| I-87 | 1-(1-Cyclopropylmethane-sulfonyl-piperidin-3-yl)-3-(5H-pyrrolo[2,3-b]pyrazin-2-yl)-urea | 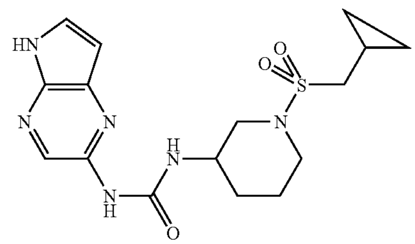 | |
| I-88 | 1-((1S,3S)-3-Hydroxymethyl-cyclohexyl)-3-(5H-pyrrolo[2,3-b]pyrazin-2-yl)-urea | 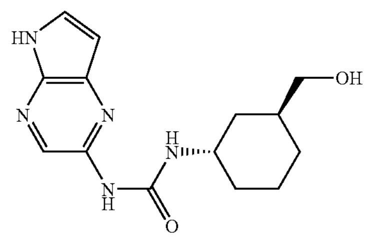 | |
| I-89 | 1-[(R)-1-(2-Methyl-propane-1-sulfonyl)-piperidin-3-yl]-3-(5H-pyrrolo[2,3-b]pyrazin-2-yl)-urea | 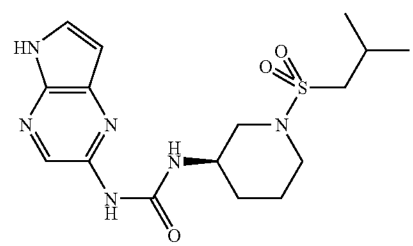 | |
| I-90 | 1-((S)-1-Methanesulfonyl-piperidin-3-yl)-3-(5H-pyrrolo[2,3-b]pyrazin-2-yl)-urea | 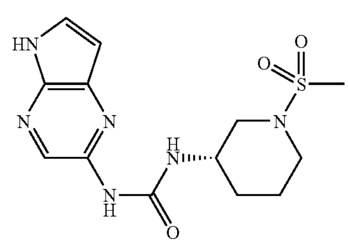 | |
| I-91 | 1-[(S)-1-(Propane-1-sulfonyl)-piperidin-3-yl]-3-(5H-pyrrolo[2,3-b]pyrazin-2-yl)-urea | 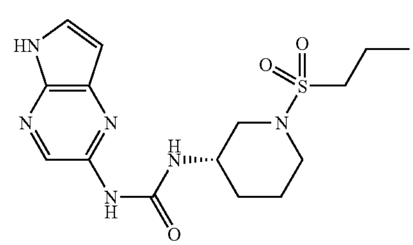 | |
| I-92 | 1-[(S)-1-(2-Methyl-propane-1-sulfonyl)-piperidin-3-yl]-3-(5H-pyrrolo[2,3-b]pyrazin-2-yl)-urea | 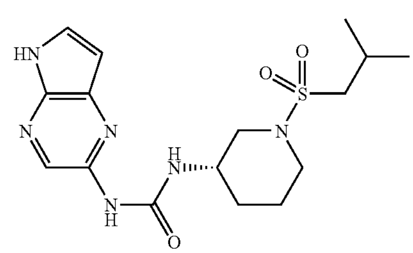 | |

TABLE I-continued

| COMPOUND | SYSTEMATIC NAME | STRUCTURE | MS Data (M + 1) |
|---|---|---|---|
| I-93 | 1-(7-Chloro-5H-pyrrolo[2,3-b]pyrazin-2-yl)-3-cyclohexyl-urea | 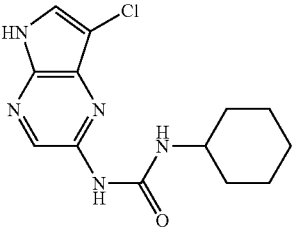 | |
| I-94 | 1-[(S)-1-(Propane-1-sulfonyl)-pyrrolidin-3-yl]-3-(5H-pyrrolo[2,3-b]pyrazin-2-yl)-urea | 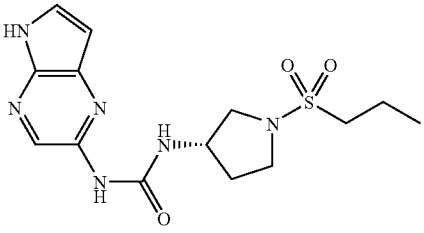 | |
| I-95 | 1-[(S)-1-(2-Methyl-propane-1-sulfonyl)-pyrrolidin-3-yl]-3-(5H-pyrrolo[2,3-b]pyrazin-2-yl)-urea | 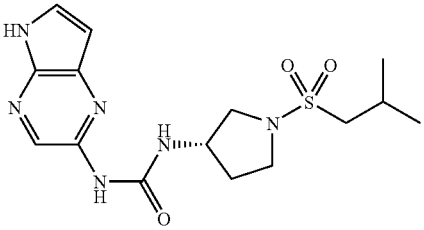 | |
| I-96 | 1-[1-(Propane-1-sulfonyl)-azepan-3-yl]-3-(5H-pyrrolo[2,3-b]pyrazin-2-yl)-urea | 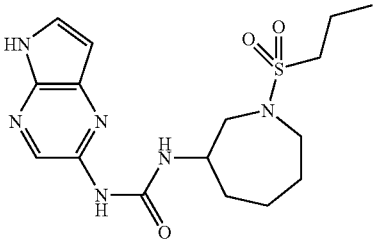 | |
| I-97 | 1-[1-(2-Methyl-propane-1-sulfonyl)-azepan-3-yl]-3-(5H-pyrrolo[2,3-b]pyrazin-2-yl)-urea | 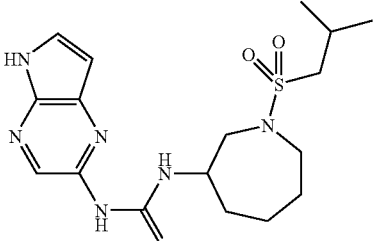 | |
| I-98 | 1-[(3S,5S)-5-Methyl-1-(propane-1-sulfonyl)-piperidin-3-yl]-3-(5H-pyrrolo[2,3-b]pyrazin-2-yl)-urea | 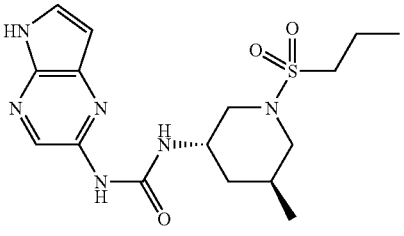 | |

TABLE I-continued

| COMPOUND | SYSTEMATIC NAME | STRUCTURE | MS Data (M + 1) |
|---|---|---|---|
| I-99 | 1-[(3S,5S)-5-Methyl-1-(2-methyl-propane-1-sulfonyl)-piperidin-3-yl]-3-(5H-pyrrolo[2,3-b]pyrazin-2-yl)-urea | 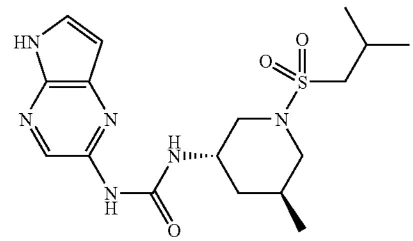 | |
| I-100 | 1-((R)-1-Ethanesulfonyl-pyrrolidin-3-yl)-3-(5H-pyrrolo[2,3-b]pyrazin-2-yl)-urea | 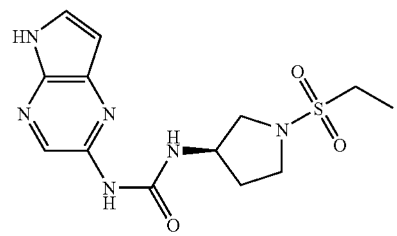 | |
| I-101 | 1-[(R)-1-(Propane-2-sulfonyl)-pyrrolidin-3-yl]-3-(5H-pyrrolo[2,3-b]pyrazin-2-yl)-urea | 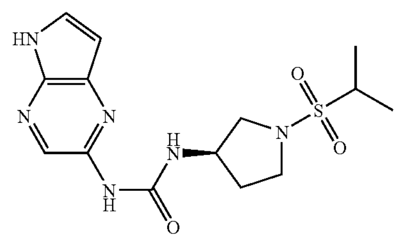 | |
| I-102 | 1-[(R)-1-(Propane-1-sulfonyl)-pyrrolidin-3-yl]-3-(5H-pyrrolo[2,3-b]pyrazin-2-yl)-urea | 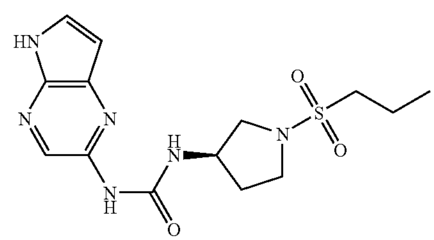 | |
| I-103 | 1-[(R)-1-(2-Methyl-propane-1-sulfonyl)-pyrrolidin-3-yl]-3-(5H-pyrrolo[2,3-b]pyrazin-2-yl)-urea | 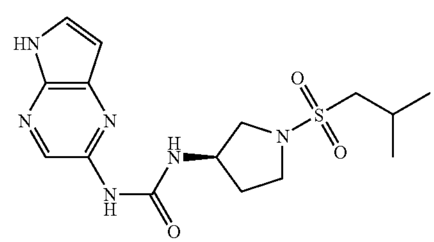 | |
| I-104 | 1-(5H-Pyrrolo[2,3-b[9 pyrazin-2-yl)-3-((R)-1-trifluoromethane-sulfonyl-pyrrolidin-3-yl)-urea | 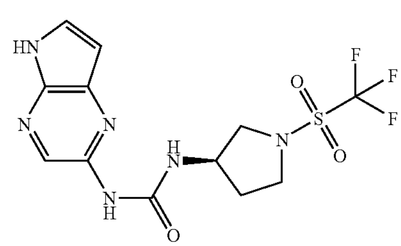 | |

TABLE I-continued

| COMPOUND | SYSTEMATIC NAME | STRUCTURE | MS Data (M + 1) |
|---|---|---|---|
| I-105 | 1-(1-Methanesulfonyl-piperidin-2-ylmethyl)-3-(5H-pyrrolo[2,3-b]pyrazin-2-yl)-urea | 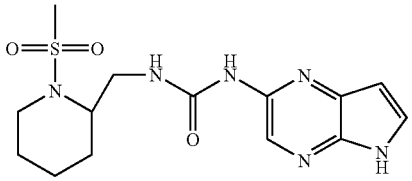 | |
| I-106 | 1-[2-(1-Methanesulfonyl-pyrrolidin-2-yl)-ethyl]-3-(5H-pyrrolo[2,3-b]pyrazin-2-yl)-urea | 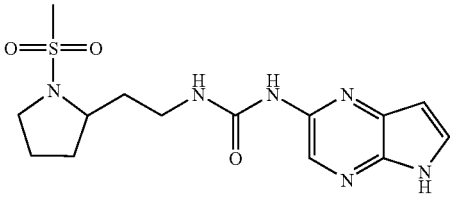 | |
| I-107 | 2-{2-[3-(5H-Pyrrolo[2,3-b[9 pyrazin-2-yl)-ureido]-ethyl}-pyrrolidine-1-carboxylic acid methyl ester | 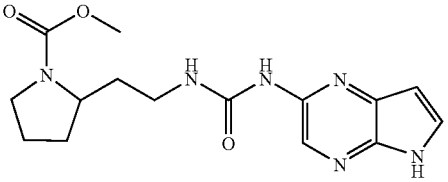 | |
| I-108 | 4-[3-(5H-Pyrrolo[2,3-b]pyrazin-2-yl)-ureido]-azepane-1-carboxylic acid methyl ester | 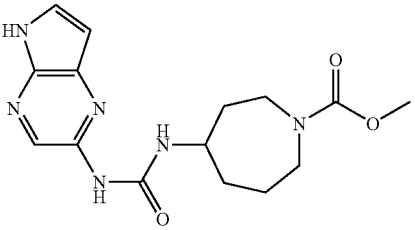 | |
| I-109 | 1-(1-Methanesulfonyl-azepan-4-yl)-3-(5H-pyrrolo[2,3-b]pyrazin-2-yl)-urea | 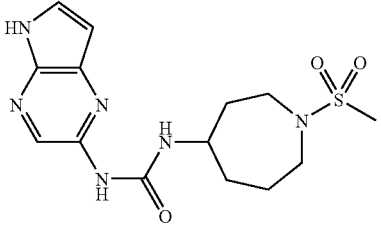 | |
| I-110 | 1-[2-(1-Methanesulfonyl-piperidin-3-yl)-ethyl]-3-(5H-pyrrolo[2,3-b]pyrazin-2-yl)-urea | 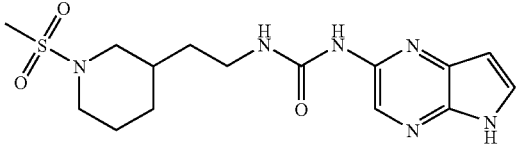 | |
| I-111 | 3-{2-[3-(5H-Pyrrolo[2,3-b]pyrazin-2-yl)-ureido]-ethyl}-piperidine-1-carboxylic acid methyl ester | 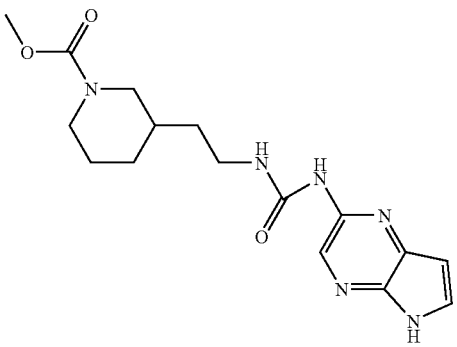 | |

TABLE I-continued

| COMPOUND | SYSTEMATIC NAME | STRUCTURE | MS Data (M + 1) |
|---|---|---|---|
| I-112 | 1-(1-Acetyl-azepan-4-yl)-3-(5H-pyrrolo[2,3-b]pyrazin-2-yl)-urea | 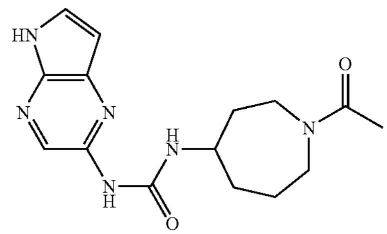 | |
| I-113 | 1-[1-(3-Methyl-butane-1-sulfonyl)-piperidin-3-yl]-3-(5H-pyrrolo[2,3-b]pyrazin-2-yl)-urea | 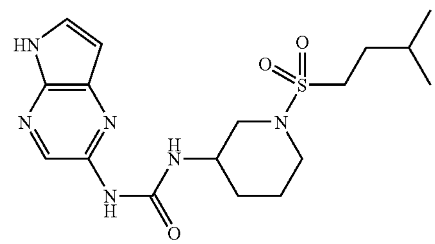 | |
| I-114 | 1-(5H-Pyrrolo[2,3-b]pyrazin-2-yl)-3-[1-(3,3,3-trifluoro-propane-1-sulfonyl)-piperidin-3-yl]-urea | 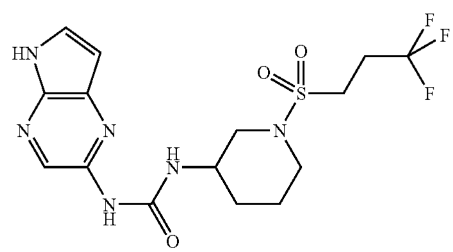 | |
| I-115 | 1-(5H-Pyrrolo[2,3-b]pyrazin-2-yl)-3-[(R)-1-(3,3,3-trifluoro-propane-1-sulfonyl)-pyrrolidin-3-yl]-urea | 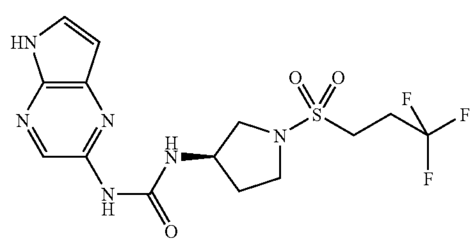 | |
| I-116 | 1-((3R,5R)-1-Acetyl-5-methyl-piperidin-3-yl)-3-(5H-pyrrolo[2,3-b]pyrazin-2-yl)-urea | 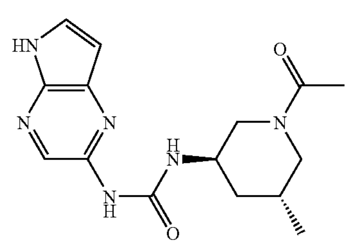 | |
| I-117 | 1-[(S)-1-(2,2-Dimethyl-propane-1-sulfonyl)-piperidin-3-yl]-3-(5H-pyrrolo[2,3-b]pyrazin-2-yl)-urea | 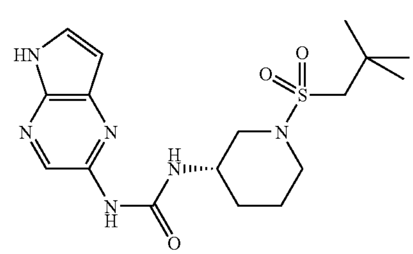 | |

TABLE I-continued

| COMPOUND | SYSTEMATIC NAME | STRUCTURE | MS Data (M + 1) |
|---|---|---|---|
| I-118 | 1-[(S)-1-(2-Methoxy-ethanesulfonyl)-piperidin-3-yl]-3-(5H-pyrrolo[2,3-b]pyrazin-2-yl)-urea | 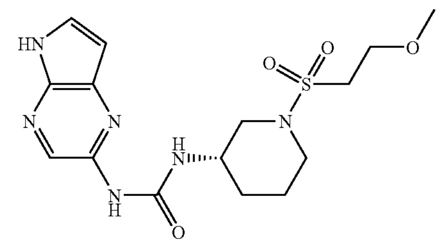 | |
| I-119 | 1-(1-Methanesulfonyl-5-methyl-azepan-4-yl)-3-(5H-pyrrolo[2,3-b]pyrazin-2-yl)-urea | 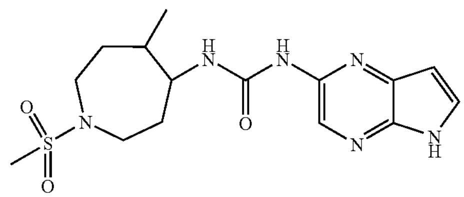 | |
| I-120 | 4-Methyl-5-[3-(5H-pyrrolo[2,3-b]pyrazin-2-yl)-ureido]-azepane-1-carboxylic acid methyl ester | 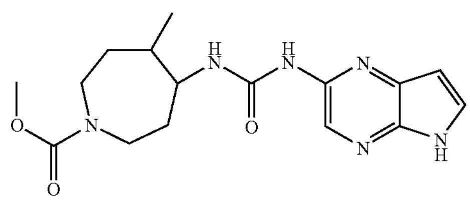 | |
| I-121 | 1-(1-Acetyl-piperidin-2-ylmethyl)-3-(5H-pyrrolo[2,3-b]pyrazin-2-yl)-urea | 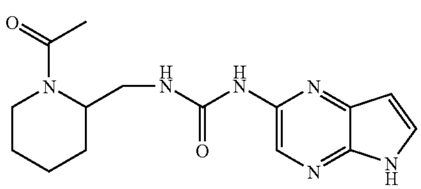 | |
| I-122 | 2-{[3-(5H-Pyrrolo[2,3-b]pyrazin-2-yl)-ureido]-methyl}-piperidine-1-carboxylic acid methyl ester | 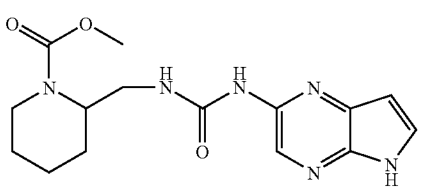 | |
| I-123 | 1-[2-(1-Acetyl-piperidin-2-yl)-ethyl]-3-(5H-pyrrolo[2,3-b]pyrazin-2-yl)-urea | 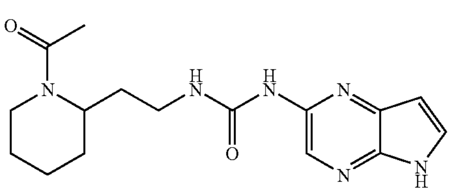 | |
| I-124 | 2-{2-[3-(5H-Pyrrolo[2,3-b]pyrazin-2-yl)-ureido]-ethyl}-piperidine-1-carboxylic acid methyl ester | 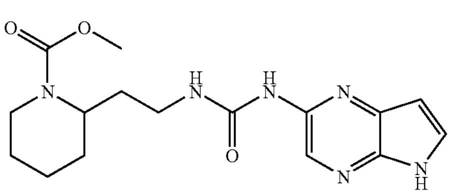 | |

TABLE I-continued

| COMPOUND | SYSTEMATIC NAME | STRUCTURE | MS Data (M + 1) |
|---|---|---|---|
| I-125 | 1-(1-Acetyl-piperidin-4-ylmethyl)-3-(5H-pyrrolo[2,3-b]pyrazin-2-yl)-urea | 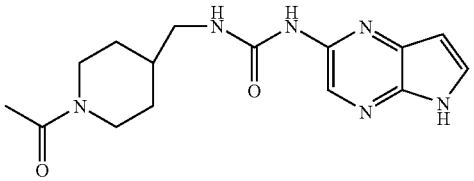 | |
| I-126 | 1-(1-Methanesulfonyl-piperidin-4-ylmethyl)-3-(5H-pyrrolo[2,3-b]pyrazin-2-yl)-urea | 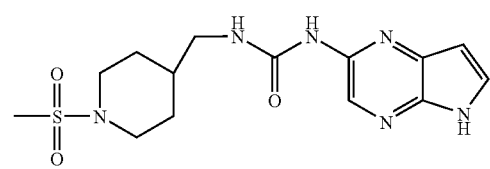 | |
| I-127 | 1-((1S,3S)-3-Methoxymethyl-cyclohexyl)-3-(5H-pyrrolo[2,3-b]pyrazin-2-yl)-urea | 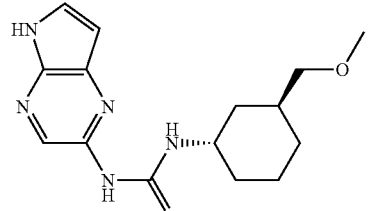 | |
| I-128 | 1-(1-Acetyl-5-methyl-azepan-4-yl)-3-(5H-pyrrolo[2,3-b]pyrazin-2-yl)-urea | 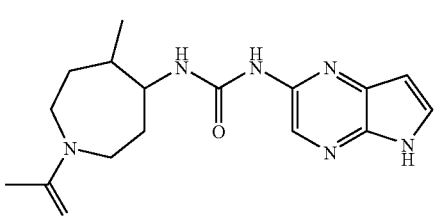 | |
| I-129 | 1-[2-(1-Methanesulfonyl-piperidin-2-yl)-ethyl]-3-(5H-pyrrolo[2,3-b]pyrazin-2-yl)-urea | 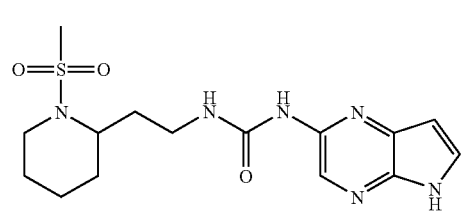 | |
| I-130 | 1-[2-(1-Acetyl-piperidin-3-yl)-ethyl]-3-(5H-pyrrolo[2,3-b]pyrazin-2-yl)-urea | 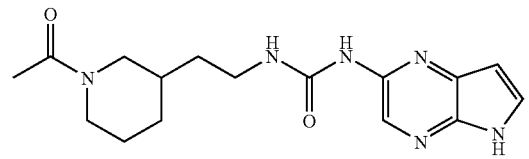 | |
| I-131 | 4-{[3-(5H-Pyrrolo[2,3-b]pyrazin-2-yl)-ureido]-methyl}-piperidine-1-carboxylic acid methyl ester | 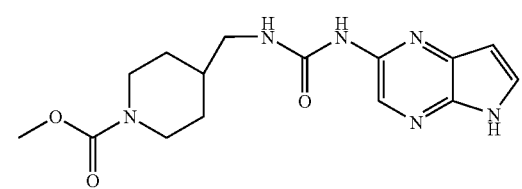 | |

TABLE I-continued

| COMPOUND | SYSTEMATIC NAME | STRUCTURE | MS Data (M + 1) |
|---|---|---|---|
| I-132 | 2-{[3-(5H-Pyrrolo[2,3-b]pyrazin-2-yl)-ureido]-methyl}-pyrrolidine-1-carboxylic acid methyl ester | 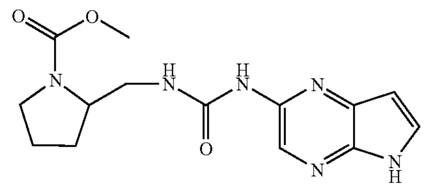 | |
| I-133 | 1-(5H-Pyrrolo[2,3-b]pyrazin-2-yl)-3-[(S)-1-(1-trifluoromethyl-cyclopropylmethane-sulfonyl)-piperidin-3-yl]-urea | 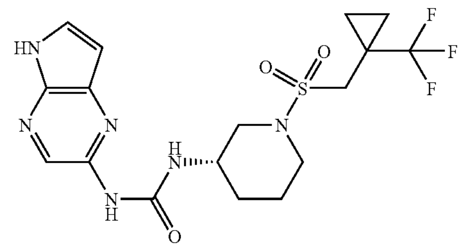 | |
| I-134 | 1-Cyclohexyl-3-(7-isopropyl-5H-pyrrolo[2,3-b]pyrazin-2-yl)-urea | 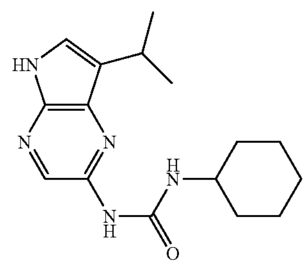 | |
| I-135 | 1-[(S)-1-(3-Methyl-oxetan-3-ylmethanesulfonyl)-piperidin-3-yl]-3-(5H-pyrrolo[2,3-b]pyrazin-2-yl)-urea | 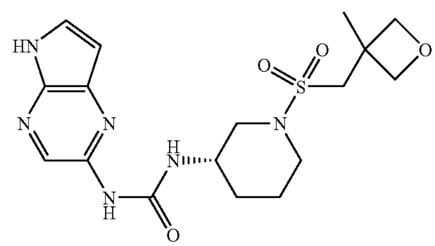 | |
| I-136 | 1-(1-Acetyl-piperidin-3-ylmethyl)-3-(5H-pyrrolo[2,3-b]pyrazin-2-yl)-urea | 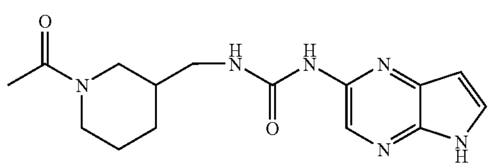 | |
| I-137 | 1-(1-Methanesulfonyl-piperidin-3-ylmethyl)-3-(5H-pyrrolo[2,3-b]pyrazin-2-yl)-urea | 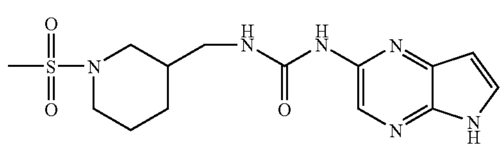 | |
| I-138 | 1-[2-(1-Acetyl-piperidin-4-yl)-ethyl]-3-(5H-pyrrolo[2,3-b]pyrazin-2-yl)-urea | 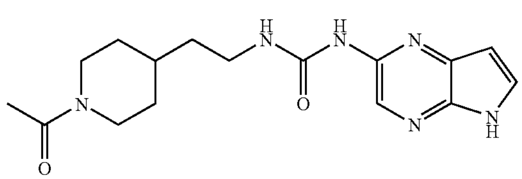 | |

TABLE I-continued

| COMPOUND | SYSTEMATIC NAME | STRUCTURE | MS Data (M + 1) |
|---|---|---|---|
| I-139 | 1-[2-(1-Acetyl-pyrrolidin-2-yl)-ethyl]-3-(5H-pyrrolo[2,3-b]pyrazin-2-yl)-urea | 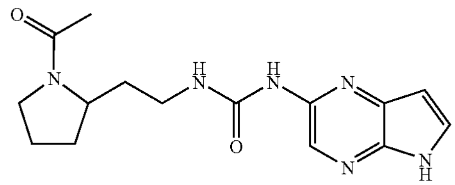 | |
| I-140 | 1-[1-(Propane-1-sulfonyl)-pyrrolidin-2-ylmethyl]-3-(5H-pyrrolo[2,3-b]pyrazin-2-yl)-urea | 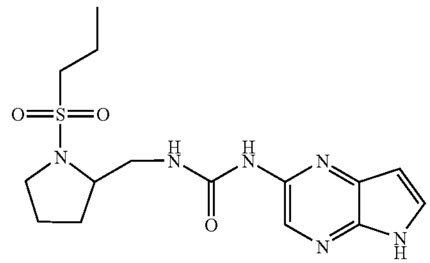 | |
| I-141 | 1-[2-(1-Methanesulfonyl-piperidin-4-yl)-ethyl]-3-(5H-pyrrolo[2,3-b]pyrazin-2-yl)-urea | 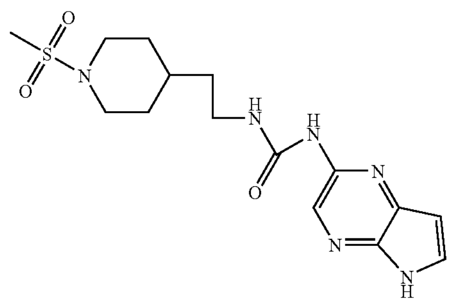 | |
| I-142 | 4-{2-[3-(5H-Pyrrolo[2,3-b]pyrazin-2-yl)-ureido]-ethyl}-piperidine-1-carboxylic acid methyl ester | 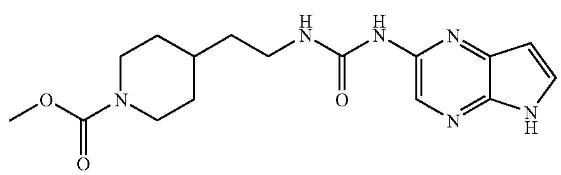 | |
| I-143 | 1-(1-Ethanesulfonyl-pyrrolidin-2-ylmethyl)-3-(5H-pyrrolo[2,3-b]pyrazin-2-yl)-urea | 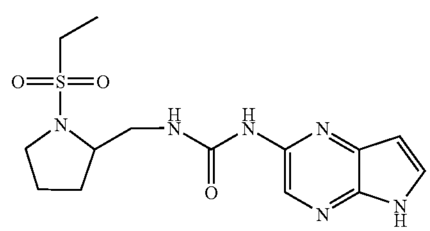 | |
| I-144 | 1-[1-(Propane-2-sulfonyl)-pyrrolidin-2-ylmethyl]-3-(5H-pyrrolo[2,3-b]pyrazin-2-yl)-urea | 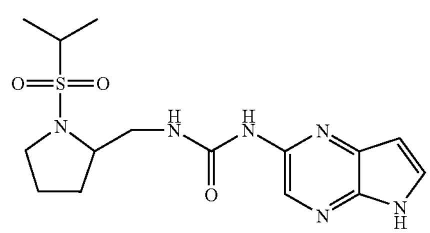 | |
| I-145 | 3-{[3-(5H-Pyrrolo[2,3-b]pyrazin-2-yl)-ureido]-methyl}-piperidine-1-carboxylic acid methyl ester | 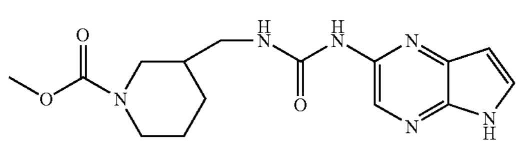 | |

TABLE I-continued

| COMPOUND | SYSTEMATIC NAME | STRUCTURE | MS Data (M + 1) |
|---|---|---|---|
| I-146 | 1-(1-Methanesulfonyl-pyrrolidin-3-ylmethyl)-3-(5H-pyrrolo[2,3-b]pyrazin-2-yl)-urea | 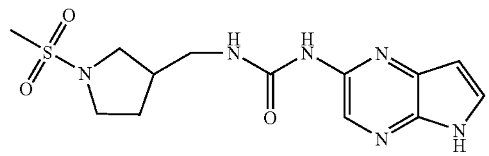 | |
| I-147 | 1-(1-Acetyl-pyrrolidin-2-ylmethyl)-3-(5H-pyrrolo[2,3-b]pyrazin-2-yl)-urea | 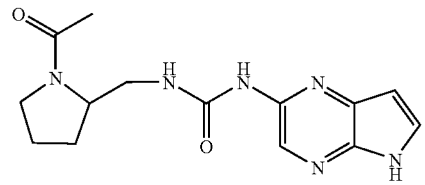 | |
| I-148 | 1-[1-(2-Methyl-propane-1-sulfonyl)-pyrrolidin-2-ylmethyl]-3-(5H-pyrrolo[2,3-b]pyrazin-2-yl)-urea | 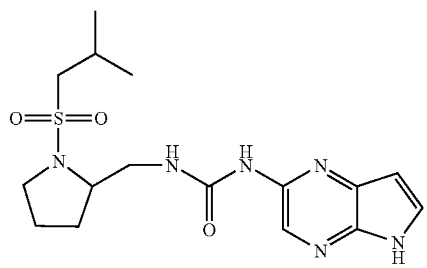 | |
| I-149 | 1-(5H-Pyrrolo[2,3-b]pyrazin-2-yl)-3-[1-(2,2,2-trifluoro-ethyl)-piperidin-2-ylmethyl]-urea | 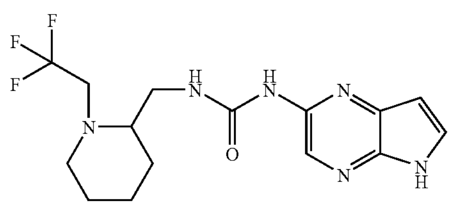 | |
| I-150 | 1-(5H-Pyrrolo[2,3-b]pyrazin-2-yl)-3-[1-(2,2,2-trifluoro-ethyl)-piperidin-4-ylmethyl]-urea | 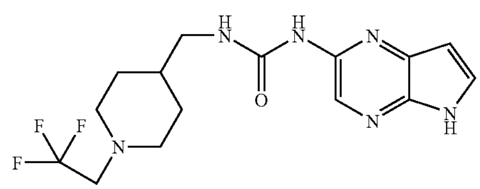 | |
| I-151 | (1S,3S)-3-[3-(5H-Pyrrolo[2,3-b]pyrazin-2-yl)-ureido]-cyclohexane-carboxylic acid dimethylamide | 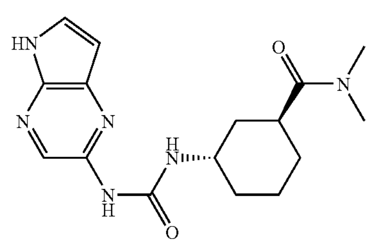 | |
| I-152 | 1-(5H-Pyrrolo[2,3-b]pyrazin-2-yl)-3-[1-(2,2,2-trifluoro-ethyl)-piperidin-3-ylmethyl]-urea | 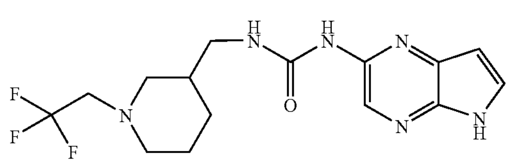 | |
| I-153 | 1-(5H-Pyrrolo[2,3-b]pyrazin-2-yl)-3-{2-[1-(2,2,2-trifluoro-ethyl)-piperidin-3-yl]-ethyl}-urea | 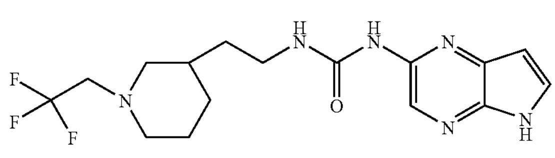 | |

TABLE I-continued

| COMPOUND | SYSTEMATIC NAME | STRUCTURE | MS Data (M + 1) |
|---|---|---|---|
| I-154 | 3-{[3-(5H-Pyrrolo[2,3-b]pyrazin-2-yl)-ureido]-methyl}-pyrrolidine-1-carboxylic acid methyl ester | 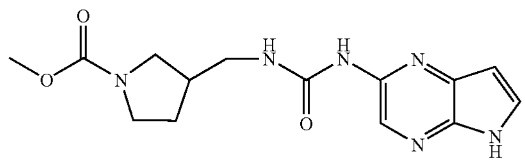 | |
| I-155 | 1-(5H-Pyrrolo[2,3-b]pyrazin-2-yl)-3-{2-[1-(2,2,2-trifluoro-ethyl)-pyrrolidin-2-yl]-ethyl}-urea | 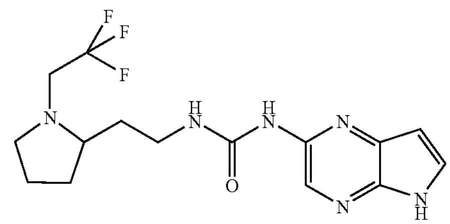 | |
| I-156 | (1S,3S)-3-[3-(5H-Pyrrolo[2,3-b]pyrazin-2-yl)-ureido]-cyclopentane-carboxylic acid methylamide | 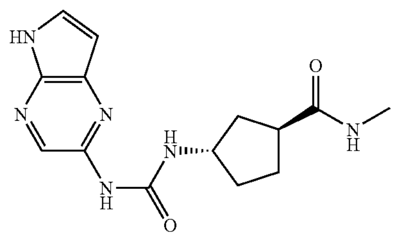 | |
| I-157 | (1S,3S)-3-[3-(5H-Pyrrolo[2,3-b]pyrazin-2-yl)-ureido]-cyclopentane-carboxylic acid ethylamide | 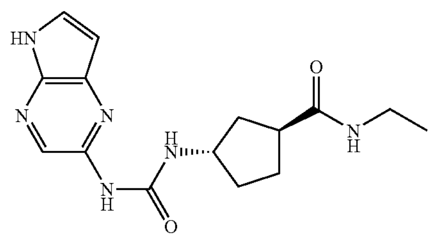 | |

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLES

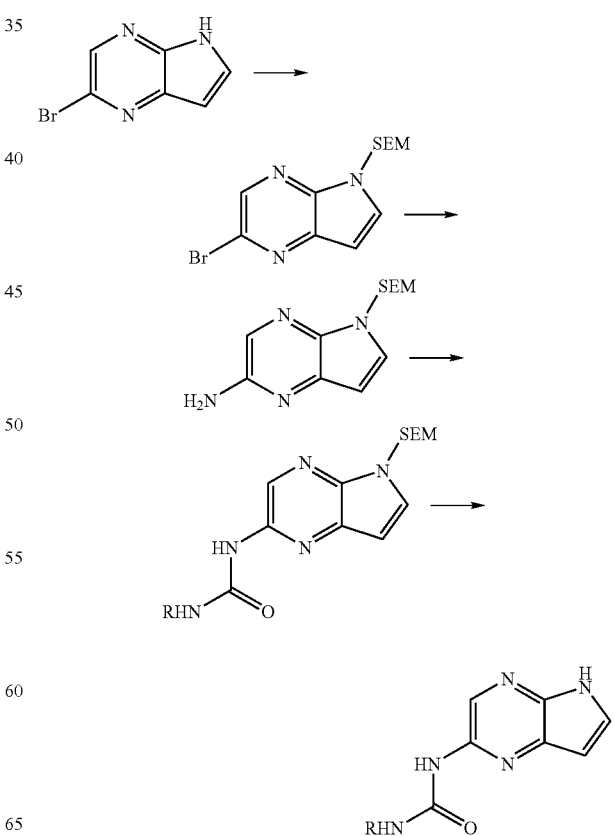

Example 1

Representative Example of Synthesis of Compounds in Table I

Step 1.

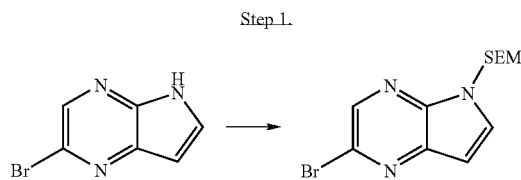

Sodium hydride (60% in mineral oil, 0.800 g, 20 mmol) was washed with hexane then taken up in 30 mL of N,N-dimethylformamide and cooled to 0-5° C. 2-Bromo-5H-pyrrolo[2,3-b]pyrazine (3.0 g, 15 mmol) was added, then SEMCl (3.5 mL, 20 mmol). The mixture was stirred at room temperature for 3 h, then concentrated. Column chromatography afforded 3.25 g (65%) of 2-bromo-5-(2-trimethylsilanyl-ethoxymethyl)-5H-pyrrolo[2,3-b]pyrazine.

Step 2.

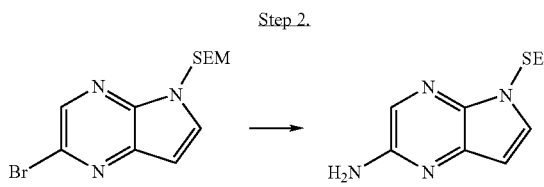

A mixture of 2-bromo-5-(2-trimethylsilanyl-ethoxymethyl)-5H-pyrrolo[2,3-b]pyrazine (3.25 g, 10 mmol) sodium t-butoxide (0.600 g, 6.25 mmol), and BINAP (0.170 g, 0.27 mmol) in 120 mL of toluene was purged with nitrogen for ca. 20 min. Pd$_2$(dba)$_3$ (0.080 g, 0.077 mmol) and benzophenone imine (2.16 mL, 12.9 mmol) were added, and the mixture was stirred at 130° C. for 12 h. The mixture was filtered through Celite and concentrated. The resulting residue was dissolved in 50 mL of methanol. Sodium acetate (4.93 g, 36 mmol) and hydroxylamine hydrochloride (2.09 g, 30 mmol) were added, and the mixture was stirred for 45 min. then concentrated. The resulting residue was partitioned between a 0.1 M NaOH solution and dichloromethane, and the organic layer was dried over Na$_2$SO$_4$, filtered and concentrated to a residue. Column chromatography afforded 3.0 g (75%) of 5-(2-trimethylsilanyl-ethoxymethyl)-5H-pyrrolo[2,3-b]pyrazin-2-ylamine.

Step 3.

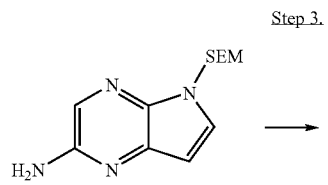

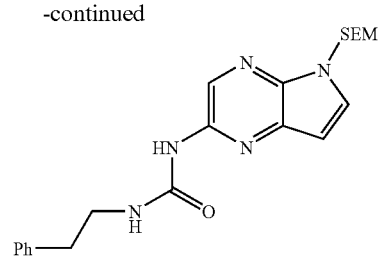

A solution of 5-(2-trimethylsilanyl-ethoxymethyl)-5H-pyrrolo[2,3-b]pyrazin-2-ylamine (0.260 g, 0.98 mmol) in 15 mL of dichloromethane was cooled to −30° C. Phenethyl isocyanate (0.21 g, 1.5 mmol) was added, and the resulting solution was stirred at room temperature for 14 h, then concentrated to a residue. Column chromatography afforded 0.220 g (55%) of 1-phenethyl-3-[5-(2-trimethylsilanyl-ethoxymethyl)-5H-pyrrolo[2,3-b]pyrazin-2-yl]-urea.

Step 4.

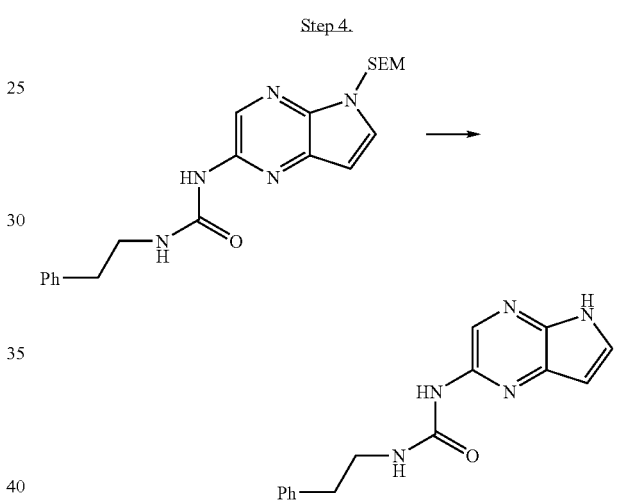

A solution of 1-phenethyl-3-[5-(2-trimethylsilanyl-ethoxymethyl)-5H-pyrrolo[2,3-b]pyrazin-2-yl]-urea (0.22 g, 0.53 mmol), tetrabutylammonium fluoride (1 M in THF, 3 mL, 3 mmol) and ethylene diamine (0.3 mL, 5 mmol) in 5 mL of N,N-dimethylformamide was stirred at 80° C. for 14 h, then concentrated. The resulting residue was triturated with methanol then ether to afford 0.040 g (26%) of 1-phenethyl-3-(5H-pyrrolo[2,3-b]pyrazin-2-yl)-urea as an off-white solid.

The following compounds were prepared in a similar fashion as for 1-phenethyl-3-(5H-pyrrolo[2,3-b]pyrazin-2-yl)-urea:

1-Cyclohexyl-3-(5H-pyrrolo[2,3-b]pyrazin-2-yl)-urea
1-Phenyl-3-(5H-pyrrolo[2,3-b]pyrazin-2-yl)-urea
1-Cyclopentyl-3-(5H-pyrrolo[2,3-b]pyrazin-2-yl)-urea
1-Cycloheptyl-3-(5H-pyrrolo[2,3-b]pyrazin-2-yl)-urea
1-Benzyl-3-(5H-pyrrolo[2,3-b]pyrazin-2-yl)-urea
1-Cyclohexylmethyl-3-(5H-pyrrolo[2,3-b]pyrazin-2-yl)-urea
1-(2-Chloro-phenyl)-3-(5H-pyrrolo[2,3-b]pyrazin-2-yl)-urea
1-((R)-1-Phenyl-ethyl)-3-(5H-pyrrolo[2,3-b]pyrazin-2-yl)-urea
1-((S)-1-Phenyl-ethyl)-3-(5H-pyrrolo[2,3-b]pyrazin-2-yl)-urea
1-(5H-Pyrrolo[2,3-b]pyrazin-2-yl)-3-o-tolyl-urea 1-(5H-Pyrrolo[2,3-b]pyrazin-2-yl)-3-(2-trifluoromethyl-phenyl)-urea 1-Ethyl-3-(5H-pyrrolo[2,3-b]pyrazin-2-yl)-urea 1-tert-Butyl-3-(5H-pyrrolo[2,3-b]pyrazin-2-yl)-urea 1-Isopropyl-3-(5H-pyrrolo[2,3-b]pyrazin-2-yl)-urea Example 2

Step 1.

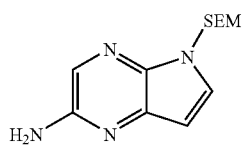

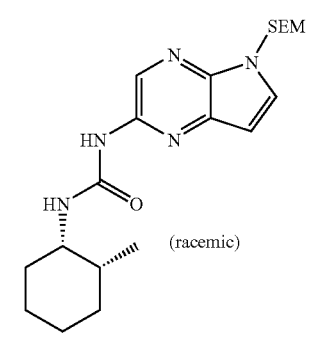

Phosgene (ca. 20% in toluene, 0.9 mL) was added to a 0° C. solution of 5-(2-trimethylsilanyl-ethoxymethyl)-5H-pyrrolo[2,3-b]pyrazin-2-ylamine (0.300 g, 1.1 mmol) and diisopropylethylamine (0.6 mL, 3.4 mmol) in 10 mL of dichloromethane. The mixture was stirred for 10 min., then cis-2-methylcyclohexylamine hydrochloride (prepared as in Knupp, G. Chem. Ber. 1984, 117(6), 2076-98, using racemic α-methylbenzylamine) (0.249 g, 1.6 mmol) was added as a solution in 2 mL of dichloromethane with a few added drops of diisopropylethylamine. The mixture was stirred for 40 min., then concentrated to a residue. Column chromatography afforded 0.25 g (55%) of 1-(cis-2-methyl-cyclohexyl)-3-[5-(2-trimethylsilanyl-ethoxymethyl)-5H-pyrrolo[2,3-b]pyrazin-2-yl]-urea.

Step 2.

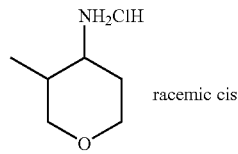

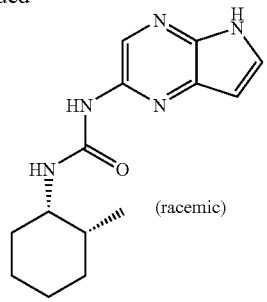

A mixture of 1-(cis-2-methyl-cyclohexyl)-3-[5-(2-trimethylsilanyl-ethoxymethyl)-5H-pyrrolo[2,3-b]pyrazin-2-yl]-urea (0.3 g, 0.7 mmol), tetrabutyl ammonium fluoride (1 M in THF, 4.6 mL, 4.6 mmol) and ethylene diamine (0.46 mL, 4.2 mmol) in 5 mL of N,N-dimethylformamide was stirred at 80° C. for 20 h, then concentrated. The resulting residue was triturated in methanol, and solid was isolated by filtration, washing with ether, and dried to afford 0.060 g (30%) of 1-(cis-2-methyl-cyclohexyl)-3-(5H-pyrrolo[2,3-b]pyrazin-2-yl)-urea as an off-white solid.

Example 3

Synthesis of racemic cis 3-methyl-tetrahydro-pyran-4-ylamine hydrochloride

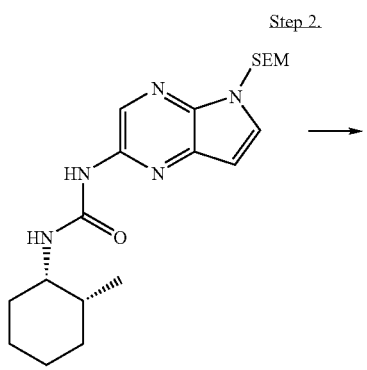

Step 1: In an oven dried flask equipped with a thermometer, tetrahydro-4H-pyran-4-one (6 mL, 64.97 mmol) was dissolved in THF (150 mL) and cooled down to −65° C. LDA (2M, 39 mL, 78 mmol) was added slowly, keeping the temperature below −60° C. After the addition was complete stirring was continued for one hour at −50° C. Iodomethane (16 mL, 25.7 mmol) was added and the reaction mixture was allowed to warm up overnight. The reaction was quenched with saturated aqueous $NH_4Cl$. The aqueous layer was extracted with $Et_2O$. The combined organic layers were washed with brine, dried ($Na_2SO_4$), filtered and mostly evaporated (30° C. bath, 100 mbar). The remaining material was purified by $SiO_2$ chromatography (200 g $SiO_2$, hexanes/$Et_2O$ 0 to 30% $Et_2O$) to give 1 g of racemic 3-methyl-tetrahydro-pyran-4-one as a light yellow liquid (13% yield).

Step 2: Racemic 3-methyl-tetrahydro-pyran-4-one (1 g, 8.761 mmol) was dissolved in DCM. Benzylamine (1.5 mL, 13.75 mmol) and sodium triacetoxyborohydride (95%, 3.3 g, 14.89 mmol) were added and the resulting suspension was stirred at RT overnight. The reaction mixture was washed with saturated aqueous $NaHCO_3$. The aqueous layer was extracted with DCM. The combined organic layers were washed with brine, dried ($Na_2SO_4$), filtered and evaporated. The remaining yellow liquid was purified by $SiO_2$ chromatography (120 g $SiO_2$, DCM/(DCM:MeOH:$NH_4OH$ 60:10:1) 92% DCM) to give 1.8 g of racemic cis benzyl-(3-methyl-tetrahydro-pyran-4-yl)-amine as a light yellow oil (>95% yield).

Step 3: Racemic cis benzyl-(3-methyl-tetrahydro-pyran-4-yl)-amine (1.8 g, 8.768 mmol) was dissolved in 3M HCl (4.4 mL, 13.2 mmol). Pd(OH)$_2$ 20 wt % (0.6 g) and EtOH (50 mL) were added and the reaction mixture was hydrogenated in a Parr shaker at 55 psi H$_2$ over the weekend. The palladium was filtered off. HCl 4M in dioxane was added and the solvent was evaporated. The remaining green oil was adsorbed onto SiO$_2$ and purified by SiO$_2$ chromatography (100 g SiO$_2$, DCM/(DCM:MeOH:NH$_4$OH 60:10:1) 100-55% DCM). The fractions containing the product were combined and HCl 4M in dioxane was added. NH$_4$Cl crashed out. The solvent was evaporated. The remaining white semi-solid was taken up in MeOH/Et$_2$O and the salt was filtered off and washed with Et$_2$O. The filtrate was evaporated. The remaining oil was taken up in DCM and was evaporated again to obtain 0.58 of racemic cis 3-methyl-tetrahydro-pyran-4-ylamine hydrochloride as a light yellow solid (43% yield).

Racemic cis 1-(4-amino-3-methyl-piperidin-1-yl)-ethanone was prepared in the same manner from racemic 1-acetyl-3-methyl-piperidin-4-one. In this instance, 1 atm H$_2$ was used instead of 55 psi, and the HCl treatment was omitted.

Racemic cis 1-methanesulfonyl-3-methyl-piperidin-4-ylamine was prepared in the same manner from racemic benzyl-(1-methanesulfonyl-3-methyl-piperidin-4-yl)-amine. In this instance, 1 atm H$_2$ was used instead of 55 psi, and the HCl treatment was omitted.

Racemic cis 4-benzylamino-3-methyl-piperidine-1-carboxylic acid methyl ester was prepared in the same manner from racemic 4-benzylamino-3-methyl-piperidine-1-carboxylic acid methyl ester. In this instance, 1 atm H$_2$ was used instead of 55 psi, and the HCl treatment was omitted.

Racemic cis 2-methyl-cycloheptylamine was prepared in the same manner from racemic cis benzyl-(2-methyl-cycloheptyl)-amine. In this instance, 1 atm H$_2$ was used instead of 55 psi, and the HCl treatment was omitted.

Racemic cis 1-(4-amino-5-methyl-azepan-1-yl)-ethanone was prepared in the same manner from racemic cis 1-(4-benzylamino-5-methyl-azepan-1-yl)-ethanone. In this instance, 1 atm H$_2$ was used instead of 55 psi, Pd/C was used instead of Pd(OH)$_2$/C, EtOAc was used instead of EtOH, and the HCl treatment was omitted.

Racemic cis 4-amino-5-methyl-azepane-1-carboxylic acid tert-butyl ester was prepared in the same manner from racemic cis 4-benzylamino-5-methyl-azepane-1-carboxylic acid tert-butyl ester. In this instance, 1 atm H$_2$ was used instead of 55 psi, Pd/C was used instead of Pd(OH)$_2$/C, EtOAc was used instead of EtOH, and the HCl treatment was omitted.

Example 4

Synthesis of racemic cis 2-ethyl-cyclohexylamine

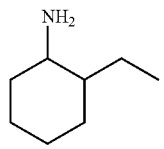

A solution of compound 2-ethyl-phenylamine in absolute ethanol was purged thoroughly with argon for 20 min. 5% Rh on alumina (100% w/w) was added and the reaction mixture was subjected to hydrogenation at 60° C. and 100 psi for 20 h. TLC (20% hexanes/EtOAc 20% EtOAc) showed complete consumption of starting material. The reaction mixture was filtered through celite and the filtrate was evaporated to give to give racemic cis 2-ethyl-cyclohexylamine (40% yield) which was used crude in the next step.

Racemic cis 2-isopropyl-cyclohexylamine was prepared in the same manner using 2-isopropyl-phenylamine as starting material.

Example 5

Synthesis of (1R,2S)-2-methyl-cyclohexylamine hydrochloride

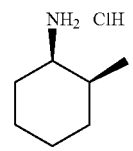

Step 1: 2-Methylcyclohexanone (4 mL, 32.98 mmol) and (R)-1-phenylethylamine (4.4 mL, 34.63 mmol) were dissolved in benzene (25 mL) and stirred at reflux with continuous removal of H$_2$O for 3 hours. The reaction mixture was cooled to RT and the solvent was evaporated. The imine intermediate was dissolved in DCM (150 mL) and cooled to 0° C. Sodium triacetoxyborohydride (95%, 8.83 g, 39.58 mmol) and acetic acid (2.1 mL, 36.3 mmol) were added. After about 20 minutes, the ice bath was removed and the suspension was stirred at RT overnight. The reaction mixture was cooled to 0° C. and aqueous saturated NaHCO$_3$ was added. The layers were separated and the aqueous layer was extracted with DCM. The organic layers were combined, washed once more with NaHCO$_3$, dried (Na$_2$SO$_4$), filtered and evaporated. 6.5 g of yellow oil were purified by SiO$_2$ chromatography (400 g SiO$_2$, DCM/(DCM:MeOH:NH$_4$OH 60:10:1) 87% magic DCM). By TLC only one major spot is visible. The first and last fractions were evaporated and NMR showed the trans isomer came off in the first fractions. The fractions were evaporated 3 at a time until 0.66 g of cis (2-methyl-cyclohexyl)-((R)-1-phenyl-ethyl)-amine as white soft crystals were obtained. NMR showed the presence of about 5% of the trans isomer. Another unidentified impurity could not be separated off.

Racemic cis 1-(4-benzylamino-3-methyl-piperidin-1-yl)-ethanone was prepared in the same manner from racemic 1-acetyl-3-methyl-piperidin-4-one. In this instance, benzylamine was used instead of (R)-1-phenylethylamine.

Racemic cis benzyl-(1-methanesulfonyl-3-methyl-piperidin-4-yl)-amine was prepared in the same manner from racemic 1-methanesulfonyl-3-methyl-piperidin-4-one. In this instance, benzylamine was used instead of (R)-1-phenylethylamine.

Racemic cis 4-benzylamino-3-methyl-piperidine-1-carboxylic acid methyl ester was prepared in the same manner from racemic 3-methyl-4-oxo-piperidine-1-carboxylic acid methyl ester. In this instance, benzylamine was used instead of (R)-1-phenylethylamine.

Racemic cis benzyl-(2-methyl-cycloheptyl)-amine was prepared in the same manner from racemic 2-methyl-cycloheptanone. In this instance, benzylamine was used instead of (R)-1-phenylethylamine.

Racemic 1-(4-benzylamino-5-methyl-azepan-1-yl)-ethanone was prepared in the same manner from racemic 1-acetyl-5-methyl-azepan-4-one. In this instance, benzylamine was used instead of (R)-1-phenylethylamine.

Racemic 4-benzylamino-5-methyl-azepane-1-carboxylic acid tert-butyl ester was prepared in the same manner from racemic 4-methyl-5-oxo-azepane-1-carboxylic acid tert-butyl ester. In this instance, benzylamine was used instead of (R)-1-phenylethylamine.

Step 2: To cis (2-methyl-cyclohexyl)-((R)-1-phenylethyl)-amine (0.65 g, 2.99 mmol) Pd(OH)$_2$ on carbon 20 wt % (0.3 g) and EtOH (10 mL) were added and the reaction mixture stirred at RT under 1 atm of H$_2$ overnight. The palladium was filtered off and the solvent was evaporated (be careful, the free amine sublimes). The remaining material was purified by SiO$_2$ chromatography (40 g SiO$_2$, DCM/(DCM:MeOH: NH$_4$OH 60:10:1) 100-71% DCM). TLC shows only one major spot. Ten fractions were evaporated at a time. After running NMR the first 20 were combined and evaporated. The residue was dissolved in DCM and treated with 4M HCl in dioxane. The solvent was evaporated and the remaining solid was dried under high vacuum to give 0.075 g of (1R,2S)-2-methyl-cyclohexylamine hydrochloride as an off-white solid (16% yield). NMR showed the presence of about 5% of the trans isomer.

Example 6

Synthesis of (1S,2R)-2-methyl-cyclohexylamine hydrochloride

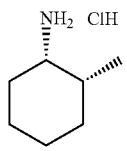

Step 1: 2-Methylcyclohexanone (4 mL, 32.98 mmol) and (S)-1-phenylethylamine (4.4 mL, 34.63 mmol) were dissolved in benzene (25 mL) and stirred at reflux with continuous removal of H$_2$O for 3 hours. The reaction mixture was allowed to cool to RT and the solvent was evaporated. The imine intermediate was dissolved in DCM (150 mL) and was cooled down to 0° C. Sodium triacetoxyborohydride (95%, 8.83 g, 39.58 mmol) and acetic acid (2.1 mL, 36.3 mmol) were added. After about 20 minutes, the ice bath was removed and the suspension stirred at RT overnight. The reaction mixture was cooled to 0° C. and saturated aqueous NaHCO$_3$ was added. The layers were separated and the aqueous layer was extracted with DCM. The combined organic layers were washed once more with saturated aqueous NaHCO$_3$, dried (Na$_2$SO$_4$), filtered and evaporated. 6.4 g of yellow oil were purified by SiO$_2$ chromatography (400 g SiO$_2$, DCM/(DCM: MeOH:NH$_4$OH 60:10:1) 87% DCM). By TLC only one major spot is visible. The first and last fractions were evaporated and NMR showed the trans came off in the first fractions. The fractions were evaporated three at a time until 1 g of (2-methyl-cyclohexyl)-((S)-1-phenyl-ethyl)-amine was obtained as a light yellow oil. NMR showed the presence of about 5% of the trans isomer. The other impurities could not be separated off.

Step 2: To cis (2-methyl-cyclohexyl)-((S)-1-phenyl-ethyl)-amine (1 g, 4.601 mmol) Pd(OH)$_2$ on carbon 20 wt % (0.5 g) and EtOH (20 mL) were added and the reaction mixture was stirred at RT under 1 atm of H$_2$ overnight. The palladium was filtered off and the solvent was evaporated. Be careful, the free amine sublimes. The remaining pale brown oil was purified by SiO$_2$ chromatography (50 g SiO$_2$, DCM/(DCM: MeOH:NH$_4$OH 60:10:1) 100-65% DCM). The fractions containing the product were evaporated. The residue was dissolved in DCM and treated with 4M HCl in dioxane. The solvent was evaporated and the remaining solid was dried under high vacuum to give 0.26 g of (1S,2R)-2-methyl-cyclohexylamine hydrochloride as off-white solid (37% yield). NMR showed the presence of about 5% of the trans isomer.

Example 7

Synthesis of 3,3-dimethyl-cyclohexylamine hydrochloride

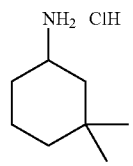

Step 1: 3,3-Dimethylcyclohexanone (3 g, 23.77 mmol) and benzylamine (2.73 mL, 24.96 mmol) were dissolved in benzene (20 mL) and stirred at reflux with continuous removal of H$_2$O for 3 hours. The reaction mixture was allowed to cool to RT and the solvent was evaporated. The imine intermediate was dissolved in DCM (100 mL) and cooled to 0° C. Sodium triacetoxyborohydride (95%, 6.36 g, 28.53 mmol) and acetic acid (1.5 mL, 26.15 mmol) were added. After about 20 minutes the ice bath was removed, and the suspension stirred at RT overnight. The reaction mixture was cooled to 0° C. and saturated aqueous NaHCO$_3$ was added. The layers were separated and the aqueous layer was extracted with DCM. The combined organic layers were washed once more with saturated aqueous NaHCO$_3$, dried (Na$_2$SO$_4$), filtered and evaporated. The remaining yellow oil (5 g) was purified by SiO$_2$ chromatography (300 g SiO$_2$, DCM/(DCM:MeOH:NH$_4$OH 60:10:1) 100 to 87% DCM) to give 1 g of racemic benzyl-(3, 3-dimethyl-cyclohexyl)-amine as a light yellow oil (19% yield).

Step 2: To racemic benzyl-(3,3-dimethyl-cyclohexyl)-amine (1 g, 4.601 mmol) Pd(OH)$_2$ on carbon 20 wt % (0.5 g) and EtOH (20 mL) were added and the reaction mixture stirred at RT under 1 atm of H$_2$ overnight. The palladium was filtered off and the solvent was evaporated. Be careful, the free amine sublimes. The remaining pale brown oil was purified by SiO$_2$ chromatography (50 g SiO$_2$, DCM/(DCM: MeOH:NH$_4$OH 60:10:1) 100 to 65% DCM). The fractions containing the product were evaporated. The residue was dissolved in DCM and treated with 4M HCl in dioxane. The solvent was evaporated and the remaining solid was dried under high vacuum to give 0.17 g of racemic 3,3-dimethyl-cyclohexylamine hydrochloride as a white solid (22% yield).

Example 8

Synthesis of racemic spiro[2.5]oct-5-ylamine hydrochloride

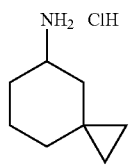

Step 1: 1,3-Cyclohexadione (10 g, 89.18 mmol) was dissolved in MeOH (50 mL) and concentrated $H_2SO_4$ (0.5 mL) was added. The resulting orange/brown solution was stirred at reflux overnight. The reaction was allowed to cool to RT before being neutralized by addition of NaOH pellets one at a time. The solvent was evaporated and the remaining oil was partitioned between $Et_2O$ and $H_2O$. The aqueous layer was extracted twice with $Et_2O$. The combined organic layers were washed with $H_2O$, then brine, dried ($Na_2SO_4$), filtered and evaporated. The remaining oil was dried under high vacuum overnight to give 7.87 g of 3-methoxy-cyclohex-2-enone as an orange oil, yield (70% yield).

Step 2: 3-Methoxy-cyclohex-2-enone (7.8 g, 61.83 mmol) was dissolved in $Et_2O$ (100 mL) and titanium tetraisopropoxide (20.1 mL, 68.01 mmol) was added. To the resulting brown solution ethylmagnesium bromide solution (3M, 60 mL, 180 mmol) was added dropwise over 70 minutes. A precipitate formed over the course of the addition. After 2 hours at RT the now dark brown/black reaction mixture was carefully quenched with saturated aqueous $NH_4Cl$. A dark gray precipitate formed and was filtered off over Celite. The aqueous layer was extracted twice with $Et_2O$. The combined organic layers were washed with brine, dried ($Na_2SO_4$), filtered, and evaporated. The residue was taken up in $Et_2O$ (100 mL) and p-toluenesulfonic acid monohydrate (0.588 g, 3.091 mmol) was added. The resulting brown solution was stirred at RT over the weekend before being evaporated. The remaining brown oil was purified by $SiO_2$ chromatography (330 g $SiO_2$, hexanes/EtOAc 0 to 7% EtOAc) to give 2.5 g of spiro[2.5]octan-5-one as a light yellow liquid (32% yield).

Step 3: Spiro[2.5]octan-5-one (0.875 g, 7.046 mmol) and benzylamine (0.81 mL, 7.4 mmol) were dissolved in benzene (5 mL) and stirred at reflux with continuous removal of $H_2O$ for 3 hours. The reaction mixture was allowed to cool to RT and the solvent was evaporated. The imine intermediate was dissolved in DCM (35 mL) and cooled to 0° C. Sodium triacetoxyborohydride (95%, 1.9 g, 8.455 mmol) and acetic acid (0.52 mL, 9.16 mmol) were added. After about 20 minutes, the ice bath was removed and the suspension was stirred at RT overnight. The reaction mixture was cooled to 0° C. and quenched by addition of saturated aqueous $NaHCO_3$. The aqueous layer was extracted with DCM. The combined organic layers were washed once more with saturated $NaHCO_3$, dried over $Na_2SO_4$, filtered, and evaporated. The remaining yellow oil was purified by $SiO_2$ chromatography (100 g $SiO_2$, DCM/(DCM:MeOH:$NH_4OH$ 60:10:1) 100 to 85% DCM) to give 1.1 g of racemic cis benzyl-spiro[2.5]oct-5-yl-amine as a light brown oil (72% yield).

Step 4: To racemic cis benzyl-spiro[2.5]oct-5-yl-amine (1.1 g, 5.108 mmol) Pd(OH)$_2$ on carbon 20 wt % (0.55 g) and EtOH (20 mL) were added and the reaction mixture stirred at RT under 1 atm of $H_2$ overnight. The palladium was filtered off, HCl 4M in dioxane was added to the filtrate and the solvent was evaporated. The remaining pale brown solid was purified by $SiO_2$ chromatography (50 g $SiO_2$, DCM/(DCM:MeOH:$NH_4OH$ 60:10:1) 100-65% DCM). The fractions containing the product were evaporated. The residue was dissolved in DCM and treated with 4M HCl in dioxane. The solvent was evaporated and the remaining solid was dried under high vacuum to give 0.19 g of racemic cis spiro[2.5]oct-5-ylamine hydrochloride as an off-white solid (23% yield).

Example 9

Synthesis of racemic cis 6-methyl-spiro[2.5]oct-5-ylamine hydrochloride

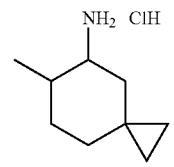

Step 1: Spiro[2.5]octan-5-one (2.4 g, 19.32 mmol) was dissolved in THF (100 mL) and cooled to −75° C. At that temperature LHMDS 1M in THF (24 mL, 24 mmol) was added dropwise over 15 minutes. The resulting pale yellow solution was stirred 1 hour at −75° C. Iodomethane (1.3 mL, 21.26 mmol) was added and stirring was continued at −75° C. for another hour before letting the mixture warm up to RT. The reaction was quenched by addition of saturated aqueous $NH_4Cl$. The layers were separated and the aqueous layer was extracted with $Et_2O$. The combined organic layers were washed with brine, dried ($Na_2SO_4$), filtered and evaporated. The remaining yellow oil was purified by $SiO_2$ chromatography (330 g $SiO_2$, hexanes/EtOAc 0 to 3% EtOAc) to give 0.93 g of racemic 6-methyl-spiro[2.5]octan-5-one as a colorless liquid (35% yield).

Step 2: Racemic 6-methyl-spiro[2.5]octan-5-one (0.92 g, 6.656 mmol) and benzylamine (0.76 mL, 6.989 mmol) were dissolved in benzene (6 mL) and stirred at reflux with continuous removal of $H_2O$ for 3 hours. The reaction mixture was allowed to cool to RT and was diluted with DCM (30 mL). The yellow solution was cooled to 0° C. Sodium triacetoxyborohydride (95%, 1.78 g, 7.988 mmol) and acetic acid (0.5 mL, 8.65 mmol) were added. After about 20 minutes, the ice bath was removed and the suspension stirred at RT overnight. The reaction mixture was cooled to 0° C. and quenched by addition of saturated aqueous $NaHCO_3$. The layers were separated and the aqueous layer was extracted with DCM. The combined organic layers were washed once more with saturated $NaHCO_3$, dried ($Na_2SO_4$), filtered and evaporated. The remaining yellow oil was purified by $SiO_2$ chromatography (100 g $SiO_2$, DCM/(DCM:MeOH:$NH_4OH$ 60:10:1) 100 to 85% DCM) to give 0.92 g of racemic cis benzyl-(6-methyl-spiro[2.5]oct-5-yl)-amine as a light brown oil (yield 60%).

Step 3: To racemic cis benzyl-(6-methyl-spiro[2.5]oct-5-yl)-amine (1.03 g, 4.491 mmol) Pd(OH)$_2$ on carbon 20 wt % (0.25 g) and EtOH (20 mL) were added and the reaction mixture was stirred at RT under 1 atm of H$_2$ overnight. The palladium was filtered off, HCl 4M in dioxane was added and the solvent was evaporated. The remaining pale brown solid was purified by SiO$_2$ chromatography (50 g SiO$_2$, DCM/(DCM:MeOH:NH$_4$OH 60:10:1) 100-57% DCM). The fractions containing the product were evaporated. The residue was dissolved in DCM and treated with 4M HCl in dioxane. The solvent was evaporated and the remaining solid was dried under high vacuum to give 0.4 g of racemic cis 6-methyl-spiro[2.5]oct-5-ylamine hydrochloride as a light brown solid (50% yield). NMR showed about 18% of the trans isomer.

Example 10

Synthesis of 1-((3R,5R)-3-amino-5-methyl-piperidin-1-yl)-ethanone hydrochloride

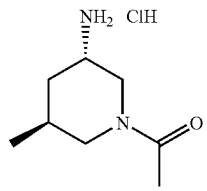

Step 1: To ((3R,5R)-1-benzyl-5-methyl-piperidin-3-yl)-carbamic acid tert-butyl ester (prepared as described in WO2004014893) (0.6 g, 1.971 mmol) Pd(OH)$_2$ on carbon (0.1 g) and EtOH (10 mL) were added and the reaction mixture was stirred at RT under 1 atm of H$_2$. After 2 hours the palladium was filtered off and the solvent was evaporated to give 0.45 g of ((3R,5R)-5-methyl-piperidin-3-yl)-carbamic acid tert-butyl ester as a colorless oil (>95% yield).

Step 2: ((3R,5R)-5-Methyl-piperidin-3-yl)-carbamic acid tert-butyl ester (0.422 g, 1.971 mmol) was dissolved in DCM. Pyridine (0.2 mL, 2.56 mmol) was added, followed by acetic anhydride (0.24 mL, 2.56 mmol). The resulting colorless solution was stirred at RT overnight. 1 mL of MeOH was added and the mixture was stirred for about 30 minutes before being evaporated. The residue was partitioned between EtOAc and aqueous 1M HCl. The aqueous layer was extracted with EtOAc. The combined organic layers were washed with brine, dried (Na$_2$SO$_4$), filtered, and evaporated. The remaining oil was dried under high vacuum to give 0.51 g of ((3R,5R)-1-acetyl-5-methyl-piperidin-3-yl)-carbamic acid tert-butyl ester as an off-white solid (>95% yield).

Step 3: ((3R,5R)-1-Acetyl-5-methyl-piperidin-3-yl)-carbamic acid tert-butyl ester (0.5 g, 1.971 mmol) was dissolved in DCM (15) and HCl 4M in dioxane (2.5 mL, 10 mmol) was added. The resulting colorless solution was stirred at RT until precipitation of a solid was observed. The solvent was evaporated and the residue was dried under high vacuum to give 0.45 g of 1-((3R,5R)-3-amino-5-methyl-piperidin-1-yl)-ethanone hydrochloride as an off-white solid (>95% yield).

Example 11

Synthesis of (3S,5S)-3-amino-5-methyl-piperidine-1-carboxylic acid benzyl ester hydrochloride

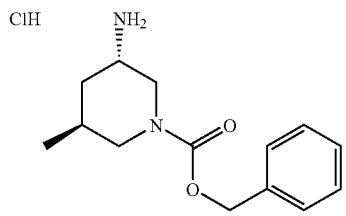

Step 1: To ((3R,5R)-1-benzyl-5-methyl-piperidin-3-yl)-carbamic acid tert-butyl ester (prepared as described in WO2004014893) (4.6 g, 15.11 mmol) Pd(OH)$_2$ on carbon (0.46 g) and EtOH (80 mL) were added and the reaction mixture stirred at RT under 1 atm of H$_2$. After 3 hours the palladium was filtered off and the solvent was evaporated. The remaining oil was dried under high vacuum to give 2.9 g of ((3R,5R)-5-methyl-piperidin-3-yl)-carbamic acid tert-butyl ester as an off-white crystalline solid (89% yield).

((3S,5S)-5-methyl-piperidin-3-yl)-carbamic acid tert-butyl ester was prepared in the same manner from ((3S,5S)-1-benzyl-5-methyl-piperidin-3-yl)-carbamic acid tert-butyl ester.

Step 2: ((3R,5R)-5-Methyl-piperidin-3-yl)-carbamic acid tert-butyl ester (2.9 g, 13.53 mmol) was dissolved in 70 mL of a 1:1 mixture of dioxane and H$_2$O and NaHCO$_3$ (4.55 g, 54.13 mmol) was added. To the resulting suspension benzyl chloroformate (2.2 mL, 14.2 mmol) was added slowly. After 2 hours the reaction mixture was extracted with EtOAc. The combined organic layers were washed with saturated aqueous NaHCO$_3$, dried (Na$_2$SO$_4$), filtered, and evaporated. The remaining oil was purified by SiO$_2$ chromatography (150 g SiO$_2$, hexanes/EtOAc 0 to 20% EtOAc) to give 3.6 g of (3R,5R)-3-tert-butoxycarbonylamino-5-methyl-piperidine-1-carboxylic acid benzyl ester as a colorless oil (76% yield).

(3S,5S)-3-tert-butoxycarbonylamino-5-methyl-piperidine-1-carboxylic acid benzyl ester was prepared in the same manner from ((3S,5S)-5-methyl-piperidin-3-yl)-carbamic acid tert-butyl ester.

Step 3: (3R,5R)-3-tert-Butoxycarbonylamino-5-methyl-piperidine-1-carboxylic acid benzyl ester (3.25 g, 9.327 mmol) was dissolved in DCM (50 mL) and HCl 4M in dioxane (20 mL, 80 mmol) was added. The resulting colorless solution stirred at RT for 4 hours before being evaporated. The residue was dried under high vacuum overnight to give 2.89 g of (3R,5R)-3-amino-5-methyl-piperidine-1-carboxylic acid benzyl ester hydrochloride as a white foam (>95% yield).

(3S,5S)-3-amino-5-methyl-piperidine-1-carboxylic acid benzyl ester hydrochloride was prepared in the same manner from (3S,5S)-3-tert-butoxycarbonylamino-5-methyl-piperidine-1-carboxylic acid benzyl ester.

Example 12

Synthesis of racemic trans Acetic acid 3-amino-cyclohexylmethyl ester

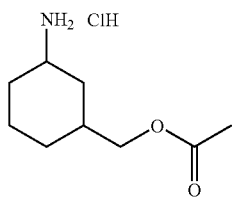

Step 1: Racemic trans 3-tert-butoxycarbonylamino-cyclohexanecarboxylic acid (1 g, 4.11 mmol) was dissolved in THF (30 mL) and borane dimethylsulfide 2M in THF (3 mL, 6 mmol) was added slowly. The resulting colorless solution was stirred at 40° C. After 4 hours the reaction mixture was cooled to 0° C., quenched by addition of saturated aqueous NaHCO$_3$, and extracted twice with EtOAc. The combined organic layers were dried (Na$_2$SO$_4$), filtered and evaporated to give 0.905 g of crude racemic trans 3-hydroxymethyl-cyclohexyl-carbamic acid tert-butyl ester as a colorless oil (>95% yield).

Step 2: Acetic anhydride (0.85 mL, 9.012 mmol) was added at 0° C. to a mixture of racemic trans 3-hydroxymethyl-cyclohexyl-carbamic acid tert-butyl ester (1.69 g, 7.37 mmol) and pyridine (0.78 mL, 9.646 mmol) in 20 mL of DCM. The resulting mixture was stirred at 0° C. to RT overnight and then at 50° C. for 4 hours before being cooled to RT and partitioned between DCM and aqueous 1M HCl. The aqueous layer was back extracted twice with DCM. The combined organic layers were dried (Na$_2$SO$_4$), filtered, and evaporated to give 2 g of racemic trans acetic acid 3-tert-butoxycarbonylamino-cyclohexylmethyl ester (>95% yield).

Step 3: HCl 4M in dioxane (5 mL) was added at RT to a solution of racemic trans acetic acid 3-tert-butoxycarbonylamino-cyclohexylmethyl ester (theoretically 7.37 mmol) in 10 mL of DCM. The resulting mixture was stirred at RT for 4 hours before being evaporated to give 1.5 g of racemic trans acetic acid-3-amino-cyclohexylmethyl ester hydrochloride (>95% yield).

Example 13

Synthesis of racemic trans-3-methoxymethyl-cyclohexylamine

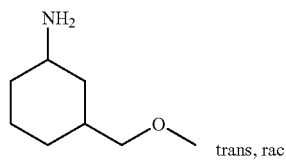

Step 1: Racemic trans 3-tert-butoxycarbonylamino-cyclohexanecarboxylic acid (1 g, 4.11 mmol) was dissolved in THF (30 mL) and borane dimethylsulfide 2M in THF (3 mL, 6 mmol) was added slowly. The resulting colorless solution was stirred at 40° C. After 4 hours the reaction mixture was cooled to 0° C., quenched by addition of saturated aqueous NaHCO$_3$, and extracted twice with EtOAc. The combined organic layers were dried (Na$_2$SO$_4$), filtered and evaporated to give 0.905 g of crude racemic trans 3-hydroxymethyl-cyclohexyl-carbamic acid tert-butyl ester as a colorless oil (>95% yield).

Step 2: Racemic trans 3-hydroxymethyl-cyclohexyl-carbamic acid tert-butyl ester (0.9 g, 3.925 mmol) was dissolved in DCM and 4M HCl in dioxane (9.8 mL) was added. The resulting mixture was stirred at RT for 4 hours before being evaporated. The residue was dried under high vacuum to give 0.65 g of crude racemic trans-3-amino-cyclohexyl-methanol as white foam (>95% yield).

Step 3: Racemic trans 3-amino-cyclohexyl-methanol (0.65 g, 3.925 mmol) was taken up in toluene (25 mL) and triethylamine (1.6 mL, 11.5 mmol). Phthalic anhydride (0.581 g, 3.925 mmol) was added and the resulting mixture was stirred at reflux overnight. The reaction mixture was allowed to cool to RT before being washed with H$_2$O. The aqueous layer was extracted with EtOAc. The combined organic layers were washed with brine, dried (Na$_2$SO$_4$), filtered, and evaporated. The remaining solid was purified by SiO$_2$ chromatography (40 g SiO$_2$, hexanes/EtOAc 0 to 40%) to give 0.749 g of racemic trans-2-(3-hydroxymethyl-cyclohexyl)-isoindole-1,3-dione as a white solid (73% yield).

Step 4: Racemic trans 2-(3-hydroxymethyl-cyclohexyl)-isoindole-1,3-dione (0.37 g, 1.427 mmol) was dissolved in DMF (7 mL) and cooled to 0° C. At that temperature, NaH (60%, 0.136 g, 3.424 mmol) was added, followed by iodomethane (0.54 mL, 8.676 mmol) about 10 minutes later. After another 10 minutes the ice bath was removed, and the reaction mixture was heated to 38° C. After 3 hours, another 6 equivalents of iodomethane were added and the reaction mixture was stirred at 38° C. overnight before being cooled, quenched by addition of saturated aqueous NH$_4$Cl, and extracted times with Et$_2$O. The organic layers were combined, dried (Na$_2$SO$_4$), filtered, and evaporated. The remaining orange oil was purified by SiO$_2$ chromatography (24 g SiO$_2$, hexanes/EtOAc 0 to 10% EtOAc) to give 0.21 g of racemic trans 2-(3-methoxymethyl-cyclohexyl)-isoindole-1,3-dione as white crystalline solid (54% yield).

Step 5: Racemic trans-2-(3-methoxymethyl-cyclohexyl)-isoindole-1,3-dione (0.205 g, 0.75 mmol) was suspended in EtOH (5 mL) and hydrazine (0.07 mL, 2.25 mmol) was added. The resulting colorless mixture was stirred at 50° C. for 3 hours before cooled to RT. The solid that precipitated was filtered off and washed with EtOH. The filtrate was evaporated to give 0.235 g of racemic trans-3-methoxymethyl-cyclohexylamine as a white solid (50% pure by NMR).

Example 14

Synthesis of racemic cis 2,5,5-trimethyl-cyclohexylamine hydrochloride

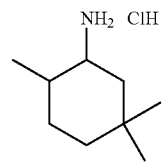

Step 1: 3,3-Dimethylcyclohexanone (4 g, 31.7 mmol) was added dropwise at −78° C. to a solution of LHMDS 1M in THF (35 mL, 35 mmol) in 100 mL of THF. The resulting mixture was stirred at −78° C. for 1 hour before adding iodomethane (2.2 mL, 35.33 mmol). The reaction was stirred at −78° C. to RT overnight before being quenched by addition of saturated aqueous $NH_4Cl$, and extracted three times with $Et_2O$. The combined organic layers were dried (MgSO4), filtered, and evaporated. The crude racemic 2,5,5-trimethyl-cyclohexanone was used in the next step without purification.

Step 2: A mixture of crude racemic 2,5,5-trimethyl-cyclohexanone (theoretically 31.7 mmol) and benzylamine (3.8 mL, 34.79 mmol) in 50 mL of toluene was stirred for 45 minutes at reflux with continuous removal of $H_2O$. The reaction mixture was cooled to RT and evaporated. The residue was taken into 50 mL of DCM and sodium triacetoxyborohydride (8.1 g, 38.22 mmol) was added, followed by acetic acid (2 mL, 34.94 mmol). The resulting mixture was stirred at RT overnight before being diluted with DCM and washed with saturated aqueous $NaHCO_3$. The aqueous layer was back extracted twice with DCM. The combined organic layers were dried ($Na_2SO_4$), filtered, and evaporated. The residue was purified (DCM/(DCM:MeOH:$NH_4OH$ 60:10:1] 90% DCM) to give 3.84 g of racemic benzyl-(2,5,5-trimethyl-cyclohexyl)-amine. NMR showed the presence of about 5% of the trans isomer.

Step 3:
A mixture of racemic cis benzyl-(2,5,5-trimethyl-cyclohexyl)-amine (1.9 g, 8.211 mmol) and $Pd(OH)_2$ 20 wt % on carbon (0.9 g) in 50 mL of EtOH was stirred under an hydrogen atmosphere (1 atm) at RT overnight before being filtered. The cake was rinsed thoroughly with MeOH and the filtrate was evaporated. The residue was purified by $SiO_2$ chromatography (DCM/(DCM:MeOH:$NH_4OH$ 60:10:1 50% DCM). The fractions containing the product were evaporated. The residue was taken into 4 mL of a 1:1 mixture of DCM and HCl 4M in dioxane. The mixture was evaporated to give 0.61 g of racemic cis 2,5,5-trimethyl-cyclohexylamine hydrochloride (42% yield).

Example 15

Synthesis of racemic
1-(2,2,2-trifluoro-ethyl)-piperidin-3-ylamine
hydrochloride

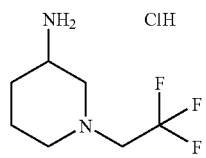

Step 1: Trifluoro-methanesulfonic acid 2,2,2-trifluoro-ethyl ester (0.42 g, 1.8 mmol) was dissolved in a mixture of 1.5 mL of EtOAc and 1.5 mL of $H_2O$ containing 0.95 g of $NaHCO_3$ (7.5 mmol). The resulting suspension was warmed to 50 C. A solution of racemic piperidin-3-yl-carbamic acid tert-butyl ester (0.30 g, 1.5 mmol) in 1 mL of EtOAc was added dropwise over a 30 minute period. The reaction mixture was left stirring at 50° C. for one hour before being cooled to RT. The organic phase was separated and the aqueous layer was back extracted with EtOAc. The combined organics were washed with brine, dried (MgSO4), filtered and evaporated to give 0.38 g of racemic [1-(2,2,2-trifluoro-ethyl)-piperidin-3-yl]-carbamic acid tert-butyl ester as a colorless oil which was used in the next step without purification.

Step 2: [1-(2,2,2-Trifluoro-ethyl)-piperidin-3-yl]-carbamic acid tert-butyl ester (0.380 g, 1.3 mmol) was dissolved in 3 mL of dioxane. A 4 M solution of HCl in dioxane (3.3 mL, 13.3 mmol) was added and the resulting mixture was stirred overnight at RT before being evaporated to give racemic 1-(2,2,2-trifluoro-ethyl)-piperidin-3-ylamine hydrochloride.

Example 15

Synthesis of racemic
1-acetyl-3-methyl-piperidin-4-one

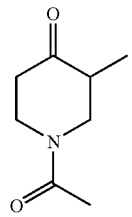

Step 1: To a solution of racemic 3-methyl-4-oxo-piperidine-1-carboxylic acid tert-butyl ester in anhydrous DCM at 0° C., ethanolic-HCl was added slowly and the reaction mixture was allowed to stir at 25° C. for 3 h. TLC (hexanes/EtOAc 40% EtOAc) showed complete consumption of the starting material. The reaction mixture was evaporated to give racemic 3-methyl-piperidin-4-one hydrochloride which was used crude in the next reaction.

Step 2: To a suspension of the product of step 1 in DCM at 0° C., DIPEA (4 eqv) was added slowly and stirred for 30 minutes at 25° C. The reaction mixture was cooled again to 0° C. and acetyl chloride (1.1 eqv) was added slowly. The resulting mixture was stirred at 25° C. for 16 hrs before being quenched by addition of saturated aqueous $NaHCO_3$. The aqueous layer was back extracted three times with DCM. The combined organics were washed with $H_2O$, dried ($Na_2SO_4$), filtered and evaporated. The residue was purified by $SiO_2$ flash chromatography to give racemic 1-acetyl-3-methyl-piperidin-4-one (94% over two steps).

Racemic 1-methanesulfonyl-3-methyl-piperidin-4-one was prepared in the same manner from racemic 3-methyl-piperidin-4-one hydrochloride and methanesulfonyl chloride.

Racemic 3-methyl-4-oxo-piperidine-1-carboxylic acid methyl ester was prepared in the same manner from racemic 3-methyl-piperidin-4-one hydrochloride and methyl chloroformate.

Example 16

Synthesis of 2-methyl-cycloheptanone

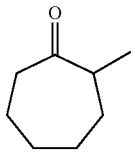

n-BuLi (2M solution) (35.86 mmol, 17.93 mL) was slowly added at 0° C. to a solution of DIPEA (5 mL, 35.86 mmol) in THF (45 mL). After stirred for 30 min at 0° C. the solution was cooled to −78° C. Cycloheptanone (4.0 gms, 4.2 mL, 35.66 mmol, 1.0 eqv) was added drop wise and the resulting mixture was stirred for 30 min at −78° C. before adding methyl iodide (2.96 mL, 47.4 mmol, 1.33 eq). The cooling bath was removed and the solution was allowed to reach ambient temperature and stirred at RT for 15 hours before being quenched with aqueous saturated NH$_4$Cl. The mixture was extracted with DCM. The organic layer was washed with 0.1 M aqueous HCl and aqueous saturated NaHCO$_3$, dried over Na$_2$SO$_4$, filtered, and evaporated. The residue was purified by short path distillation to give 2.8 g of 2-methyl-cycloheptanone (62% yield).

Example 17

Synthesis of racemic
1-acetyl-5-methyl-azepan-4-one

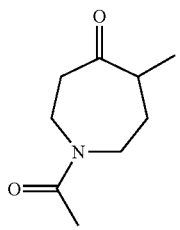

Step 1: A solution of compound racemic 5-oxo-azepane-1,4-dicarboxylic acid 1-tert-butyl ester 4-ethyl ester (2.5 g, 8.77 mmole) in 10 mL of DMF was added at 0° C. to a stirred suspension of NaH 60% dispersion in oil (355 mg, 8.77 mmole) in 10 mL of DMF. The reaction mixture was allowed to stir RT for one hour before being cooled to 0° C. Methyl iodide (1.37 mL, 21.92 mmole, 2.5 eqv) was added slowly and the reaction mixture was stirred at RT for 3 h before being poured into cold H$_2$O and extracted with EtOAc (50 mL). The organic layer was washed with brine, dried, and evaporated to give 2.5 g of 4-methyl-5-oxo-azepane-1,4-dicarboxylic acid 1-tert-butyl ester 4-ethyl ester desired compound (95% yield).

Step 2: To a solution of compound 4-methyl-5-oxo-azepane-1,4-dicarboxylic acid 1-tert-butyl ester 4-ethyl ester (2.5 g, 8.36 mmol) in dioxane (20 mL) was added 2 M aqueous KOH (20 mL) at 25° C. The resulting solution was stirred at 100° C. for 24 hours before being cooled to RT and extracted twice with EtOAC. The combined organic layers were dried (Na$_2$SO$_4$), filtered, and evaporated to give 1.8 g of 4-methyl-5-oxo-azepane-1-carboxylic acid tert-butyl ester (95% yield).

Step 3: A solution of 4-methyl-5-oxo-azepane-1-carboxylic acid tert-butyl ester (700 mg, 3.083 mmol) was dissolved in 10% TFA in DCM (30 mL) and stirred at RT for 6 hours before being evaporated to give 0.74 g of 5-methyl-azepan-4-one hydrochloride.

Step 4: Acetic anhydride (0.437 mL, 4.62 mmol) was added at 0° C. to a solution of 5-methyl-azepan-4-one hydrochloride (0.740 g, 3.08 mmol) in DCM (20 mL) and pyridine (0.25 mL, 3.08 mmol). The reaction mixture was stirred at RT for 8 hours before being partitioned between DCM and H$_2$O. The organic layer was dried (Na$_2$SO$_4$), filtered, and evaporated. The crude residue was purified by SiO$_2$ chromatography (100% EtOAc) to give 0.220 g of 1-acetyl-5-methyl-azepan-4-one (42% yield).

Example 18

Synthesis of
(1S,3S)-3-amino-cyclopentanecarboxylic acid
methyl ester hydrochloride

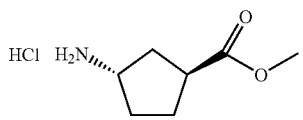

Acetyl chloride (3.5 mL, 49.3 mmol) was added dropwise at 0° C. to 100 mL of MeOH. The resulting mixture was stirred at 0° C. for 5 minutes before adding (1S,3S)-3-tert-butoxycarbonylamino-cyclopentanecarboxylic acid methyl ester (1.192 g, 5.2 mmol). The reaction mixture was allowed to warm up to RT and stirred for 48 h before being evaporated to give crude (1S,3S)-3-amino-cyclopentanecarboxylic acid methyl ester hydrochloride which was used as is in the following step.

Example 19

Synthesis of 3-amino-cyclohexanecarboxylic acid
dimethylamide hydrochloride

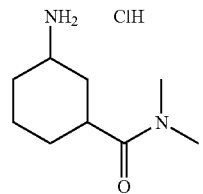

Step 1: DIPEA (1.8 mL, 10.3 mmol) was added at RT to a mixture of racemic trans 3-tert-butoxycarbonylamino-cyclohexanecarboxylic acid (1.00 g, 4.109 mmol), dimethylamine hydrochloride (0.0.503 g, 6.17 mmol), and EDCI (1.182 g, 6.17 mmol) in 13 mL of DCM. The resulting mixture was stirred at RT for 16 hours before being partitioned between H$_2$O and DCM. The aqueous layer was back extracted twice with DCM. The combined organic layers were dried (Na$_2$SO$_4$), filtered, and evaporated. The residue was purified by SiO$_2$ flash chromatography (DCM/MeOH 0 to 5% MeOH) to give 0.438 g (39%) of racemic trans 3-dimethylcarbamoyl-cyclohexyl carbamic acid tert-butyl ester.

Step 2: Racemic trans 3-Dimethylcarbamoyl-cyclohexyl carbamic acid tert-butyl ester (0.437 g, 1.62 mmol) was dissolved in 50 mL of MeOH and cooled to 20° C. Acetyl chloride (1.2 mL, 16.9 mmol) was added dropwise and when the addition was complete the reaction mixture was allowed to warm up to RT and stirred for 16 h. The solvent was removed under vacuum concentrated to dryness to give racemic trans 3-amino-cyclohexanecarboxylic acid dimethylamide hydrochloride which was used as is in the following step.

Example 20

Synthesis of trans-3-(5,6-dichloro-1,3-dihydro-isoindol-2-yl)-cyclopentylamine

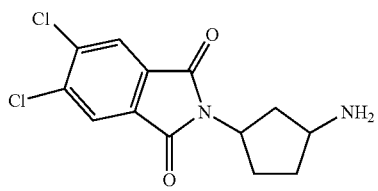

Step 1: To a round bottomed flask was added trans 3-(tert-butyl-dimethyl-silanyloxy)-cyclopentanol (1.0 g, 4.62 mmol, prepared from WO2008065021), triphenylphosphine (1.52 g, 5.76 mmol) and 2-methyltetrahydrofuran (120 mL). Diisopropyl azodicarboxylate (1.23 mL, 6.25 mmol) was added over two minutes via syringe followed by 4,5-dichlorophthalimide (1.35 g, 6.25 mmol). The reaction was stirred overnight and evaporated. The reaction was repeated and the combined material was purified by column chromatography (160 g SiO$_2$, EtOAc in hexane) to give cis 2-[3-(tert-butyl-dimethyl-silanyloxy)-cyclopentyl]-5,6-dichloro-isoindole-1,3-dione, a yellowish solid (2.0 gm, 52% yield)

Step 2: To a flask containing HCl (37%, 5 mL) and methanol (155 mL) was added cis 2-[3-(tert-butyl-dimethyl-silanyloxy)-cyclopentyl]-5,6-dichloro-isoindole-1,3-dione (1.7 g, 4.1 mmol). The mixture was placed in an ultrasound bath until all of the solid had dissolved (15 minutes) then evaporated to give cis 5,6-dichloro-2-(3-hydroxy-cyclopentyl)-2,3-dihydro-1H-isoindole-1,3-diol (1.172 g, 95% yield).

Step 3: To a flask was added DCM (40 mL), DIPEA (2.0 mL, 11.48 mmol), c is 5,6-dichloro-2-(3-hydroxy-cyclopentyl)-2,3-dihydro-1H-isoindole-1,3-diol 1.071 g, 3.57 mmol) and methanesulfonyl chloride (0.6 mL, 7.72 mmol) and the mixture stirred overnight at RT. The mixture was concentrated in vacuo, EtOAc (100 mL) and H$_2$O (100 mL) added, filtered off insolubles, separated and extracted the aqueous layer with EtOAc (50 mL). The combined organic layers were dried (MgSO4) and concentrated in vacuo to give cis methanesulfonic acid 3-(5,6-dichloro-1,3-dihydroxy-1,3-dihydro-isoindol-2-yl)-cyclopentyl ester as a tan solid (1.5 g, impure as >100% yield).

Step 4: In a flask cis methanesulfonic acid 3-(5,6-dichloro-1,3-dihydroxy-1,3-dihydro-isoindol-2-yl)-cyclopentyl ester (1.32 g, 3.49 mmol) was added to DMF (15 mL) and sodium azide (0.24 g, 3.7 mmol) and stirred at RT overnight. The mixture was diluted with H$_2$O (100 mL) and extracted with diethyl ether (3×100 mL), the organic layers were dried (MgSO$_4$) and concentrated in vacuo to give a tan solid (1.6 g). The solid was purified four times by column chromatography (2×EtOAc in hexane, 2×EtOAc in hexane/dichloromethane) followed by preparative TLC (EtOAc in hexane) and then recrystallized from dichloromethane in hexane to give trans 2-(3-azido-cyclopentyl)-5,6-dichloro-isoindole-1,3-dione (0.727 g, 64% yield).

Step 5: Trans 2-(3-azido-cyclopentyl)-5,6-dichloro-isoindole-1,3-dione (0.727 g, 2.24 mmol) and lindlar catalyt (0.36 g) was added to a mixture of ethanol and dichloromethane and placed under a hydrogen balloon overnight. The mixture was filtered and the solid rinsed with dichloromethane. The organic layers were concentrated in vacuo, dissolved in methanol and diluted with acetonitrile. The solid was removed by filtration and the filtrate purified by preparative TLC (dichloromethane/methanol/triethylamine). The solid and material from TLC was recrystallized from MeCN/MeOH to give trans 2-(3-amino-cyclopentyl)-5,6-dichloro-isoindole-1,3-dione as an off white solid (0.145 g, contains also trans 2-(3-amino-cyclopentyl)-5-chloro-isoindole-1,3-dione)

Example 21

Synthesis of cyclopropyl-acetyl chloride

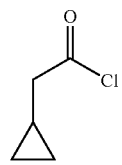

Oxalyl chloride (1.14 mL, 1.0 mmol) was added to a solution of cyclopropyl acetic acid (1.0 g, 10.0 mmol) in 6.0 mL of DCM. A couple of drops of DMF were added and the reaction mixture was left stirring overnight at RT before being evaporated to give 1.2 g of cyclopropyl-acetyl chloride.

Example 22

Synthesis of 2-methoxy-ethanesulfonyl chloride

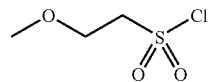

Step 1: 2-Chloroethyl methyl ether (10 g, 0.106 mol) was added at RT to a suspension of sodium sulfite (13.35 g, 0.106 mol) in 30 mL of H$_2$O. The resulting biphasic mixture was stirred at reflux for 48 hours before being cooled to RT (clear monophasic solution), and evaporated. The white residue was turned into a powder and was then washed with 100 mL of an 8/2 mixture of Et$_2$O and toluene, before being dried to give 22 g sodium 2-methoxy-ethanesulfonate (129% yield, contaminated with excess sodium sulfite). Used as is in step 2.

Step 2: A suspension of sodium 2-methoxy-ethanesulfonate (5 g, 30.84 mmol) in 16 mL of phosphorous oxychloride was stirred at reflux for 8 hours before being cooled to RT, and stirred at RT overnight before being diluted with DCM and filtered. The filtrate was partially evaporated, diluted with EtOAc and poured into crushed ice. After stirring until the ice has melted, the organic layer was separated, dried (Na₂SO₄), filtered and evaporated to give 4.88 g of 2-methoxy-ethanesulfonyl chloride (>95% yield).

Example 23

Synthesis of (1-trifluoromethyl-cyclopropyl)-methanesulfonyl chloride

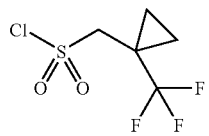

Step 1: 50 mL of borane dimethylsulfide 2M in THF were added dropwise at RT via an addition funnel to a solution of 1-trifluormethyl-cyclopropanecarboxylic acid (10 g, 64.90 mmol) in 100 mL of THF. The resulting clear solution was stirred at 40° C. for 24 hours before being cooled to 0° C. and quenched by slow addition of aqueous saturated NH₄Cl. The biphasic slurry was filtered through celite. The organic layer was separated, and the aqueous layer was back extracted twice with AcOEt. The combined organic layers were dried (Na₂SO₄), filtered, and evaporated to give 7 g of (1-trifluoromethyl-cyclopropyl)-methanol (77% yield). Used as in the next step.

Step 2: p-Toluenesulfonyl chloride (9.6 g, 50.35 mmol) was added at 0° C. to a mixture of (1-trifluoromethyl-cyclopropyl)-methanol (7 g, 49.96 mmol), triethylamine (7.7 mL, 55.24 mmol) and DMAP (0.61 g, 4.996 mmol) in 100 mL of DCM. The resulting mixture was stirred at 0° C. to RT overnight before being washed with aqueous 1M HCl. The aqueous layer was back extracted twice with DCM. The combined organic layers were dried (Na₂SO₄), filtered, and evaporated. The residue was purified by SiO₂ flash chromatography (120 g SiO₂, hexanes/[hexanes/Et₂O 8/2] 100 to 0% hexanes) to give 7.26 g of toluene-4-sulfonic acid 1-trifluoromethyl-cyclopropylmethyl ester (49% yield).

Step 3: A mixture of toluene-4-sulfonic acid 1-trifluoromethyl-cyclopropylmethyl ester (2 g, 6.796 mmol) and thiourea (0.52 g, 6.831 mmol) in 5 mL of EtOH was stirred at 90° C. for 3 hours before being cooled to RT and evaporated to give 2.5 g of 2-(1-trifluoromethyl-cyclopropylmethyl)-isothiourea p-toluenesulfonic acid salt (>95% yield).

Step 4: Chlorine was bubbled for 5 minutes at 0° C. through a suspension of 241-trifluoromethyl-cyclopropylmethyl)-isothiourea p-toluenesulfonic acid salt (theoretically 6.796 mmol) in 10 mL of H₂O and 2.5 mL of THF. The resulting light green mixture was warmed to RT and extracted twice with DCM. The combined organic layers were dried (Na₂SO₄), filtered, and evaporated to give 0.67 g of (1-trifluoromethyl-cyclopropyl)-methanesulfonyl chloride (44% yield).

Example 24

Synthesis of (3-methyl-oxetan-3-yl)-methanesulfonyl chloride

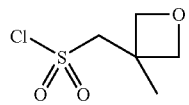

Step 1: A mixture of 3-chloromethyl-3-methyl-oxetane (5 g, 41.47 mmol), thiourea (3.16 g, 41.51 mmol), and potassium iodide in 30 mL of EtOH was stirred at 90° C. for 3 hours before being cooled to RT and evaporated. The residue was used as is in the next step.

Step 2: Chlorine was bubbled for 5 minutes at 0° C. through a solution of the crude product from step 1 (theoretically 41.47 mmol) in 30 mL of H₂O. The resulting dark brown mixture was warmed to RT and extracted twice with DCM. The combined organic layers were washed with 10% sodium thiosulfate (Na₂S₂O₃), dried (Na₂SO₄), filtered, and evaporated to give 0.75 g of (3-methyl-oxetan-3-yl)-methanesulfonyl chloride which was 50% pure by NMR. It was used as is in the next step.

Example 25

Synthesis of 3-cyclohexyl-1-methyl-1-(5H-pyrrolo[2,3-b]pyrazin-2-yl)-urea

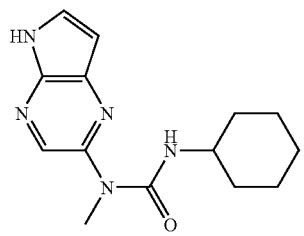

Step 1: 2-Bromo-5H-pyrrolo[2,3-b]pyrazine (1.98 g, 10.0 mmol) was dissolved in DMF (33 mL) and cooled down to 0° C. NaH (60%, 0.480 g, 12.0 mmol) was added slowly. After the addition was complete stirring was continued for 30 minutes at 0° C. (2-Chloromethoxy-ethyl)-trimethyl-silane (2.1 mL, 12.0 mmol) was added and the reaction mixture was allowed to warm up overnight. The reaction was quenched with H₂O. The aqueous layer was extracted with EtOAc. The organic layer was dried (MgSO₄), filtered, concentrated, and purified by SiO₂ chromatography (150 g SiO₂, hexanes/EtOAc 0-35% EtOAc) to give 2.81 g of 2-bromo-5-(2-trimethylsilanyl-ethoxymethyl)-5H-pyrrolo[2,3-b]pyrazine as a yellow liquid (86% yield).

Step 2: 2-Bromo-5-(2-trimethylsilanyl-ethoxymethyl)-5H-pyrrolo[2,3-b]pyrazine (0.328 g, 1.00 mmol) was dissolved in DMSO (2.5 mL). A solution of methylamine (33 wt % in EtOH, 2.5 mL, 20 mmol) was added and the resulting solution was heated at 150° C. in the sealed tube overnight, then cooled to RT. The reaction mixture was partitioned between EtOAc and H₂O. The aqueous layer was extracted with EtOAc. The combined organic layers were washed with brine, dried (MgSO₄), filtered and concentrated to give a mixture of impure Methyl-[5-(2-trimethylsilanyl-ethoxymethyl)-5H-pyrrolo[2,3-b]pyrazin-2-yl]-amine, which was dissolved in 1,2-dichloroethane (3 mL). Cyclohexylisocyanate (0.38 mL, 3.00 mmol) was added and the reaction mixture was heated to reflux overnight, cooled to RT, concentrated, purified by SiO₂ chromatography (12 g SiO₂, hexanes/EtOAc 0-35% EtOAc) to give 0.110 g of 3-cyclohexyl-1-methyl-1-[5-(2-trimethylsilanyl-ethoxymethyl)-5H-pyrrolo[2,3-b]pyrazin-2-yl]-urea as a yellow solid (27% yield).

Step 3: 3-Cyclohexyl-1-methyl-1-[5-(2-trimethylsilanyl-ethoxymethyl)-5H-pyrrolo[2,3-b]pyrazin-2-yl]-urea (0.110 g, 0.273 mmol) was dissolved in DCM (3 mL). TFA (1.0 mL) was added and the resulting solution was stirred at RT for 6 hours, then concentrated. The residue was dissolved in EtOH (2 mL), and NaOAc 3H₂O (0.371 g, 2.73 mmol) was added. The reaction mixture was stirred at RT overnight, concentrated and purified by SiO₂ chromatography (12 g SiO₂, DCM/MeOH 0-5% MeOH) followed by washing with a mixture of MeOH:H₂O:TEA (8:1:1) to give 48 mg of 3-cyclohexyl-1-methyl-1-[5-(2-trimethylsilanyl-ethoxymethyl)-5H-pyrrolo[2,3-b]pyrazin-2-yl]-urea as a yellow solid (64% yield).

Example 26

Synthesis of 1-cyclohexyl-3-(6-methyl-5H-pyrrolo[2,3-b]pyrazin-2-yl)-urea

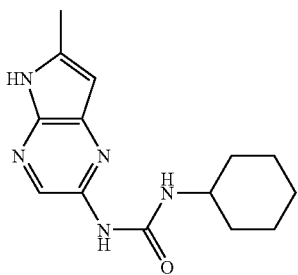

Step 1: 3,5-Dibromo-pyrazin-2-ylamine (1.70 g, 6.70 mmol), TEA (1.1 mL, 8.04 mmol), PdCl₂(PPh₃)₄ (28 mg, 0.040 mmol), and CuI (15 mg, 0.080 mmol) were dissolved in THF (17 mL), cooled to RT and Trimethyl-prop-2-ynyl-silane (1.0 mL, 6.7 mmol) was added at 0° C., allowed to warm up to RT and stirred overnight. The reaction mixture was diluted with EtOAc, washed with H₂O and saturated aqueous NaHCO₃, dried (MgSO₄) and concentrated, and purified by SiO₂ chromatography (80 g SiO₂, hexanes/EtOAc 0-35% EtOAc) to give 1.66 g of 5-bromo-3-(3-trimethylsilanyl-prop-1-ynyl)-pyrazin-2-ylamine as a yellow semi-solid contaminated by starting material (87% yield, 66% purity).

Step 2: To a solution of 5-bromo-3-(3-trimethylsilanyl-prop-1-ynyl)-pyrazin-2-ylamine (1.66 g, 66% purity, 5.84 mmol) in 25 mL of THF was added a solution of tBuOK in THF (1M, 11.7 mL, 11.7 mmol) slowly at RT. The reaction mixture was heated to reflux for 2 days, then cooled to RT, diluted with EtOAc, quenched with H₂O, filtered through a pad of celite, and washed with H₂O and EtOAc. The organic layer was separated, washed with H₂O and brine, dried (MgSO₄), and concentrated to give 598 mg of 2-bromo-6-methyl-5H-pyrrolo[2,3-b]pyrazine as a brown solid (48% yield).

Step 3: 2-Bromo-6-methyl-5H-pyrrolo[2,3-b]pyrazine (0.300 g, 1.41 mmol) was dissolved in DMF (5 mL) and cooled down to 0° C. NaH (60%, 68 mg, 1.70 mmol) was added slowly. After the addition was complete stirring was continued for 30 minutes at 0° C. (2-Chloromethoxy-ethyl)-trimethyl-silane (0.30 mL, 1.70 mmol) was added and the reaction mixture was allowed to warm up overnight. The reaction was quenched with H₂O. The aqueous layer was extracted with EtOAc. The organic layer was dried (MgSO₄), filtered, concentrated, and purified by SiO₂ chromatography (40 g SiO₂, hexanes/EtOAc 0-35% EtOAc) to give 340 mg of 2-bromo-6-methyl-5-(2-trimethylsilanyl-ethoxymethyl)-5H-pyrrolo[2,3-b]pyrazine as a yellow liquid (70% yield).

Step 4: 2-Bromo-6-methyl-5-(2-trimethylsilanyl-ethoxymethyl)-5H-pyrrolo[2,3-b]pyrazine (0.340 g, 0.993 mmol), benzhydrylideneamine (0.18 mL, 1.09 mmol), Cs₂CO₃ (648 mg, 1.99 mmol), Pd(OAc)₂ (22 mg, 0.099 mmol) and BINAP (62 mg, 0.099 mmol) were dissolved in THF (10 mL) and heated at 100° C. for 64 hr, cooled to RT, partitioned between EtOAc and brine. The organic layer was dried (MgSO₄), filtered, concentrated, and purified by SiO₂ chromatography (40 g SiO₂, hexanes/EtOAc 0-35% EtOAc) to give 158 mg of benzhydrylidene-[6-methyl-5-(2-trimethylsilanyl-ethoxymethyl)-5H-pyrrolo[2,3-b]pyrazin-2-yl]-amine as a yellow liquid (36% yield).

Step 5: Benzhydrylidene-[6-methyl-5-(2-trimethylsilanyl-ethoxymethyl)-5H-pyrrolo[2,3-b]pyrazin-2-yl]-amine (0.158 g, 0.357 mmol), NaOAc (70 mg, 0.857 mmol) and NH₂OH HCl (45 mg, 0.643 mmol) were dissolved in MeOH (4 mL) and stirred at RT overnight, and partitioned between EtOAc and brine. The organic layer was dried (MgSO₄), filtered, concentrated, and purified by SiO₂ chromatography (24 g SiO₂, hexanes/EtOAc 0-90% EtOAc) to give 58 mg of 6-methyl-5-(2-trimethylsilanyl-ethoxymethyl)-5H-pyrrolo[2,3-b]pyrazin-2-ylamine as a yellow solid (58% yield).

Step 6: 6-Methyl-5-(2-trimethylsilanyl-ethoxymethyl)-5H-pyrrolo[2,3-b]pyrazin-2-ylamine (58 mg, 0.208 mmol) was dissolved in 1,2-dichloroethane (2.1 mL). Cyclohexylisocyanate (0.54 mL, 4.16 mmol) was added and the reaction mixture was heated to reflux overnight, cooled to RT, concentrated, purified by SiO₂ chromatography (12 g SiO₂, hexanes/EtOAc 0-50% EtOAc) to give 80 mg of 1-cyclohexyl-3-[6-methyl-5-(2-trimethylsilanyl-ethoxymethyl)-5H-pyrrolo[2,3-b]pyrazin-2-yl]-urea as a yellow solid (95% yield).

Step 7: 1-Cyclohexyl-3-[6-methyl-5-(2-trimethylsilanyl-ethoxymethyl)-5H-pyrrolo[2,3-b]pyrazin-2-yl]-urea (56 mg, 0.139 mmol) was dissolved in a solution of HCl in AcOH (1M, 2.8 mL), and heated at 50° C. in the sealed tube overnight. The reaction mixture was concentrated to dryness, dissolved in 1.5 mL of MeOH:H₂O:Et₃N 8:1:1 and ethylenediamine (93 ul, 1.39 mmol) was added. The reaction mixture was stirred overnight, concentrated and purified by and purified by SiO₂ chromatography (8 g SiO₂, DCM/MeOH 0-5%

MeOH) to give 12 mg of 1-cyclohexyl-3-(6-methyl-5H-pyrrolo[2,3-b]pyrazin-2-yl)-urea as a white solid (32% yield).

Example 27

Synthesis of 1-cyclohexyl-3-(7-methyl-5H-pyrrolo[2,3-b]pyrazin-2-yl)-urea

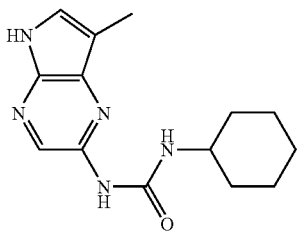

Step 1: To a solution of 3,5-dibromo-pyrazin-2-ylamine (5.06 g, 20.00 mmol) in 100 mL of THF was added a solution of LiHMDS in THF (1M, 24 mL) at RT. The reaction mixture was stirred at RT for 2 hr, then allyl bromide (3.5 mL, 40 mmol) was added. The reaction mixture was stirred at RT overnight and quenched with saturated NH$_4$Cl solution and extracted with EtOAc. The organic layer was washed with H$_2$O and brine, dried (MgSO$_4$) concentrated, and purified by SiO$_2$ chromatography (200 g SiO$_2$, hexanes/EtOAc 0-35% EtOAc) to give 3.51 g of allyl-(3,5-dibromo-pyrazin-2-yl)-amine as a yellow oil (60% yield).

Step 2: The mixture of allyl-(3,5-dibromo-pyrazin-2-yl)-amine (3.51 g, 12.0 mmol), TEA (4 mL, 28.8 mmol), sodium formate (204 mg, 3.00 mmol), Bu$_4$NH$_4$Br (580 mg, 1.80 mmol), and Pd(OAc)$_2$ (269 mg, 1.20 mmol) in 24 mL of DMF was heated at 50° C. overnight then cooled to RT. The reaction mixture was partitioned between EtOAc and brine. The organic layer was dried (MgSO$_4$), concentrated, and purified by SiO$_2$ chromatography (120 g SiO$_2$, hexanes/EtOAc 0-70% EtOAc) to give 0.279 g of 2-bromo-7-methyl-5H-pyrrolo[2,3-b]pyrazine (11% yield).

Step 3: 2-Bromo-7-methyl-5H-pyrrolo[2,3-b]pyrazine (0.279 g, 1.321) was dissolved in DMF (5 mL) and cooled down to 0° C. NaH (60%, 63 mg, 1.58 mmol) was added slowly. After the addition was complete stirring was continued for 30 minutes at 0° C. (2-Chloromethoxy-ethyl)-trimethyl-silane (0.28 mL, 1.58 mmol) was added and the reaction mixture was allowed to warm up overnight. The reaction was quenched with H$_2$O. The aqueous layer was extracted with EtOAc. The organic layer was dried (MgSO$_4$), filtered, concentrated, and purified by SiO$_2$ chromatography (24 g SiO$_2$, hexanes/EtOAc 0-35% EtOAc) to give 340 mg of 2-bromo-7-methyl-5-(2-trimethylsilanyl-ethoxymethyl)-5H-pyrrolo[2,3-b]pyrazine as a yellow liquid (77% yield).

Step 4: 2-Bromo-7-methyl-5-(2-trimethylsilanyl-ethoxymethyl)-5H-pyrrolo[2,3-b]pyrazine (0.346 g, 1.01 mmol), benzhydrylideneamine (0.19 mL, 1.11 mmol), Cs$_2$CO$_3$ (658 mg, 2.02 mmol), Pd(OAc)$_2$ (23 mg, 0.101 mmol) and BINAP (63 mg, 0.101 mmol) were dissolved in THF (10 mL) and heated at 100° C. for 63 hr, cooled to RT, partitioned between EtOAc and brine. The organic layer was dried (MgSO$_4$), filtered, concentrated, and purified by SiO$_2$ chromatography (40 g SiO$_2$, hexanes/EtOAc 0-35% EtOAc) to give 158 mg of benzhydrylidene-[7-methyl-5-(2-trimethylsilanyl-ethoxymethyl)-5H-pyrrolo[2,3-b]pyrazin-2-yl]-amine as a yellow liquid (20% yield).

Step 5: Benzhydrylidene-[7-methyl-5-(2-trimethylsilanyl-ethoxymethyl)-5H-pyrrolo[2,3-b]pyrazin-2-yl]-amine (91 mg, 0.206 mmol), NaOAc (41 mg, 0.494 mmol) and NH$_2$OH HCl (26 mg, 0.371 mmol) were dissolved in MeOH (2 mL) and stirred at RT overnight, and partitioned between EtOAc and brine. The organic layer was dried (MgSO$_4$), filtered, concentrated, and purified by SiO$_2$ chromatography (12 g SiO$_2$, hexanes/EtOAc 0-90% EtOAc) to give 41 mg of 7-methyl-5-(2-trimethylsilanyl-ethoxymethyl)-5H-pyrrolo[2,3-b]pyrazin-2-ylamine as a yellow solid (71% yield).

Step 6: 7-Methyl-5-(2-trimethylsilanyl-ethoxymethyl)-5H-pyrrolo[2,3-b]pyrazin-2-ylamine (41 mg, 0.147 mmol) was dissolved in 1,2-dichloroethane (1.5 mL). Cyclohexyl-isocyanate (0.19 mL, 1.47 mmol) was added and the reaction mixture was heated to reflux for 64 hr, cooled to RT, concentrated, purified by SiO$_2$ chromatography (8 g SiO$_2$, hexanes/EtOAc 0-50% EtOAc) to give 38 mg of 1-cyclohexyl-3-[7-methyl-5-(2-trimethylsilanyl-ethoxymethyl)-5H-pyrrolo[2,3-b]pyrazin-2-yl]-urea as a white solid (64% yield).

Step 7: 1-Cyclohexyl-3-[7-methyl-5-(2-trimethylsilanyl-ethoxymethyl)-5H-pyrrolo[2,3-b]pyrazin-2-yl]-urea (38 mg, 0.094 mmol) was dissolved in a solution of HCl in AcOH (1M, 1.9 mL), and heated at 50° C. in the sealed tube overnight. The reaction mixture was concentrated to dryness, dissolved in 1 mL of MeOH:H$_2$O:Et$_3$N 8:1:1 and ethylenediamine (63 ul, 0.94 mmol) was added. The reaction mixture was stirred overnight, concentrated and purified by SiO$_2$ chromatography (8 g SiO$_2$, DCM/MeOH 0-5% MeOH) to give 7 mg of 1-cyclohexyl-3-(7-methyl-5H-pyrrolo[2,3-b]pyrazin-2-yl)-urea as a white solid (27% yield).

Example 28

Synthesis of 1-(7-Chloro-5H-pyrrolo[2,3-b]pyrazin-2-yl)-3-cyclohexyl-urea

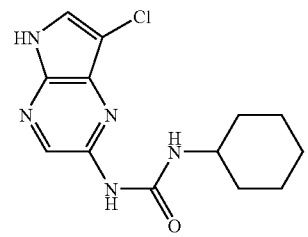

Step 1: To a solution of 2-bromo-5H-pyrrolo[2,3-b]pyrazine (1.8 g, 9.09 mmol) in 18 mL of DCM and 18 mL of DMF was added NCS (1.46 g, 10.9 mmol) at RT. The reaction mixture was stirred at RT overnight, then partitioned between EtOAc and brine. The organic layer was dried (MgSO$_4$) concentrated to give 2.98 g of impure 2-bromo-7-chloro-5H-pyrrolo[2,3-b]pyrazine as a yellow oil which was used for the next step without any purification.

Step 2: impure 2-Bromo-7-chloro-5H-pyrrolo[2,3-b]pyrazine was dissolved in DMF (30 mL). NaH (60%, 436 mg, 10.9 mmol) was added slowly. After the addition was complete stirring was continued for 30 minutes at RT. (2-Chloromethoxy-ethyl)-trimethyl-silane (1.9 mL, 10.9 mmol) was added and the reaction mixture was allowed to warm up overnight. The reaction was quenched with H$_2$O. The aqueous layer was extracted with EtOAc. The organic layer was dried (MgSO$_4$), filtered, concentrated, and purified by SiO$_2$ chromatography (24 g SiO$_2$, hexanes/EtOAc 0-35% EtOAc) to give 2.62 g of 2-bromo-7-chloro-5-(2-trimethylsilanyl-ethoxymethyl)-5H-pyrrolo[2,3-b]pyrazine as a yellow liquid (79% yield for 2 steps).

Step 3: 2-Bromo-7-chloro-5-(2-trimethylsilanyl-ethoxymethyl)-5H-pyrrolo[2,3-b]pyrazine (1.31 g, 3.61 mmol), benzhydrylideneamine (0.67 mL, 3.97 mmol), Cs$_2$CO$_3$ (2.35 g, 7.22 mmol), Pd(OAc)$_2$ (81 mg, 0.361 mmol) and BINAP (225 mg, 0.361 mmol) were dissolved in THF (36 mL) and heated at 100° C. overnight, cooled to RT, partitioned between EtOAc and brine. The organic layer was dried (MgSO$_4$), filtered, concentrated, and purified by SiO$_2$ chromatography (150 g SiO$_2$, hexanes/EtOAc 0-25% EtOAc) to give 992 mg of benzhydrylidene-[7-chloro-5-(2-trimethylsilanyl-ethoxymethyl)-5H-pyrrolo[2,3-b]pyrazin-2-yl]-amine as a yellow liquid (59% yield).

Step 4: Benzhydrylidene-[7-chloro-5-(2-trimethylsilanyl-ethoxymethyl)-5H-pyrrolo[2,3-b]pyrazin-2-yl]-amine (992 mg, 2.14 mmol), NaOAc (421 mg, 5.14 mmol) and NH$_2$OH HCl (268 mg, 3.85 mmol) were dissolved in MeOH (21 mL) and stirred at RT overnight, and partitioned between EtOAc and H$_2$O. The organic layer was dried (MgSO$_4$), filtered, concentrated, and purified by SiO$_2$ chromatography (150 g SiO$_2$, hexanes/EtOAc 0 to 50% EtOAc) to give 202 mg of 7-chloro-5-(2-trimethylsilanyl-ethoxymethyl)-5H-pyrrolo[2,3-b]pyrazin-2-ylamine as a white solid (32% yield).

Step 5: 7-Chloro-5-(2-trimethylsilanyl-ethoxymethyl)-5H-pyrrolo[2,3-b]pyrazin-2-ylamine (100 mg, 0.335 mmol) was dissolved in 1,2-dichloroethane (3.4 mL). Cyclohexylisocyanate (0.43 mL, 3.35 mmol) was added and the reaction mixture was heated to reflux overnight, cooled to RT, and concentrated. The residue was dispersed in 3 mL of toluene, cyclohexylisocyanate (0.86 mL, 6.70 mmol) was added and the reaction mixture was heated to reflux overnight, and cooled to 0° C. The precipitates were filtered, washed with toluene and dried under high vacuum to give 44 mg of 1-cyclohexyl-3-[7-chloro-5-(2-trimethylsilanyl-ethoxymethyl)-5H-pyrrolo[2,3-b]pyrazin-2-yl]-urea as a white solid (31% yield).

Step 6: 1-Cyclohexyl-3-[7-chloro-5-(2-trimethylsilanyl-ethoxymethyl)-5H-pyrrolo[2,3-b]pyrazin-2-yl]-urea (44 mg, 0.104 mmol) was dissolved in a solution of HCl in AcOH (1M, 2.1 mL), and heated at 50° C. in the sealed tube overnight. The reaction mixture was concentrated to dryness, dissolved in 1 mL of MeOH:H$_2$O:Et$_3$N 8:1:1 and ethylenediamine (69 ul, 1.04 mmol) was added. The reaction mixture was stirred for 5 days, concentrated and purified by SiO$_2$ chromatography (8 g SiO$_2$, DCM/MeOH 0 to 10% MeOH) to give 5 mg of 1-cyclohexyl-3-(7-chloro-5H-pyrrolo[2,3-b]pyrazin-2-yl)-urea as a white solid (16% yield).

Example 29

Synthesis of 1-(7-isopropyl-5H-pyrrolo[2,3-b]pyrazin-2-yl)-3-cyclohexyl-urea

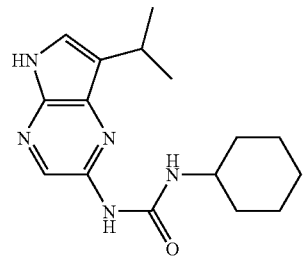

Step 1: 5-(2-Trimethylsilanyl-ethoxymethyl)-5H-pyrrolo[2,3-b]pyrazin-2-ylamine (1.32 g, 4.99 mmol) was dissolved in toluene (50 mL). Cyclohexylisocyanate (6.4 mL, 49.9 mmol) was added and the reaction mixture was heated to reflux for 88 hr, cooled to RT, and concentrated, and purified by SiO$_2$ chromatography (150 g SiO$_2$, DCM/MeOH 0 to 5% MeOH) to give 2.67 g of impure 1-cyclohexyl-3-[5-(2-trimethylsilanyl-ethoxymethyl)-5H-pyrrolo[2,3-b]pyrazin-2-yl]-urea as a yellow solid (31% yield).

Step 2: The mixture of 1-Cyclohexyl-3-[5-(2-trimethylsilanyl-ethoxymethyl)-5H-pyrrolo[2,3-b]pyrazin-2-yl]-urea (2.67 g) and NIS (742 mg, 3.30 mmol) in 12 mL of acetone was stirred at RT for 4 hr, filtered, and washed with small amount of acetone. The solid was dried under high vacuum to give 701 mg of 1-cyclohexyl-3-[7-iodo-5-(2-trimethylsilanyl-ethoxymethyl)-5H-pyrrolo[2,3-b]pyrazin-2-yl]-urea as an off-white solid (45% yield for 2 steps).

Step 3: 1-Cyclohexyl-3-[7-iodo-5-(2-trimethylsilanyl-ethoxymethyl)-5H-pyrrolo[2,3-b]pyrazin-2-yl]-urea (300 mg, 0.582 mmol), 2-isopropenyl-4,4,5,5-tetramethyl-[1,3,2]dioxaborolane (0.33 mL, 1.75 mmol), Cs$_2$CO$_3$ (948 mg, 2.91 mmol), and Pd(dppf)Cl$_2$ DCM complex (47 mg, 0.058 mmol) were dissolved in THF (2.3 mL) and H$_2$O (0.7 mL). The mixture was irradiated at 100° C. using microwave for 1 hr, cooled to RT, partitioned between EtOAc and brine. The organic layer was dried (MgSO$_4$), filtered, concentrated, and purified by SiO$_2$ chromatography (24 g SiO$_2$, DCM/MeOH 0 to 5% MeOH) to give 131 mg of impure 1-cyclohexyl-3-[7-isopropenyl-5-(2-trimethylsilanyl-ethoxymethyl)-5H-pyrrolo[2,3-b]pyrazin-2-yl]-urea as an off-white solid (52% yield).

Step 4: The mixture of 1-cyclohexyl-3-[7-isopropenyl-5-(2-trimethylsilanyl-ethoxymethyl)-5H-pyrrolo[2,3-b]pyrazin-2-yl]-urea (70 mg, 0.163 mmol) and Pd/C (17 mg, 0.016 mmol) in MeOH (1.6 mL) was shaken under 50 psi of H2 atmosphere overnight, filtered through a pad of celite, and washed with MeOH. The filtrate was concentrated to give crude 1-Cyclohexyl-3-[7-isopropyl-5-(2-trimethylsilanyl-ethoxymethyl)-5H-pyrrolo[2,3-b]pyrazin-2-yl]-urea, which was dissolved in a solution of HCl in AcOH (1M, 1.6 mL). The reaction mixture was heated at 50° C. in the sealed tube for 2 hr, concentrated to dryness, dissolved in 2 mL of MeOH:H$_2$O:Et$_3$N 8:1:1 and ethylenediamine (0.11 mL, 1.63 mmol) was added. The reaction mixture was stirred overnight, concentrated and purified by SiO$_2$ chromatography (8 g SiO$_2$, DCM/MeOH 0 to 10% MeOH) to give 9 mg of 1-cyclohexyl-3-(7-isopropyl-5H-pyrrolo[2,3-b]pyrazin-2-yl)-urea as a pale yellow solid (18% yield).

Example 30

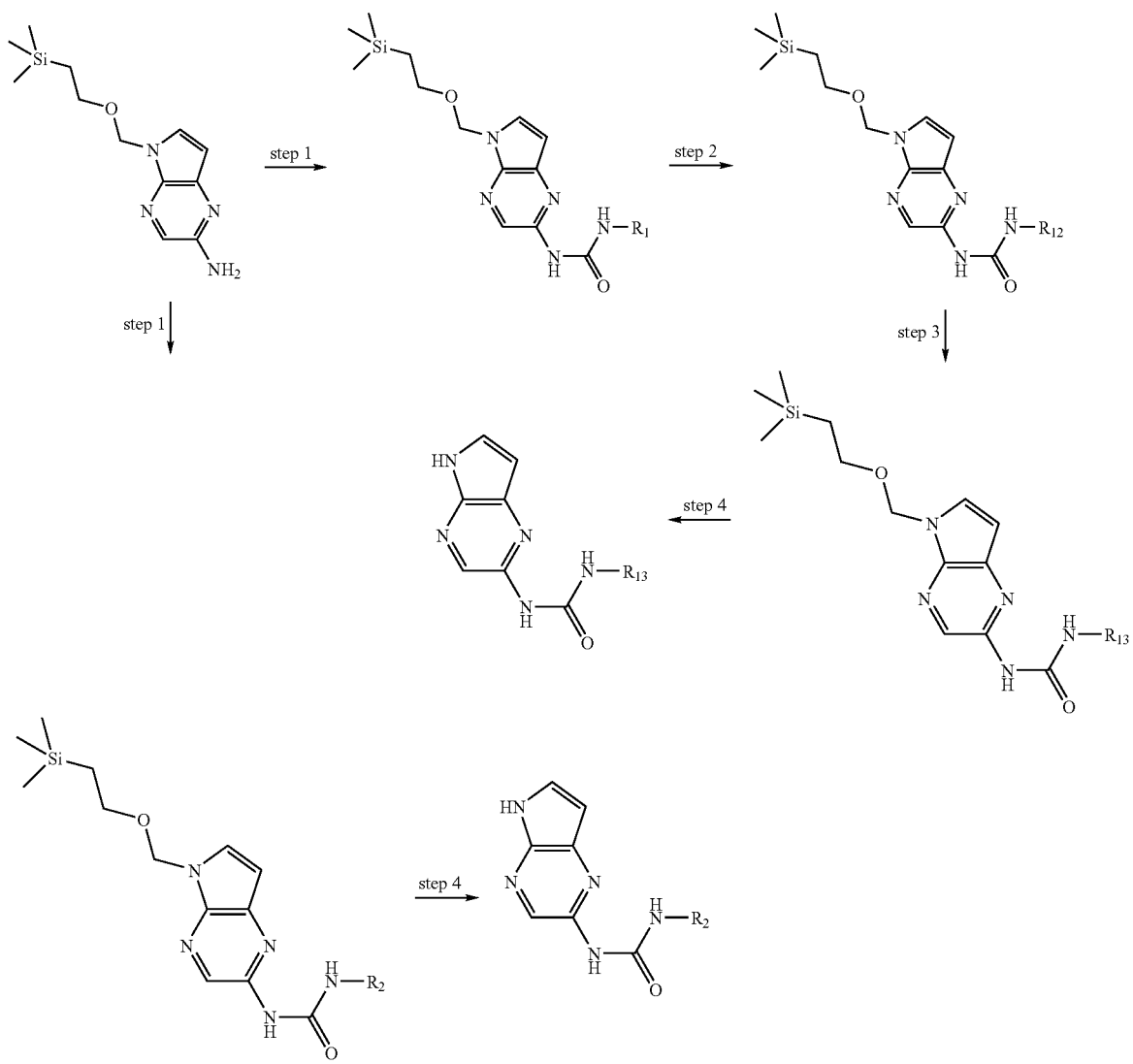

R₁ = protected azacyclic substituent
R₁₂ = deprotected azacyclic substituent
R₁₃ = alkylated, acylated, alkoxyacylated, or sulfonylated azacyclic substituent
R₂ = non-azacyclic susbtituent Step 1:

Variation A (S)-3-amino-piperidine-1-carboxylic acid tert-butyl ester (0.1 g, 0.378 mmol) was dissolved in DCM (3 mL). N,N-diisopropylethylamine (0.23 mL, 1.324 mmol) was added and the resulting light yellow solution was cooled by a NaCl/ice bath. After about 20 minutes phosgene 20% in toluene (0.24 mL, 0.454 mmol) was added. After about 20 minutes (1R,2S)-2-methyl-cyclohexylamine hydrochloride (0.068 g, 0.454 mmol) was added. The resulting mixture was stirred in the NaCl/ice bath for an hour. 1 mL of MeOH was added and the mixture was allowed to warm up to RT before being evaporated. The remaining oil was partitioned between DCM and H₂O. The aqueous layer was extracted twice with DCM, the organic layers were combined, dried over Na₂SO₄, filtered and evaporated. The residue was purified by SiO₂ chromatography (24 g SiO₂, DCM/(DCM:MeOH:NH₄OH 60:10:1) 100 to 83% DCM) to give 0.1 g of 1-((1R,2S)-2-methyl-cyclohexyl)-3-[5-(2-trimethylsilanyl-ethoxymethyl)-5H-pyrrolo[2,3-b]pyrazin-2-yl]-urea as a light brown solid (65% yield).

1-((1S,2R)-2-Methyl-cyclohexyl)-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and (1S,2R)-2-methyl-cyclohexylamine hydrochloride.

Racemic 1-(3,3-Dimethyl-cyclohexyl)-3-[5-(2-trimethyl-silanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and 3,3-dimethyl-cyclohexylamine hydrochloride.

Racemic 1-spiro[2.5]oct-5-yl-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and racemic spiro[2.5]oct-5-ylamine hydrochloride.

Racemic 1-(3-methyl-cyclohexyl)-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and racemic 3-methyl-cyclohexylamine.

Racemic cis 1-(6-methyl-spiro[2.5]oct-5-yl)-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and racemic cis 6-methyl-spiro[2.5]oct-5-ylamine hydrochloride.

Racemic cis 1-(2,5,5-trimethyl-cyclohexyl)-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and racemic cis 2,5,5-trimethyl-cyclohexylamine hydrochloride.

1-[1-(2,2,2-trifluoro-ethyl)-piperidin-3-yl]-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and racemic 1-(2,2,2-trifluoro-ethyl)-piperidin-3-ylamine hydrochloride.

(3R,5R)-3-Methyl-5-{3-[5-(2-trimethylsilanyl-ethoxymethyl)-5H-pyrrolo[2,3-b]pyrazin-2-yl]-ureido}-piperidine-1-carboxylic acid benzyl ester was prepared in the same manner from 5-(2-trimethylsilanyl-ethoxymethyl)-5H-pyrrolo[2,3-b]pyrazin-2-ylamine and (3R,5R)-3-amino-5-methyl-piperidine-1-carboxylic acid benzyl ester dihydro chloride.

1-(2,2-Dimethyl-cyclopentyl)-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and 2,2-dimethyl-cyclopentylamine (prepared according to *J. Med. Chem.* 2001, 44, 3764). In this instance, the reaction was run at −78° C.

Endo 1-bicyclo[2.2.1]hept-2-yl-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and endo bicycle[2.2.1]hept-2-ylamine hydrochloride. In this instance, the reaction was run at −78° C.

Exo 1-bicyclo[2.2.1]hept-2-yl-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and exo bicycle[2.2.1]hept-2-ylamine hydrochloride. In this instance, the reaction was run at −78° C.

1-(1-Methyl-cyclohexyl)-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and 1-methyl-cyclohexylamine hydrochloride. In this instance, the reaction was run at −78° C.

(R)-3-{3-[5-(2-Trimethylsilanyl-ethoxymethyl)-5H-pyrrolo[2,3-b]pyrazin-2-yl]-ureido}pyrrolidine-1-carboxylic acid tert-butyl ester was prepared in the same manner from 5-(2-trimethylsilanyl-ethoxymethyl)-5H-pyrrolo[2,3-b]pyrazin-2-ylamine and (R)-3-amino-pyrrolidine-1-carboxylic acid tert-butyl ester. In this instance, the reaction was run at −78° C.

Racemic trans 1-[3-(1,3-dioxo-1,3-dihydro-isoindol-2-yl)-cyclopentyl]-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and racemic trans 2-(3-amino-cyclopentyl)-5,6-dichloro-isoindole-1,3-dione. In this instance, the reaction was run at −78° C.

Racemic 3-{3-[5-(2-trimethylsilanyl-ethoxymethyl)-5H-pyrrolo[2,3-b]pyrazin-2-yl]-ureido}-azepane-1-carboxylic acid tert-butyl ester was prepared in the same manner from 5-(2-trimethylsilanyl-ethoxymethyl)-5H-pyrrolo[2,3-b]pyrazin-2-ylamine and racemic 3-amino-azepane-1-carboxylic acid tert-butyl ester. In this instance, the reaction was run at −78° C.

Example 31

Variation B

THF was used a solvent and the reaction was run at −78° C.

(R)-3-{3-[5-(2-Trimethylsilanyl-ethoxymethyl)-5H-pyrrolo[2,3-b]pyrazin-2-yl]-ureido}-piperidine-1-carboxylic acid tert-butyl ester was prepared this way from 5-(2-trimethylsilanyl-ethoxymethyl)-5H-pyrrolo[2,3-b]pyrazin-2-ylamine and (R)-3-amino-piperidine-1-carboxylic acid tert-butyl ester.

(S)-3-{3-[5-(2-Trimethylsilanyl-ethoxymethyl)-5H-pyrrolo[2,3-b]pyrazin-2-yl]-ureido}-piperidine-1-carboxylic acid tert-butyl ester was prepared this way from 5-(2-trimethylsilanyl-ethoxymethyl)-5H-pyrrolo[2,3-b]pyrazin-2-ylamine and (S)-3-amino-piperidine-1-carboxylic acid tert-butyl ester.

3-{3-[5-(2-Trimethylsilanyl-ethoxymethyl)-5H-pyrrolo[2,3-b]pyrazin-2-yl]-ureido}-piperidine-1-carboxylic acid tert-butyl ester was prepared this way from 5-(2-trimethylsilanyl-ethoxymethyl)-5H-pyrrolo[2,3-b]pyrazin-2-ylamine and 3-amino-piperidine-1-carboxylic acid tert-butyl ester.

Example 33

Variation C

No external base was used and the reaction was run at −78° C.

Racemic cis 1-(2-ethyl-cyclohexyl)-3-[5-(2-trimethylsilanyl-ethoxymethyl)-5H-pyrrolo[2,3-b]pyrazin-2-yl]-urea was prepared this way from 5-(2-trimethylsilanyl-ethoxymethyl)-5H-pyrrolo[2,3-b]pyrazin-2-ylamine and 2-ethyl-cyclohexylamine.

Racemic cis 1-(2-isopropyl-cyclohexyl)-3-[5-(2-trimethylsilanyl-ethoxymethyl)-5H-pyrrolo[2,3-b]pyrazin-2-yl]-urea was prepared this way from 5-(2-trimethylsilanyl-ethoxymethyl)-5H-pyrrolo[2,3-b]pyrazin-2-ylamine and 2-isopropyl-cyclohexylamine.

Racemic cis 1-(1-acetyl-3-methyl-piperidin-4-yl)-3-[5-(2-trimethylsilanyl-ethoxymethyl)-5H-pyrrolo[2,3-b]pyrazin-2-yl]-urea was prepared this way from 5-(2-trimethylsilanyl-ethoxymethyl)-5H-pyrrolo[2,3-b]pyrazin-2-ylamine and 1-(4-amino-3-methyl-piperidin-1-yl)-ethanone.

Racemic cis 1-(1-methanesulfonyl-3-methyl-piperidin-4-yl)-3-[5-(2-trimethylsilanyl-ethoxymethyl)-5H-pyrrolo[2,3-b]pyrazin-2-yl]-urea was prepared this way from 5-(2-trimethylsilanyl-ethoxymethyl)-5H-pyrrolo[2,3-b]pyrazin-2-ylamine and 1-methanesulfonyl-3-methyl-piperidin-4-ylamine.

Racemic cis 3-methyl-4-{3-[5-(2-trimethylsilanyl-ethoxymethyl)-5H-pyrrolo[2,3-b]pyrazin-2-yl]-ureido}-piperidine-1-carboxylic acid methyl ester was prepared this way from 5-(2-trimethylsilanyl-ethoxymethyl)-5H-pyrrolo[2,3-b]pyrazin-2-ylamine and 4-amino-3-methyl-piperidine-1-carboxylic acid methyl ester.

Racemic cis 1-(2-methyl-cycloheptyl)-3-[5-(2-trimethylsilanyl-ethoxymethyl)-5H-pyrrolo[2,3-b]pyrazin-2-yl]-urea was prepared this way from 5-(2-trimethylsilanyl-ethoxymethyl)-5H-pyrrolo[2,3-b]pyrazin-2-ylamine and 2-methyl-cycloheptylamine.

Racemic cis 1-(1-acetyl-5-methyl-azepan-4-yl)-3-[5-(2-trimethylsilanyl-ethoxymethyl)-5H-pyrrolo[2,3-b]pyrazin-2-yl]-urea was prepared this way from 5-(2-trimethylsilanyl-ethoxymethyl)-5H-pyrrolo[2,3-b]pyrazin-2-ylamine and 1-(4-amino-5-methyl-azepan-1-yl)-ethanone.

Racemic cis 4-methyl-5-{3-[5-(2-trimethylsilanyl-ethoxymethyl)-5H-pyrrolo[2,3-b]pyrazin-2-yl]-ureido}-azepane-1-carboxylic acid tert-butyl ester was prepared this way from 5-(2-trimethylsilanyl-ethoxymethyl)-5H-pyrrolo[2,3-b]pyrazin-2-ylamine and 4-amino-5-methyl-azepane-1-carboxylic acid tert-butyl ester.

Pyridin-2-ylmethyl-3-[5-(2-trimethylsilanyl-ethoxymethyl)-5H-pyrrolo[2,3-b]pyrazin-2-yl]-urea was prepared this way from 5-(2-trimethylsilanyl-ethoxymethyl)-5H-pyrrolo[2,3-b]pyrazin-2-ylamine and pyridin-2-yl-methylamine.

Pyridin-3-ylmethyl-3-[5-(2-trimethylsilanyl-ethoxymethyl)-5H-pyrrolo[2,3-b]pyrazin-2-yl]-urea was prepared this way from 5-(2-trimethylsilanyl-ethoxymethyl)-5H-pyrrolo[2,3-b]pyrazin-2-ylamine and pyridin-3-yl-methylamine.

1-(2-Pyridin-2-yl-ethyl)-3-[5-(2-trimethylsilanyl-ethoxymethyl)-5H-pyrrolo[2,3-b]pyrazin-2-yl]-urea was prepared this way from 5-(2-trimethylsilanyl-ethoxymethyl)-5H-pyrrolo[2,3-b]pyrazin-2-ylamine and 2-pyridin-2-yl-ethylamine.

1-(2-Pyridin-3-yl-ethyl)-3-[5-(2-trimethylsilanyl-ethoxymethyl)-5H-pyrrolo[2,3-b]pyrazin-2-yl]-urea was prepared this way from 5-(2-trimethylsilanyl-ethoxymethyl)-5H-pyrrolo[2,3-b]pyrazin-2-ylamine and 2-pyridin-3-yl-ethylamine.

Racemic 2-{3-[5-(2-trimethylsilanyl-ethoxymethyl)-5H-pyrrolo[2,3-b]pyrazin-2-yl]-ureidomethyl}-piperidine-1-carboxylic acid tert-butyl ester was prepared this way from 5-(2-trimethylsilanyl-ethoxymethyl)-5H-pyrrolo[2,3-b]pyrazin-2-ylamine and 2-aminomethyl-piperidine-1-carboxylic acid tert-butyl ester.

Racemic 2-(2-{3-[5-(2-trimethylsilanyl-ethoxymethyl)-5H-pyrrolo[2,3-b]pyrazin-2-yl]-ureido}-ethyl)-piperidine-1-carboxylic acid tert-butyl ester was prepared this way from 5-(2-trimethylsilanyl-ethoxymethyl)-5H-pyrrolo[2,3-b]pyrazin-2-ylamine and 2-(2-amino-ethyl)-piperidine-1-carboxylic acid tert-butyl ester.

Racemic 3-{3-[5-(2-trimethylsilanyl-ethoxymethyl)-5H-pyrrolo[2,3-b]pyrazin-2-yl]-ureidomethyl}-piperidine-1-carboxylic acid tert-butyl ester was prepared this way from 5-(2-trimethylsilanyl-ethoxymethyl)-5H-pyrrolo[2,3-b]pyrazin-2-ylamine and 3-aminomethyl-piperidine-1-carboxylic acid tert-butyl ester.

Racemic 3-(2-{3-[5-(2-trimethylsilanyl-ethoxymethyl)-5H-pyrrolo[2,3-b]pyrazin-2-yl]-ureido}-ethyl)-piperidine-1-carboxylic acid tert-butyl ester was prepared this way from 5-(2-trimethylsilanyl-ethoxymethyl)-5H-pyrrolo[2,3-b]pyrazin-2-ylamine and 3-(2-amino-ethyl)-piperidine-1-carboxylic acid tert-butyl ester.

3-{3-[5-(2-Trimethylsilanyl-ethoxymethyl)-5H-pyrrolo[2,3-b]pyrazin-2-yl]-ureidomethyl}-piperidine-1-carboxylic acid tert-butyl ester was prepared this way from 5-(2-trimethylsilanyl-ethoxymethyl)-5H-pyrrolo[2,3-b]pyrazin-2-ylamine and 4-aminomethyl-piperidine-1-carboxylic acid tert-butyl ester.

3-(2-{3-[5-(2-Trimethylsilanyl-ethoxymethyl)-5H-pyrrolo[2,3-b]pyrazin-2-yl]-ureido}-ethyl)-piperidine-1-carboxylic acid tert-butyl ester was prepared this way from 5-(2-trimethylsilanyl-ethoxymethyl)-5H-pyrrolo[2,3-b]pyrazin-2-ylamine and 4-(2-amino-ethyl)-piperidine-1-carboxylic acid tert-butyl ester.

Racemic 3-{3-[5-(2-trimethylsilanyl-ethoxymethyl)-5H-pyrrolo[2,3-b]pyrazin-2-yl]-ureidomethyl}-pyrrolidine-1-carboxylic acid tert-butyl ester was prepared this way from 5-(2-trimethylsilanyl-ethoxymethyl)-5H-pyrrolo[2,3-b]pyrazin-2-ylamine and 3-aminomethyl-pyrrolidine-1-carboxylic acid tert-butyl ester.

Racemic 2-{3-[5-(2-trimethylsilanyl-ethoxymethyl)-5H-pyrrolo[2,3-b]pyrazin-2-yl]-ureidomethyl}-pyrrolidine-1-carboxylic acid tert-butyl ester was prepared this way from 5-(2-trimethylsilanyl-ethoxymethyl)-5H-pyrrolo[2,3-b]pyrazin-2-ylamine and 2-aminomethyl-pyrrolidine-1-carboxylic acid tert-butyl ester.

Racemic 2-(2-{3-[5-(2-trimethylsilanyl-ethoxymethyl)-5H-pyrrolo[2,3-b]pyrazin-2-yl]-ureido}-ethyl)-pyrrolidine-1-carboxylic acid tert-butyl ester was prepared this way from 5-(2-trimethylsilanyl-ethoxymethyl)-5H-pyrrolo[2,3-b]pyrazin-2-ylamine and 2-(2-amino-ethyl)-pyrrolidine-1-carboxylic acid tert-butyl ester.

Example 34

Variation D

A 1:1 mixture of DCM:THF was used as solvent and the reaction was run at −40° C.

1-((3R,5R)-1-Acetyl-5-methyl-piperidin-3-yl)-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and 1-((3R,5R)-3-Amino-5-methyl-piperidin-1-yl)-ethanone 4-{3-[5-(2-Trimethylsilanyl-ethoxymethyl)-5H-pyrrolo[2,3-b]pyrazin-2-yl]-ureido}-piperidine-1-carboxylic acid tert-butyl ester was prepared in the same manner from 5-(2-trimethylsilanyl-ethoxymethyl)-5H-pyrrolo[2,3-b]pyrazin-2-ylamine and 4-amino-piperidine-1-carboxylic acid tert-butyl ester.

Racemic trans acetic acid-3-{3-[5-(2-trimethylsilanyl-ethoxymethyl)-5H-pyrrolo[2,3-b]pyrazin-2-yl]-ureido}-cyclohexylmethyl ester was prepared in the same manner from 5-(2-trimethylsilanyl-ethoxymethyl)-5H-pyrrolo[2,3-b]pyrazin-2-ylamine and racemic trans acetic acid 3-amino-cyclohexylmethyl ester.

(S)-3-{3-[5-(2-Trimethylsilanyl-ethoxymethyl)-5H-pyrrolo[2,3-b]pyrazin-2-yl]-ureido}-piperidine-1-carboxylic acid tert-butyl ester was prepared in the same manner from 5-(2-trimethylsilanyl-ethoxymethyl)-5H-pyrrolo[2,3-b]pyrazin-2-ylamine and (S)-3-amino-piperidine-1-carboxylic acid tert-butyl ester.

(S)-3-{3-[5-(2-Trimethylsilanyl-ethoxymethyl)-5H-pyrrolo[2,3-b]pyrazin-2-yl]-ureido}-pyrrolidine-1-carboxylic acid tert-butyl ester was prepared in the same manner from 5-(2-trimethylsilanyl-ethoxymethyl)-5H-pyrrolo[2,3-b]pyrazin-2-ylamine and (S)-3-amino-pyrrolidine-1-carboxylic acid tert-butyl ester.

3-{3-[5-(2-Trimethylsilanyl-ethoxymethyl)-5H-pyrrolo[2,3-b]pyrazin-2-yl]-ureido}-azepane-1-carboxylic acid tert-butyl ester was prepared in the same manner from 5-(2- trimethylsilanyl-ethoxymethyl)-5H-pyrrolo[2,3-b]pyrazin-2-ylamine and 3-amino-azepane-1-carboxylic acid tert-butyl ester.

(3S,5S)-3-Methyl-5-{3-[5-(2-trimethylsilanyl-ethoxymethyl)-5H-pyrrolo[2,3-b]pyrazin-2-yl]-ureido}-piperidine-1-carboxylic acid benzyl ester was prepared in the same manner from 5-(2-trimethylsilanyl-ethoxymethyl)-5H-pyrrolo[2,3-b]pyrazin-2-ylamine and (3S,5S)-3-amino-5-methyl-piperidine-1-carboxylic acid benzyl ester hydrochloride.

(3R,5R)-3-Methyl-5-{3-[5-(2-trimethylsilanyl-ethoxymethyl)-5H-pyrrolo[2,3-b]pyrazin-2-yl]-ureido}-piperidine-1-carboxylic acid benzyl ester was prepared in the same manner from 5-(2-trimethylsilanyl-ethoxymethyl)-5H-pyrrolo[2,3-b]pyrazin-2-ylamine and (3R,5R)-3-amino-5-methyl-piperidine-1-carboxylic acid benzyl ester hydrochloride.

4-{3-[5-(2-Trimethylsilanyl-ethoxymethyl)-5H-pyrrolo[2,3-b]pyrazin-2-yl]-ureido}-azepane-1-carboxylic acid tert-butyl ester was prepared in the same manner from 5-(2-trimethylsilanyl-ethoxymethyl)-5H-pyrrolo[2,3-b]pyrazin-2-ylamine and 4-amino-azepane-1-carboxylic acid tert-butyl ester.

Racemic trans-1-(3-methoxymethyl-cyclohexyl)-3-[5-(2-trimethylsilanyl-ethoxymethyl)-5H-pyrrolo[2,3-b]pyrazin-2-yl]-urea was prepared in the same manner from 5-(2-trimethylsilanyl-ethoxymethyl)-5H-pyrrolo[2,3-b]pyrazin-2-ylamine and racemic trans-3-methoxymethyl-cyclohexylamine.

(1S,3S)-3-{3-[5-(2-Trimethylsilanyl-ethoxymethyl)-5H-pyrrolo[2,3-b]pyrazin-2-yl]-ureido}-cyclopentanecarboxylic acid methyl ester was prepared in the same manner from 5-(2-trimethylsilanyl-ethoxymethyl)-5H-pyrrolo[2,3-b]pyrazin-2-ylamine and (1S,3S)-3-amino-cyclopentanecarboxylic acid methyl ester hydrochloride.

Racemic trans 3-{3-[5-(2-trimethylsilanyl-ethoxymethyl)-5H-pyrrolo[2,3-b]pyrazin-2-yl]-ureido}-cyclohexanecarboxylic acid dimethylamide was prepared in the same manner from 5-(2-trimethylsilanyl-ethoxymethyl)-5H-pyrrolo[2,3-b]pyrazin-2-ylamine and racemic trans 3-amino-cyclohexanecarboxylic acid dimethylamide hydrochloride.

Step 2, Boc-Deprotection:

(R)-3-{3-[5-(2-Trimethylsilanyl-ethoxymethyl)-5H-pyrrolo[2,3-b]pyrazin-2-yl]-ureido}-piperidine-1-carboxylic acid tert-butyl ester (0.238 g, 0.49 mmolL) was dissolved in 2.5 mL of MeOH and cooled to 0° C. Acetyl chloride (0.69 mL, 9.7 mmol) was added dropwise and when the addition was complete the reaction mixture was allowed to warm up to RT and stirred for 2 h. The solvent was removed under vacuum and the residue was treated with toluene and concentrated to dryness. This process was repeated twice more and at last the flask was left under high vacuum to give 1-(R)-piperidin-3-yl-3-[5-(2-trimethylsilanyl-ethoxymethyl)-5H-pyrrolo[2,3-b]pyrazin-2-yl]-urea dihydrochloride which was used as is in the following step.

1-(S)-Piperidin-3-yl-3-[5-(2-trimethylsilanyl-ethoxymethyl)-5H-pyrrolo[2,3-b]pyrazin-2-yl]-urea dihydrochloride was prepared in the same manner from (S)-3-{3-[5-(2-trimethylsilanyl-ethoxymethyl)-5H-pyrrolo[2,3-b]pyrazin-2-yl]-ureido}-piperidine-1-carboxylic acid tert-butyl ester.

Piperidin-3-yl-3-[5-(2-trimethylsilanyl-ethoxymethyl)-5H-pyrrolo[2,3-b]pyrazin-2-yl]-urea dihydrochloride was prepared in the same manner from 3-{3-[5-(2-trimethylsilanyl-ethoxymethyl)-5H-pyrrolo[2,3-b]pyrazin-2-yl]-ureido}-piperidine-1-carboxylic acid tert-butyl ester.

Piperidin-4-yl-3-[5-(2-trimethylsilanyl-ethoxymethyl)-5H-pyrrolo[2,3-b]pyrazin-2-yl]-urea dihydrochloride was prepared in the same manner from 4-{3-[5-(2-trimethylsilanyl-ethoxymethyl)-5H-pyrrolo[2,3-b]pyrazin-2-yl]-ureido}-piperidine-1-carboxylic acid tert-butyl ester.

1-(S)-Pyrrolidin-3-yl-3-[5-(2-trimethylsilanyl-ethoxymethyl)-5H-pyrrolo[2,3-b]pyrazin-2-yl]-urea dihydrochloride was prepared in the same manner from (S)-3-{3-[5-(2-trimethylsilanyl-ethoxymethyl)-5H-pyrrolo[2,3-b]pyrazin-2-yl]-ureido}-pyrrolidine-1-carboxylic acid tert-butyl ester.

Azepan-3-yl-3-[5-(2-trimethylsilanyl-ethoxymethyl)-5H-pyrrolo[2,3-b]pyrazin-2-yl]-urea dihydrochloride was prepared in the same manner from 3-{3-[5-(2-trimethylsilanyl-ethoxymethyl)-5H-pyrrolo[2,3-b]pyrazin-2-yl]-ureido}-azepan-1-carboxylic acid tert-butyl ester.

Azepan-4-yl-3-[5-(2-trimethylsilanyl-ethoxymethyl)-5H-pyrrolo[2,3-b]pyrazin-2-yl]-urea dihydrochloride was prepared in the same manner from 4-{3-[5-(2-trimethylsilanyl-ethoxymethyl)-5H-pyrrolo[2,3-b]pyrazin-2-yl]-ureido}-piperidine-1-carboxylic acid tert-butyl ester.

Racemic cis 1-(4-methyl-azepan-4-yl)-3-[5-(2-trimethylsilanyl-ethoxymethyl)-5H-pyrrolo[2,3-b]pyrazin-2-yl]-urea dihydrochloride was prepared in the same manner from 4-methyl-5-{3-[5-(2-trimethylsilanyl-ethoxymethyl)-5H-pyrrolo[2,3-b]pyrazin-2-yl]-ureido}-azepane-1-carboxylic acid tert-butyl ester. In this instance the reaction mixture was stirred at RT for 16 hours instead of 2 hours.

Racemic 1-piperidin-2-ylmethyl-3-[5-(2-trimethylsilanyl-ethoxymethyl)-5H-pyrrolo[2,3-b]pyrazin-2-yl]-urea dihydrochloride was prepared in the same manner from racemic 2-{3-[5-(2-trimethylsilanyl-ethoxymethyl)-5H-pyrrolo[2,3-b]pyrazin-2-yl]-ureidomethyl}-piperidine-1-carboxylic acid tert-butyl ester.

Racemic 1-piperidin-3-ylmethyl-3-[5-(2-trimethylsilanyl-ethoxymethyl)-5H-pyrrolo[2,3-b]pyrazin-2-yl]-urea dihydrochloride was prepared in the same manner from 3-{3-[5-(2-trimethylsilanyl-ethoxymethyl)-5H-pyrrolo[2,3-b]pyrazin-2-yl]-ureidomethyl}-piperidine-1-carboxylic acid tert-butyl ester. In this instance the reaction mixture was stirred at RT for 16 hours instead of 2 hours.

Racemic 1-piperidin-2-ylmethyl-3-[5-(2-trimethylsilanyl-ethoxymethyl)-5H-pyrrolo[2,3-b]pyrazin-2-yl]-urea dihydrochloride was prepared in the same manner from racemic 2-{3-[5-(2-trimethylsilanyl-ethoxymethyl)-5H-pyrrolo[2,3-b]pyrazin-2-yl]-ureidomethyl}-piperidine-1-carboxylic acid tert-butyl ester.

Racemic 1-(2-piperidin-3-yl-ethyl)-3-[5-(2-trimethylsilanyl-ethoxymethyl)-5H-pyrrolo[2,3-b]pyrazin-2-yl]-urea dihydrochloride was prepared in the same manner from racemic 3-(2-{3-[5-(2-trimethylsilanyl-ethoxymethyl)-5H-pyrrolo[2,3-b]pyrazin-2-yl]-ureido}-ethyl)-piperidine-1-carboxylic acid tert-butyl ester.

Piperidin-4-ylmethyl-3-[5-(2-trimethylsilanyl-ethoxymethyl)-5H-pyrrolo[2,3-b]pyrazin-2-yl]-urea dihydrochloride was prepared in the same manner from 4-{3-[5-(2-trimethylsilanyl-ethoxymethyl)-5H-pyrrolo[2,3-b]pyrazin-2-yl]-ureidomethyl}-piperidine-1-carboxylic acid tert-butyl ester. In this instance the reaction mixture was stirred at RT for 4 hours instead of 2 hours.

1-(2-Piperidin-4-yl-ethyl)-3-[5-(2-trimethylsilanyl-ethoxymethyl)-5H-pyrrolo[2,3-b]pyrazin-2-yl]-urea dihydrochloride was prepared in the same manner from 4-(2-{3-[5-(2-trimethylsilanyl-ethoxymethyl)-5H-pyrrolo[2,3-b]pyrazin-2-yl]-ureido}-ethyl)-piperidine-1-carboxylic acid tert-butyl ester.

Racemic 1-pyrrolidin-3-ylmethyl-3-[5-(2-trimethylsilanyl-ethoxymethyl)-5H-pyrrolo[2,3-b]pyrazin-2-yl]-urea dihydrochloride was prepared in the same manner from racemic 3-{3-[5-(2-trimethylsilanyl-ethoxymethyl)-5H-pyrrolo[2,3-b]pyrazin-2-yl]-ureidomethyl}-pyrrolidine-1-carboxylic acid tert-butyl ester.

Racemic 1-pyrrolidin-2-ylmethyl-3-[5-(2-trimethylsilanyl-ethoxymethyl)-5H-pyrrolo[2,3-b]pyrazin-2-yl]-urea dihydrochloride was prepared in the same manner from racemic 2-{3-[5-(2-trimethylsilanyl-ethoxymethyl)-5H-pyrrolo[2,3-b]pyrazin-2-yl]-ureidomethyl}-pyrrolidine-1-carboxylic acid tert-butyl ester. In this instance the reaction mixture was stirred at RT for 6 hours instead of 2 hours.

Racemic 1-(2-pyrrolidin-2-yl-ethyl)-3-[5-(2-trimethylsilanyl-ethoxymethyl)-5H-pyrrolo[2,3-b]pyrazin-2-yl]-urea dihydrochloride was prepared in the same manner from racemic 2-(2-{3-[5-(2-trimethylsilanyl-ethoxymethyl)-5H-pyrrolo[2,3-b]pyrazin-2-yl]-ureido}-ethyl)-pyrrolidine-1-carboxylic acid tert-butyl ester. In this instance the reaction mixture was stirred at RT for 6 hours instead of 2 hours.

1-(R)-Pyrrolidin-3-yl-3-[5-(2-trimethylsilanyl-ethoxymethyl)-5H-pyrrolo[2,3-b]pyrazin-2-yl]-urea dihydrochloride salt was prepared in the same manner from (R)-3-{3-[5-(2-trimethylsilanyl-ethoxymethyl)-5H-pyrrolo[2,3-b]pyrazin-2-yl]-ureido}pyrrolidine-1-carboxylic acid tert-butyl ester.

Racemic 1-azepan-3-yl-3-[5-(2-trimethylsilanyl-ethoxymethyl)-5H-pyrrolo[2,3-b]pyrazin-2-yl]-urea dihydrochloride was prepared in the same manner from 3-{3-[5-(2-trimethylsilanyl-ethoxymethyl)-5H-pyrrolo[2,3-b]pyrazin-2-yl]-ureido}-azepane-1-carboxylic acid tert-butyl ester.

Step 2, Cbz Deprotection:

A mixture of (3R,5R)-3-methyl-5-{3-[5-(2-trimethylsilanyl-ethoxymethyl)-5H-pyrrolo[2,3-b]pyrazin-2-yl]-ureido}-piperidine-1-carboxylic acid benzyl ester (1.04 g, 1.93 mmol) and palladium hydroxide 20% on carbon (0.15 g) in 20 mL of EtOH was stirred at RT under hydrogen (1 atm) for 2 hours before being filtered. The dark brown filtrate was evaporated to give 0.76 g of 1-((3R,5R)-5-methyl-piperidin-3-yl)-3-[5-(2-trimethylsilanyl-ethoxymethyl)-5H-pyrrolo[2,3-b]pyrazin-2-yl]-urea (>95%).

1-((3S,5S)-5-M ethyl-piperidin-3-yl)-3-[5-(2-trimethylsilanyl-ethoxymethyl)-5H-pyrrolo[2,3-b]pyrazin-2-yl]-urea was prepared in the same manner from (3S,5S)-3-methyl-5-{3-[5-(2-trimethylsilanyl-ethoxymethyl)-5H-pyrrolo[2,3-b]pyrazin-2-yl]-ureido}-piperidine-1-carboxylic acid benzyl ester.

Step 3, Acylation

Example 35

Variation A

Piperidin-4-yl-3-[5-(2-trimethylsilanyl-ethoxymethyl)-5H-pyrrolo[2,3-b]pyrazin-2-yl]-urea dihydrochloride (0.073 g, 0.158 mmol) was suspended in DCM (1 mL) and pyridine (0.045 mL, 0.55 mmol) was added. Acetic anhydride (0.018 mL, 0.19 mmol) was added and the resulting solution stirred at RT overnight. The solvent was evaporated. The remaining oil was purified by SiO$_2$ chromatography (12 g SiO$_2$, DCM:MeOH 0 to 5% MeOH) to give 0.053 g of 1-(1-acetyl-piperidin-4-yl)-3-[5-(2-trimethylsilanyl-ethoxymethyl)-5H-pyrrolo[2,3-b]pyrazin-2-yl]-urea as off-white foam (78% yield).

1-(1-Acetyl-piperidin-3-yl)-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride.

1-(1-Acetyl-azepan-4-yl)-3-[5-(2-trimethylsilanyl-ethoxymethyl)-5H-pyrrolo[2,3-b]pyrazin-2-yl]-urea was prepared in the same manner from 1-(azepan-4-yl)-3-[5-(2-trimethylsilanyl-ethoxymethyl)-5H-pyrrolo[2,3-b]pyrazin-2-yl]-urea dihydrochloride.

1-((S)-1-Acetyl-piperidin-3-yl)-3-[5-(2-trimethylsilanyl-ethoxymethyl)-5H-pyrrolo[2,3-b]pyrazin-2-yl]-urea was prepared in the same manner from 1-(S)-piperidin-3-yl-3-[5-(2-trimethylsilanyl-ethoxymethyl)-5H-pyrrolo[2,3-b]pyrazin-2-yl]-urea dihydrochloride.

1-((R)-1-acetyl-piperidin-3-yl)-3-[5-(2-trimethylsilanyl-ethoxymethyl)-5H-pyrrolo[2,3-b]pyrazin-2-yl]-urea was prepared in the same manner from 1-(R)-piperidin-3-yl-3-[5-(2-trimethylsilanyl-ethoxymethyl)-5H-pyrrolo[2,3-b]pyrazin-2-yl]-urea dihydrochloride.

1-((S)-1-Acetyl-pyrrolidin-3-yl)-3-[5-(2-trimethylsilanyl-ethoxymethyl)-5H-pyrrolo[2,3-b]pyrazin-2-yl]-urea was prepared in the same manner from 1-(S)-pyrrolidin-3-yl-3-[5-(2-trimethylsilanyl-ethoxymethyl)-5H-pyrrolo[2,3-b]pyrazin-2-yl]-urea dihydrochloride.

1-((3R,5R)-1-Acetyl-5-methyl-piperidin-3-yl)-3-[5-(2-trimethylsilanyl-ethoxymethyl)-5H-pyrrolo[2,3-b]pyrazin-2-yl]-urea was prepared in the same manner from 1-((3R,5R)-5-methyl-piperidin-3-yl)-3-[5-(2-trimethylsilanyl-ethoxymethyl)-5H-pyrrolo[2,3-b]pyrazin-2-yl]-urea dihydrochloride.

Racemic 1-(1-acetyl-piperidin-2-ylmethyl)-3-[5-(2-trimethylsilanyl-ethoxymethyl)-5H-pyrrolo[2,3-b]pyrazin-2-yl]-urea was prepared in the same manner from racemic 1-piperidin-2-ylmethyl-3-[5-(2-trimethylsilanyl-ethoxymethyl)-5H-pyrrolo[2,3-b]pyrazin-2-yl]-urea dihydrochloride.

Racemic 1-[2-(1-acetyl-piperidin-2-yl)-ethyl]-3-[5-(2-trimethylsilanyl-ethoxymethyl)-5H-pyrrolo[2,3-b]pyrazin-2-yl]-urea was prepared in the same manner from racemic 1-(2-piperidin-2-yl-ethyl)-3-[5-(2-trimethylsilanyl-ethoxymethyl)-5H-pyrrolo[2,3-b]pyrazin-2-yl]-urea dihydrochloride.

Racemic 1-(1-acetyl-piperidin-3-ylmethyl)-3-[5-(2-trimethylsilanyl-ethoxymethyl)-5H-pyrrolo[2,3-b]pyrazin-2-yl]-urea was prepared in the same manner from 1-piperidin-3-ylmethyl-3-[5-(2-trimethylsilanyl-ethoxymethyl)-5H-pyrrolo[2,3-b]pyrazin-2-yl]-urea dihydrochloride.

1-(1-Acetyl-piperidin-4-ylmethyl)-3-[5-(2-trimethylsilanyl-ethoxymethyl)-5H-pyrrolo[2,3-b]pyrazin-2-yl]-urea was prepared in the same manner from 1-piperidin-4-ylmethyl-3-[5-(2-trimethylsilanyl-ethoxymethyl)-5H-pyrrolo[2,3-b]pyrazin-2-yl]-urea dihydrochloride.

1-[2-(1-Acetyl-piperidin-4-yl)-ethyl]-3-[5-(2-trimethylsilanyl-ethoxymethyl)-5H-pyrrolo[2,3-b]pyrazin-2-yl]-urea was prepared in the same manner from 1-(2-piperidin-4-yl-ethyl)-3-[5-(2-trimethylsilanyl-ethoxymethyl)-5H-pyrrolo[2,3-b]pyrazin-2-yl]-urea dihydrochloride.

Racemic 1-(1-acetyl-pyrrolidin-2-ylmethyl)-3-[5-(2-trimethylsilanyl-ethoxymethyl)-5H-pyrrolo[2,3-b]pyrazin-2-yl]-urea was prepared in the same manner from 1-pyrrolidin-2-ylmethyl-3-[5-(2-trimethylsilanyl-ethoxymethyl)-5H-pyrrolo[2,3-b]pyrazin-2-yl]-urea dihydrochloride.

Racemic 1-[2-(1-acetyl-pyrrolidin-2-yl)-ethyl]-3-[5-(2-trimethylsilanyl-ethoxymethyl)-5H-pyrrolo[2,3-b]pyrazin-2-yl]-urea was prepared in the same manner from 1-(2-pyrrolidin-2-yl-ethyl)-3-[5-(2-trimethylsilanyl-ethoxymethyl)-5H-pyrrolo[2,3-b]pyrazin-2-yl]-urea dihydrochloride.

Example 36

Variation B

Piperidin-3-yl-3-[5-(2-trimethylsilanyl-ethoxymethyl)-5H-pyrrolo[2,3-b]pyrazin-2-yl]-urea (0.150 g, 0.38 mmol) was dissolved in 2 mL of DCM and pyridine was added (0.120 mL/1.54 mmol). Propionyl chloride (0.05 mL, 5.4 mmol) was added dropwise to the solution and the resulting mixture was stirred overnight at RT. The reaction mixture was diluted with DCM and was quenched by addition of saturated solution of NaHCO$_3$. The aqueous layer was extracted once with DCM and the combined organics were dried (MgSO4), filtered and, concentrated. The crude was purified by SiO$_2$ chromatography using DCM/(DCM:MeOH:NH$_4$OH; 60:10:1) 75% DCM) to give 0.130 g of 1-(1-propionyl-piperidin-3-yl)-3-[5-(2-trimethylsilanyl-ethoxymethyl)-5H-pyrrolo[2,3-b]pyrazin-2-yl]-urea (76% yield).

1-(1-Isobutyryl-piperidin-3-yl)-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and isobutyryl chloride.

1-[1-(3-M ethyl-butyryl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and isovaleryl chloride.

1-(1-Cyclopropanecarbonyl-piperidin-3-yl)-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and cyclopropanecarbonyl chloride. DIPEA was used as base instead of pyridine.

1-[1-(2-Cyclopropyl-acetyl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and cyclopropyl-acetyl chloride. DIPEA was used as base instead of pyridine.

Racemic 1-(1-acetyl-azepan-3-yl)-3-[5-(2-trimethylsilanyl-ethoxymethyl)-5H-pyrrolo[2,3-b]pyrazin-2-yl]-urea was prepared in the same manner from racemic 1-azepan-3-yl-3-[5-(2-trimethylsilanyl-ethoxymethyl)-5H-pyrrolo[2,3-b]pyrazin-2-yl]-urea dihydrochloride and acetyl chloride.

1-((R)-1-Acetyl-pyrrolidin-3-yl)-3-[5-(2-trimethylsilanyl-ethoxymethyl)-5H-pyrrolo[2,3-b]pyrazin-2-yl]-urea was prepared in the same manner from 1-(R)-pyrrolidin-3-yl-3-[5-(2-trimethylsilanyl-ethoxymethyl)-5H-pyrrolo[2,3-b]pyrazin-2-yl]-urea dihydrochloride and acetyl chloride.

Example 37

Variation C

DIPEA (0.082 mL, 0.47 mmol) was added at RT to a mixture of 1-piperidin-3-yl-3-[5-(2-trimethylsilanyl-ethoxymethyl)-5H-pyrrolo[2,3-b]pyrazin-2-yl]-urea dihydrochloride (0.066 g, 0.142 mmol), 3,3,3-trifluoropropionic acid (0.015 mL, 0.171 mmol), EDCI (0.033 g, 0.171 mmol), HOBt monohydrate (0.026 g, 0.171 mmol) in 1 mL of DCM. The resulting mixture was stirred at RT for 24 hours before being partitioned between H$_2$O and DCM. The aqueous layer was back extracted twice with DCM. The combined organic layers were dried (Na$_2$SO$_4$), filtered, and evaporated. The residue was purified by SiO$_2$ flash chromatography (DCM/(DCM:MeOH:NH$_4$OH 60:10:1] 80% DCM) to give 0.04 g of 1-[1-(3,3,3-trifluoro-propionyl)-piperidin-3-yl]-3-[5-(2-trimethylsilanyl-ethoxymethyl)-5H-pyrrolo[2,3-b]pyrazin-2-yl]-urea (56% yield).

1-[1-(2-Cyano-acetyl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and cyanoacetic acid.

Example 38

Step 3. Alkoxyacylation

Piperidin-4-yl-3-[5-(2-trimethylsilanyl-ethoxymethyl)-5H-pyrrolo[2,3-b]pyrazin-2-yl]-urea dihydrochloride (0.07 g, 0.151 mmol) was suspended in DCM (1.5 mL) and N,N-diisopropylethylamine (0.1 mL, 0.6 mmol) was added. Methyl chloroformate (0.018 mL, 0.227 mmol) was added and the resulting solution stirred at RT. After 4 hours the solvent was evaporated. The remaining oil was purified by SiO$_2$ chromatography (11 g SiO$_2$, DCM/MeOH 0-4% MeOH). Obtained 0.052 g of 4-{3-[5-(2-trimethylsilanyl-ethoxymethyl)-5H-pyrrolo[2,3-b]pyrazin-2-yl]-ureido}-piperidine-1-carboxylic acid methyl ester as light brown foam (76% yield).

3-{3-[5-(2-Trimethylsilanyl-ethoxymethyl)-5H-pyrrolo[2,3-b]pyrazin-2-yl]-ureido}-piperidine-1-carboxylic acid methyl ester was prepared in the same manner from 1-piperidin-3-yl-3-[5-(2-trimethylsilanyl-ethoxymethyl)-5H-pyrrolo[2,3-b]pyrazin-2-yl]-urea dihydrochloride.

4-{3-[5-(2-Trimethylsilanyl-ethoxymethyl)-5H-pyrrolo[2,3-b]pyrazin-2-yl]-ureido}-azepane-1-carboxylic acid methyl ester was prepared in the same manner from 1-azepan-4-yl-3-[5-(2-trimethylsilanyl-ethoxymethyl)-5H-pyrrolo[2,3-b]pyrazin-2-yl]-urea dihydrochloride.

3-{3-[5-(2-Trimethylsilanyl-ethoxymethyl)-5H-pyrrolo[2,3-b]pyrazin-2-yl]-ureido}-piperidine-1-carboxylic acid ethyl ester was prepared in the same manner from 1-piperidin-3-yl-3-[5-(2-trimethylsilanyl-ethoxymethyl)-5H-pyrrolo[2,3-b]pyrazin-2-yl]-urea dihydrochloride.

(S)-3-{3-[5-(2-Trimethylsilanyl-ethoxymethyl)-5H-pyrrolo[2,3-b]pyrazin-2-yl]-ureido}-pyrrolidine-1-carboxylic acid methyl ester was prepared in the same manner from 1-(S)-pyrrolidin-3-yl-3-[5-(2-trimethylsilanyl-ethoxymethyl)-5H-pyrrolo[2,3-b]pyrazin-2-yl]-urea trihydrochloride.

Racemic cis 4-methyl-5-{3-[5-(2-trimethylsilanyl-ethoxymethyl)-5H-pyrrolo[2,3-b]pyrazin-2-yl]-ureido}-azepane-1-carboxylic acid methyl ester was prepared in the same manner from racemic cis 1-(5-methyl-azepan-4-yl)-3-[5-(2-trimethylsilanyl-ethoxymethyl)-5H-pyrrolo[2,3-b]pyrazin-2-yl]-urea dihydrochloride.

Racemic 2-{3-[5-(2-trimethylsilanyl-ethoxymethyl)-5H-pyrrolo[2,3-b]pyrazin-2-yl]-ureidomethyl}-piperidine-1-carboxylic acid methyl ester was prepared in the same manner from racemic 1-piperidin-2-ylmethyl-3-[5-(2-trimethylsilanyl-ethoxymethyl)-5H-pyrrolo[2,3-b]pyrazin-2-yl]-urea dihydrochloride.

Racemic 2-(2-{3-[5-(2-trimethylsilanyl-ethoxymethyl)-5H-pyrrolo[2,3-b]pyrazin-2-yl]-ureido}-ethyl)-piperidine-1-carboxylic acid methyl ester was prepared in the same manner from racemic 1-(2-piperidin-2-yl-ethyl)-3-[5-(2-trimethylsilanyl-ethoxymethyl)-5H-pyrrolo[2,3-b]pyrazin-2-yl]-urea dihydrochloride.

Racemic 3-{3-[5-(2-trimethylsilanyl-ethoxymethyl)-5H-pyrrolo[2,3-b]pyrazin-2-yl]-ureidomethyl}-piperidine-1- carboxylic acid methyl ester was prepared in the same manner from racemic 1-piperidin-3-ylmethyl-3-[5-(2-trimethylsilanyl-ethoxymethyl)-5H-pyrrolo[2,3-b]pyrazin-2-yl]-urea dihydrochloride.

4-{3-[5-(2-Trimethylsilanyl-ethoxymethyl)-5H-pyrrolo[2,3-b]pyrazin-2-yl]-ureidomethyl}-piperidine-1-carboxylic acid methyl ester was prepared in the same manner from 1-piperidin-4-ylmethyl-3-[5-(2-trimethylsilanyl-ethoxymethyl)-5H-pyrrolo[2,3-b]pyrazin-2-yl]-urea dihydrochloride.

4-(2-{3-[5-(2-Trimethylsilanyl-ethoxymethyl)-5H-pyrrolo[2,3-b]pyrazin-2-yl]-ureido}-ethyl)-piperidine-1-carboxylic acid methyl ester was prepared in the same manner from 1-(2-piperidin-4-yl-ethyl)-3-[5-(2-trimethylsilanyl-ethoxymethyl)-5H-pyrrolo[2,3-b]pyrazin-2-yl]-urea dihydrochloride.

Racemic 3-{3-[5-(2-trimethylsilanyl-ethoxymethyl)-5H-pyrrolo[2,3-b]pyrazin-2-yl]-ureidomethyl}-pyrrolidine-1-carboxylic acid methyl ester was prepared in the same manner from 1-pyrrolidin-3-ylmethyl-3-[5-(2-trimethylsilanyl-ethoxymethyl)-5H-pyrrolo[2,3-b]pyrazin-2-yl]-urea dihydrochloride.

Racemic 2-{3-[5-(2-trimethylsilanyl-ethoxymethyl)-5H-pyrrolo[2,3-b]pyrazin-2-yl]-ureidomethyl}-pyrrolidine-1-carboxylic acid methyl ester was prepared in the same manner from racemic 1-pyrrolidin-2-ylmethyl-3-[5-(2-trimethylsilanyl-ethoxymethyl)-5H-pyrrolo[2,3-b]pyrazin-2-yl]-urea dihydrochloride.

Racemic 2-(2-{3-[5-(2-trimethylsilanyl-ethoxymethyl)-5H-pyrrolo[2,3-b]pyrazin-2-yl]-ureido}-ethyl)-pyrrolidine-1-carboxylic acid methyl ester was prepared in the same manner from racemic 1-(2-pyrrolidin-2-yl-ethyl)-3-[5-(2-trimethylsilanyl-ethoxymethyl)-5H-pyrrolo[2,3-b]pyrazin-2-yl]-urea dihydrochloride.

Racemic 3-{3-[5-(2-trimethylsilanyl-ethoxymethyl)-5H-pyrrolo[2,3-b]pyrazin-2-yl]-ureido}-azepane-1-carboxylic acid methyl ester was prepared in the same manner from racemic 1-azepan-3-yl-3-[5-(2-trimethylsilanyl-ethoxymethyl)-5H-pyrrolo[2,3-b]pyrazin-2-yl]-urea dihydrochloride.

(R)-3-{3-[5-(2-Trimethylsilanyl-ethoxymethyl)-5H-pyrrolo[2,3-b]pyrazin-2-yl]-ureido}-pyrrolidine-1-carboxylic acid methyl ester was prepared in the same manner from 1-(R)-pyrrolidin-3-yl-3-[5-(2-trimethylsilanyl-ethoxymethyl)-5H-pyrrolo[2,3-b]pyrazin-2-yl]-urea dihydrochloride.

Example 39

Step 3. Sulfonylation

Piperidin-4-yl-3-[5-(2-trimethylsilanyl-ethoxymethyl)-5H-pyrrolo[2,3-b]pyrazin-2-yl]-urea dihydrochloride (0.073 g, 0.158 mmol) was suspended in DCM (1 mL) and N,N-diisopropylethylamine (0.1 mL, 0.55 mmol) was added. Methanesulfonyl chloride (0.015 mL, 0.19 mmol) was added and the resulting solution stirred at RT overnight. The solvent was evaporated. The remaining semi-solid was purified by $SiO_2$ chromatography (12 g $SiO_2$, DCM/MeOH 0-4% MeOH). Obtained 0.065 g of 1-(1-methanesulfonyl-piperidin-4-yl)-3-[5-(2-trimethylsilanyl-ethoxymethyl)-5H-pyrrolo[2,3-b]pyrazin-2-yl]-urea as an off-white solid (88% yield).

1-[(1-Methane sulfonyl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and methanesulfonyl chloride.

1-[(1-Ethane sulfonyl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and ethanesulfonyl chloride.

1-[(1-Propanesulfonyl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and ethanesulfonyl chloride.

1-[(2-Propanesulfonyl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and ethanesulfonyl chloride.

1-(1-Cyclopropylmethanesulfonyl-piperidin-3-yl)-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and cyclopropyl-methanesulfonyl chloride.

1-(1-Cyclopropylsulfonyl-piperidin-3-yl)-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and cyclopropylsulfonyl chloride.

1-((R)-1-Methane sulfonyl-piperidin-3-yl)-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and methanesulfonyl chloride.

1-[(R)-1-(Propane-1-sulfonyl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and n-propylsulfonyl chloride.

1-[1-(2-M ethyl-propane-1-sulfonyl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and 2-methyl-propane-1-sulfonyl chloride.

1-[(R)-1-(2-Methyl-propane-1-sulfonyl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and 2-methyl-propane-1-sulfonyl chloride.

1-(1-Trifluoromethanesulfonyl-piperidin-3-yl)-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and trifluoromethane sulfonyl chloride.

1-[1-(2,2,2-Trifluoro-ethanesulfonyl)-piperidin-3-yl]-3-[5-(2-trimethylsilanyl-ethoxymethyl)-5H-pyrrolo[2,3-b]pyrazin-2-yl]-urea was prepared in the same manner from 1-piperidin-3-yl-3-[5-(2-trimethylsilanyl-ethoxymethyl)-5H-pyrrolo[2,3-b]pyrazin-2-yl]-urea dihydrochloride and 2,2,2-trifluoro-ethanesulfonyl chloride.

1-[1-(Butane-2-sulfonyl)-piperidin-3-yl]-3-[5-(2-trimethylsilanyl-ethoxymethyl)-5H-pyrrolo[2,3-b]pyrazin-2-yl]-urea prepared the same way from 1-piperidin-3-yl-3-[5-(2-trimethylsilanyl-ethoxymethyl)-5H-pyrrolo[2,3-b]pyrazin-2-yl]-urea dihydrochloride and butane-2-sulfonyl chloride.

1-((S)-1-Methanesulfonyl-piperidin-3-yl)-3-[5-(2-trimethylsilanyl-ethoxymethyl)-5H-pyrrolo[2,3-b]pyrazin-2-yl]-urea prepared the same way from (S)-1-piperidin-3-yl)-3-[5-(2-trimethylsilanyl-ethoxymethyl)-5H-pyrrolo[2,3-b]pyrazin-2-yl]-urea dihydrochloride and methanesulfonyl chloride.

1-[(S)-1-(Propane-1-sulfonyl)-piperidin-3-yl]-3-[5-(2-trimethylsilanyl-ethoxymethyl)-5H-pyrrolo[2,3-b]pyrazin-2-yl]-urea prepared the same way from (S)-1-piperidin-3-yl-3-[5-(2-trimethylsilanyl-ethoxymethyl)-5H-pyrrolo[2,3-b]pyrazin-2-yl]-urea dihydrochloride and propane-1-sulfonyl chloride.

1-[(S)-1-(2-M ethyl-propane-1-sulfonyl)-piperidin-3-yl]-3-[5-(2-trimethylsilanyl-ethoxymethyl)-5H-pyrrolo[2,3-b]pyrazin-2-yl]-urea prepared the same way from (S)-1-piperidin-3-yl-3-[5-(2-trimethylsilanyl-ethoxymethyl)-5H-pyrrolo[2,3-b]pyrazin-2-yl]-urea dihydrochloride and 2-methyl-propane-1-sulfonyl chloride.

1-[(S)-1-(3-Methyl-oxetan-3-ylmethanesulfonyl)-piperidin-3-yl]-3-[5-(2-trimethylsilanyl-ethoxymethyl)-5H-pyrrolo[2,3-b]pyrazin-2-yl]-urea prepared the same way from (S)-1-piperidin-3-yl-3-[5-(2-trimethylsilanyl-ethoxymethyl)-5H-pyrrolo[2,3-b]pyrazin-2-yl]-urea dihydrochloride and (3-methyl-oxetan-3-yl)-methanesulfonyl chloride.

1-[(S)-1-(2-Methoxy-ethanesulfonyl)-piperidin-3-yl]-3-[5-(2-trimethylsilanyl-ethoxymethyl)-5H-pyrrolo[2,3-b]pyrazin-2-yl]-urea prepared the same way from (S)-1-piperidin-3-yl-3-[5-(2-trimethylsilanyl-ethoxymethyl)-5H-pyrrolo[2,3-b]pyrazin-2-yl]-urea dihydrochloride and 2-methoxy-ethanesulfonyl chloride.

1-[(S)-1-(1-Trifluoromethyl-cyclopropylmethanesulfonyl)-piperidin-3-yl]-3-[5-(2-trimethylsilanyl-ethoxymethyl)-5H-pyrrolo[2,3-b]pyrazin-2-yl]-urea prepared the same way from (S)-1-piperidin-3-yl-3-[5-(2-trimethylsilanyl-ethoxymethyl)-5H-pyrrolo[2,3-b]pyrazin-2-yl]-urea dihydrochloride and (1-trifluoromethyl-cyclopropyl)-methanesulfonyl chloride.

1-((S)-1-Methanesulfonyl-pyrrolidin-3-yl)-3-[5-(2-trimethylsilanyl-ethoxymethyl)-5H-pyrrolo[2,3-b]pyrazin-2-yl]-urea prepared the same way from 1-(S)-pyrrolidin-3-yl-3-[5-(2-trimethylsilanyl-ethoxymethyl)-5H-pyrrolo[2,3-b]pyrazin-2-yl]-urea dihydrochloride and methanesulfonyl chloride.

1-[(S)-1-(Propane-1-sulfonyl)-pyrrolidin-3-yl]-3-[5-(2-trimethylsilanyl-ethoxymethyl)-5H-pyrrolo[2,3-b]pyrazin-2-yl]-urea prepared the same way from (S)-1-pyrrolidin-3-yl]-3-[5-(2-trimethylsilanyl-ethoxymethyl)-5H-pyrrolo[2,3-b]pyrazin-2-yl]-urea dihydrochloride and propane-1-sulfonyl chloride.

1-[(S)-1-(2-Methyl-propane-1-sulfonyl)-pyrrolidin-3-yl]-3-[5-(2-trimethylsilanyl-ethoxymethyl)-5H-pyrrolo[2,3-b]pyrazin-2-yl]-urea prepared the same way from (S)-1-pyrrolidin-3-yl]-3-[5-(2-trimethylsilanyl-ethoxymethyl)-5H-pyrrolo[2,3-b]pyrazin-2-yl]-urea dihydrochloride and 2-methyl-propane-1-sulfonyl chloride.

1-[1-(Propane-1-sulfonyl)-azepan-3-yl]-3-[5-(2-trimethylsilanyl-ethoxymethyl)-5H-pyrrolo[2,3-b]pyrazin-2-yl]-urea prepared the same way from 1-azepan-3-yl-3-[5-(2-trimethylsilanyl-ethoxymethyl)-5H-pyrrolo[2,3-b]pyrazin-2-yl]-urea dihydrochloride and propane-1-sulfonyl chloride.

1-[1-(2-Methyl-propane-1-sulfonyl)-azepan-3-yl]-3-[5-(2-trimethylsilanyl-ethoxymethyl)-5H-pyrrolo[2,3-b]pyrazin-2-yl]-urea prepared the same way from 1-azepan-3-yl-3-[5-(2-trimethylsilanyl-ethoxymethyl)-5H-pyrrolo[2,3-b]pyrazin-2-yl]-urea dihydrochloride and 2-methyl-propane-1-sulfonyl chloride.

1-[(3S,5S)-5-Methyl-1-(propane-1-sulfonyl)-piperidin-3-yl]-3-[5-(2-trimethylsilanyl-ethoxymethyl)-5H-pyrrolo[2,3-b]pyrazin-2-yl]-urea prepared the same way from 1-(3S,5S)-5-methyl-piperidin-3-yl-3-[5-(2-trimethylsilanyl-ethoxymethyl)-5H-pyrrolo[2,3-b]pyrazin-2-yl]-urea dihydrochloride and propane-1-sulfonyl chloride.

1-[(3S,5S)-5-Methyl-1-(2-methyl-propane-1-sulfonyl)-piperidin-3-yl]-3-[5-(2-trimethylsilanyl-ethoxymethyl)-5H-pyrrolo[2,3-b]pyrazin-2-yl]-urea prepared the same way from 1-(3S,5S)-5-methyl-piperidin-3-yl-3-[5-(2-trimethylsilanyl-ethoxymethyl)-5H-pyrrolo[2,3-b]pyrazin-2-yl]-urea dihydrochloride and 2-methyl-propane-1-sulfonyl chloride.

1-(1-Methanesulfonyl-azepan-4-yl)-3-[5-(2-trimethylsilanyl-ethoxymethyl)-5H-pyrrolo[2,3-b]pyrazin-2-yl]-urea prepared the same way from 1-azepan-4-yl-3-[5-(2-trimethylsilanyl-ethoxymethyl)-5H-pyrrolo[2,3-b]pyrazin-2-yl]-urea dihydrochloride and methanesulfonyl chloride.

1-[1-(3-M ethyl-butane-1-sulfonyl)-piperidin-3-yl]-3-[5-(2-trimethylsilanyl-ethoxymethyl)-5H-pyrrolo[2,3-b]pyrazin-2-yl]-urea prepared the same way from 1-piperidin-3-yl-3-[5-(2-trimethylsilanyl-ethoxymethyl)-5H-pyrrolo[2,3-b]pyrazin-2-yl]-urea dihydrochloride and 3-methyl-butane-1-sulfonyl chloride.

1-[1-(3,3,3-Trifluoro-propane-1-sulfonyl)-piperidin-3-yl]-3-[5-(2-trimethylsilanyl-ethoxymethyl)-5H-pyrrolo[2,3-b]pyrazin-2-yl]-urea prepared the same way from 1-piperidin-3-yl-3-[5-(2-trimethylsilanyl-ethoxymethyl)-5H-pyrrolo[2,3-b]pyrazin-2-yl]-urea dihydrochloride and 3,3,3-trifluoro-propane-1-sulfonyl.

1-[(S)-1-(2,2-Dimethyl-propane-1-sulfonyl)-piperidin-3-yl]-3-[5-(2-trimethylsilanyl-ethoxymethyl)-5H-pyrrolo[2,3-b]pyrazin-2-yl]-urea prepared the same way from (S)-1-piperidin-3-yl-3-[5-(2-trimethylsilanyl-ethoxymethyl)-5H-pyrrolo[2,3-b]pyrazin-2-yl]-urea dihydrochloride and 2,2-dimethyl-propane-1-sulfonyl.

Racemic cis 1-(1-methanesulfonyl-5-methyl-azepan-4-yl)-3-[5-(2-trimethylsilanyl-ethoxymethyl)-5H-pyrrolo[2,3-b]pyrazin-2-yl]-urea prepared the same way from racemic cis 1-(5-methyl-azepan-4-yl)-3-[5-(2-trimethylsilanyl-ethoxymethyl)-5H-pyrrolo[2,3-b]pyrazin-2-yl]-urea dihydrochloride and methanesulfonyl chloride.

Racemic 1-(1-methane sulfonyl-piperidin-2-ylmethyl)-3-[5-(2-trimethylsilanyl-ethoxymethyl)-5H-pyrrolo[2,3-b]pyrazin-2-yl]-urea prepared the same way from racemic 1-piperidin-2-ylmethyl-3-[5-(2-trimethylsilanyl-ethoxymethyl)-5H-pyrrolo[2,3-b]pyrazin-2-yl]-urea dihydrochloride and methanesulfonyl chloride.

Racemic 1-[2-(1-methanesulfonyl-piperidin-2-yl)-ethyl]-3-[5-(2-trimethylsilanyl-ethoxymethyl)-5H-pyrrolo[2,3-b]pyrazin-2-yl]-urea prepared the same way from racemic 1-(2-piperidin-2-yl-ethyl)-3-[5-(2-trimethylsilanyl-ethoxymethyl)-5H-pyrrolo[2,3-b]pyrazin-2-yl]-urea dihydrochloride and methanesulfonyl chloride.

Racemic 1-(1-methane sulfonyl-piperidin-3-ylmethyl)-3-[5-(2-trimethylsilanyl-ethoxymethyl)-5H-pyrrolo[2,3-b]pyrazin-2-yl]-urea prepared the same way from racemic 1-piperidin-3-ylmethyl-3-[5-(2-trimethylsilanyl-ethoxymethyl)-5H-pyrrolo[2,3-b]pyrazin-2-yl]-urea dihydrochloride and methanesulfonyl chloride.

1-(1-Methanesulfonyl-piperidin-4-ylmethyl)-3-[5-(2-trimethylsilanyl-ethoxymethyl)-5H-pyrrolo[2,3-b]pyrazin-2-yl]-urea prepared the same way from 1-piperidin-4-ylmethyl- 3-[5-(2-trimethylsilanyl-ethoxymethyl)-5H-pyrrolo[2,3-b]pyrazin-2-yl]-urea dihydrochloride and methanesulfonyl chloride.

1-[2-(1-Methanesulfonyl-piperidin-4-yl)-ethyl]-3-[5-(2-trimethylsilanyl-ethoxymethyl)-5H-pyrrolo[2,3-b]pyrazin-2-yl]-urea prepared the same way from 1-(2-piperidin-4-yl-ethyl)-3-[5-(2-trimethylsilanyl-ethoxymethyl)-5H-pyrrolo[2,3-b]pyrazin-2-yl]-urea dihydrochloride and methanesulfonyl chloride.

Racemic 1-(1-methanesulfonyl-pyrrolidin-3-ylmethyl)-3-[5-(2-trimethylsilanyl-ethoxymethyl)-5H-pyrrolo[2,3-b]pyrazin-2-yl]-urea prepared the same way from 1-pyrrolidin-3-ylmethyl-3-[5-(2-trimethylsilanyl-ethoxymethyl)-5H-pyrrolo[2,3-b]pyrazin-2-yl]-urea dihydrochloride and methanesulfonyl chloride.

Racemic 1-(1-methanesulfonyl-pyrrolidin-2-ylmethyl)-3-[5-(2-trimethylsilanyl-ethoxymethyl)-5H-pyrrolo[2,3-b]pyrazin-2-yl]-urea prepared the same way from 1-pyrrolidin-2-ylmethyl-3-[5-(2-trimethylsilanyl-ethoxymethyl)-5H-pyrrolo[2,3-b]pyrazin-2-yl]-urea dihydrochloride and methanesulfonyl chloride.

Racemic 1-(1-ethanesulfonyl-pyrrolidin-2-ylmethyl)-3-[5-(2-trimethylsilanyl-ethoxymethyl)-5H-pyrrolo[2,3-b]pyrazin-2-yl]-urea prepared the same way from 1-pyrrolidin-2-ylmethyl-3-[5-(2-trimethylsilanyl-ethoxymethyl)-5H-pyrrolo[2,3-b]pyrazin-2-yl]-urea dihydrochloride and ethanesulfonyl chloride.

Racemic 1-[1-(propane-2-sulfonyl)-pyrrolidin-2-ylmethyl]-3-[5-(2-trimethylsilanyl-ethoxymethyl)-5H-pyrrolo[2,3-b]pyrazin-2-yl]-urea prepared the same way from 1-pyrrolidin-2-ylmethyl-3-[5-(2-trimethylsilanyl-ethoxymethyl)-5H-pyrrolo[2,3-b]pyrazin-2-yl]-urea dihydrochloride and propane-2-sulfonyl chloride.

Racemic 1-[1-(propane-1-sulfonyl)-pyrrolidin-2-ylmethyl]-3-[5-(2-trimethylsilanyl-ethoxymethyl)-5H-pyrrolo[2,3-b]pyrazin-2-yl]-urea prepared the same way from 1-pyrrolidin-2-ylmethyl-3-[5-(2-trimethylsilanyl-ethoxymethyl)-5H-pyrrolo[2,3-b]pyrazin-2-yl]-urea dihydrochloride and propane-1-sulfonyl chloride.

Racemic 1-[1-(2-methyl-propane-1-sulfonyl)-pyrrolidin-2-ylmethyl]-3-[5-(2-trimethylsilanyl-ethoxymethyl)-5H-pyrrolo[2,3-b]pyrazin-2-yl]-urea was prepared in the same manner from 1-pyrrolidin-2-ylmethyl-3-[5-(2-trimethylsilanyl-ethoxymethyl)-5H-pyrrolo[2,3-b]pyrazin-2-yl]-urea dihydrochloride and 2-methyl-propane-1-sulfonyl chloride.

Racemic 1-[2-(1-methanesulfonyl-pyrrolidin-2-yl)-ethyl]-3-[5-(2-trimethylsilanyl-ethoxymethyl)-5H-pyrrolo[2,3-b]pyrazin-2-yl]-urea prepared the same way from 1-(2-pyrrolidin-2-yl-ethyl)-3-[5-(2-trimethylsilanyl-ethoxymethyl)-5H-pyrrolo[2,3-b]pyrazin-2-yl]-urea dihydrochloride and methanesulfonyl chloride.

1-[(R)-1-(Propane-2-sulfonyl)-pyrrolidin-3-yl]-3-[5-(2-trimethylsilanyl-ethoxymethyl)-5H-pyrrolo[2,3-b]pyrazin-2-yl]-urea was prepared in the same manner from 1-(R)-pyrrolidin-3-yl-3-[5-(2-trimethylsilanyl-ethoxymethyl)-5H-pyrrolo[2,3-b]pyrazin-2-yl]-urea dihydrochloride salt and propane-2-sulfonyl chloride.

1-[(R)-1-(Methanesulfonyl)-pyrrolidin-3-yl]-3-[5-(2-trimethylsilanyl-ethoxymethyl)-5H-pyrrolo[2,3-b]pyrazin-2-yl]-urea was prepared in the same manner from 1-(R)-pyrrolidin-3-yl-3-[5-(2-trimethylsilanyl-ethoxymethyl)-5H-pyrrolo[2,3-b]pyrazin-2-yl]-urea dihydrochloride salt and methanesulfonyl chloride.

1-[(R)-1-(Trifluoromethanesulfonyl)-pyrrolidin-3-yl]-3-[5-(2-trimethylsilanyl-ethoxymethyl)-5H-pyrrolo[2,3-b]pyrazin-2-yl]-urea was prepared in the same manner from 1-(R)-pyrrolidin-3-yl-3-[5-(2-trimethylsilanyl-ethoxymethyl)-5H-pyrrolo[2,3-b]pyrazin-2-yl]-urea dihydrochloride salt and trifluoromethanesulfonyl chloride.

1-[(R)-1-(3,3,3-trifluoro-propane-1-sulfonyl)-pyrrolidin-3-yl]-3-[5-(2-trimethylsilanyl-ethoxymethyl)-5H-pyrrolo[2,3-b]pyrazin-2-yl]-urea was prepared in the same manner from 1-(R)-pyrrolidin-3-yl-3-[5-(2-trimethylsilanyl-ethoxymethyl)-5H-pyrrolo[2,3-b]pyrazin-2-yl]-urea dihydrochloride salt and 3,3,3-trifluoro-propane-1-sulfonyl chloride.

1-[(R)-1-(Ethanesulfonyl)-pyrrolidin-3-yl]-3-[5-(2-trimethylsilanyl-ethoxymethyl)-5H-pyrrolo[2,3-b]pyrazin-2-yl]-urea was prepared in the same manner from 1-(R)-pyrrolidin-3-yl-3-[5-(2-trimethylsilanyl-ethoxymethyl)-5H-pyrrolo[2,3-b]pyrazin-2-yl]-urea dihydrochloride salt and ethanesulfonyl chloride.

1-[(R)-1-(Propane-1-sulfonyl)-pyrrolidin-3-yl]-3-[5-(2-trimethylsilanyl-ethoxymethyl)-5H-pyrrolo[2,3-b]pyrazin-2-yl]-urea was prepared in the same manner from 1-(R)-pyrrolidin-3-yl-3-[5-(2-trimethylsilanyl-ethoxymethyl)-5H-pyrrolo[2,3-b]pyrazin-2-yl]-urea dihydrochloride salt and propane-1-sulfonyl chloride.

1-[(R)-1-(2-Methyl-propane-1-sulfonyl)-pyrrolidin-3-yl]-3-[5-(2-trimethylsilanyl-ethoxymethyl)-5H-pyrrolo[2,3-b]pyrazin-2-yl]-urea was prepared in the same manner from 1-(R)-pyrrolidin-3-yl-3-[5-(2-trimethylsilanyl-ethoxymethyl)-5H-pyrrolo[2,3-b]pyrazin-2-yl]-urea dihydrochloride salt and 2-methyl-propane-1-sulfonyl chloride.

Racemic 1-(1-methanesulfonyl-azepan-3-yl)-3-[5-(2-trimethylsilanyl-ethoxymethyl)-5H-pyrrolo[2,3-b]pyrazin-2-yl]-urea was prepared in the same manner from racemic 1-azepan-3-yl-3-[5-(2-trimethylsilanyl-ethoxymethyl)-5H-pyrrolo[2,3-b]pyrazin-2-yl]-urea dihydrochloride and methanesulfonyl chloride.

Example 40

Step 3. Alkylation

DIPEA (0.13 mL, 0.732 mmol) was added at 0° C. to a suspension of 1-piperidin-2-ylmethyl-3-[5-(2-trimethylsilanyl-ethoxymethyl)-5H-pyrrolo[2,3-b]pyrazin-2-yl]-urea dihydrochloride (0.080 g, 0.198 mmol) in 10 mL of DCM. The resulting mixture was stirred at RT for 15 minutes before adding 2,2,2-trifluoroethyl triflate (0.056 mL, 0.396 mmol) was added. The reaction mixture was stirred at RT overnight before being evaporated. The residue was purified by $SiO_2$ flash chromatography to give 0.053 mg of racemic 1-[1-(2,2,2-trifluoro-ethyl)-piperidin-2-ylmethyl]-3-[5-(2-trimethylsilanyl-ethoxymethyl)-5H-pyrrolo[2,3-b]pyrazin-2-yl]-urea (55% yield).

Racemic 1-[1-(2,2,2-trifluoro-ethyl)-piperidin-3-ylmethyl]-3-[5-(2-trimethylsilanyl-ethoxymethyl)-5H-pyrrolo[2,3-b]pyrazin-2-yl]-urea prepared the same way from 1-piperidin-3-ylmethyl-3-[5-(2-trimethylsilanyl-ethoxymethyl)-5H-pyrrolo[2,3-b]pyrazin-2-yl]-urea dihydrochloride.

Racemic 1-{2-[1-(2,2,2-trifluoro-ethyl)-piperidin-3-yl]-ethyl}-3-[5-(2-trimethylsilanyl-ethoxymethyl)-5H-pyrrolo[2,3-b]pyrazin-2-yl]-urea prepared the same way from 1-(2-piperidin-3-yl-ethyl)-3-[5-(2-trimethylsilanyl-ethoxymethyl)-5H-pyrrolo[2,3-b]pyrazin-2-yl]-urea dihydrochloride.

Racemic 1-[1-(2,2,2-trifluoro-ethyl)-piperidin-3-ylmethyl]-3-[5-(2-trimethylsilanyl-ethoxymethyl)-5H-pyrrolo[2,3-b]pyrazin-2-yl]-urea prepared the same way from 1-piperidin-3-ylmethyl-3-[5-(2-trimethylsilanyl-ethoxymethyl)-5H-pyrrolo[2,3-b]pyrazin-2-yl]-urea dihydrochloride.

Racemic 1-{2-[1-(2,2,2-trifluoro-ethyl)-pyrrolidin-2-yl]-ethyl}-3-[5-(2-trimethylsilanyl-ethoxymethyl)-5H-pyrrolo[2,3-b]pyrazin-2-yl]-urea prepared the same way from 1-(2-pyrrolidin-2-yl-ethyl)-3-[5-(2-trimethylsilanyl-ethoxymethyl)-5H-pyrrolo[2,3-b]pyrazin-2-yl]-urea dihydrochloride.

Step 4

Example 41

Variation A

1-[(S)-1-(2,2-Dimethyl-propane-1-sulfonyl)-piperidin-3-yl]-3-[5-(2-trimethylsilanyl-ethoxymethyl)-5H-pyrrolo[2,3-b]pyrazin-2-yl]-urea (0.045 g, 0.086 mmol) was dissolved in 1M HCl in acetic acid (0.9 mL) and stirred at 60° C. After 1.5 hours the solvent was evaporated and the residue was dried under high vacuum. The remaining oil was taken up in MeOH:H$_2$O:EtN 8:1:1 (0.9 mL) and ethylenediamine (0.029 mL, 0.429 mmol) was added. The yellow solution stirred at RT overnight. The solvent was evaporated and the residue was purified by SiO$_2$ chromatography (8 g SiO$_2$, DCM: MeOH 0 to 5% MeOH) to give 0.025 g of 1-[(S)-1-(2,2-dimethyl-propane-1-sulfonyl)-piperidin-3-yl]-3-(5H-pyrrolo[2,3-b]pyrazin-2-yl)-urea as an off-white solid (74% yield).

Racemic 1-(5H-pyrrolo[2,3-b]pyrazin-2-yl)-3-[1-(3,3,3-trifluoro-propane-1-sulfonyl)-piperidin-3-yl]-urea was prepared in the same manner from 1-(5H-pyrrolo[2,3-b]pyrazin-2-yl)-3-[1-(3,3,3-trifluoro-propane-1-sulfonyl)-piperidin-3-yl]-urea.

1-[1-(3-Methyl-butane-1-sulfonyl)-piperidin-3-yl]-3-(5H-pyrrolo[2,3-b]pyrazin-2-yl)-urea was prepared in the same manner from 1-[1-(3-methyl-butane-1-sulfonyl)-piperidin-3-yl]-3-[5-(2-trimethylsilanyl-ethoxymethyl)-5H-pyrrolo[2,3-b]pyrazin-2-yl]-urea.

1-(1-Acetyl-azepan-4-yl)-3-(5H-pyrrolo[2,3-b]pyrazin-2-yl)-urea was prepared in the same manner from 1-(1-acetyl-azepan-4-yl)-3-[5-(2-trimethylsilanyl-ethoxymethyl)-5H-pyrrolo[2,3-b]pyrazin-2-yl]-urea.

1-(1-Methanesulfonyl-azepan-4-yl)-3-(5H-pyrrolo[2,3-b]pyrazin-2-yl)-urea was prepared in the same manner from 1-(1-methanesulfonyl-azepan-4-yl)-3-[5-(2-trimethylsilanyl-ethoxymethyl)-5H-pyrrolo[2,3-b]pyrazin-2-yl]-urea.

4-[3-(5H-Pyrrolo[2,3-b]pyrazin-2-yl)-ureido]-azepane-1-carboxylic acid methyl ester was prepared in the same manner from 4-[3-(5H-pyrrolo[2,3-b]pyrazin-2-yl)-ureido]-azepane-1-carboxylic acid methyl ester.

3-[3-(5H-Pyrrolo[2,3-b]pyrazin-2-yl)-ureido]-piperidine-1-carboxylic acid ethyl ester was prepared in the same manner from 3-{3-[5-(2-trimethylsilanyl-ethoxymethyl)-5H-pyrrolo[2,3-b]pyrazin-2-yl]-ureido}-piperidine-1-carboxylic acid ethyl ester.

(S)-3-[3-(5H-Pyrrolo[2,3-b]pyrazin-2-yl)-ureido]-pyrrolidine-1-carboxylic acid methyl ester was prepared in the same manner from 1-(S)-pyrrolidin-3-yl-3-[5-(2-trimethylsilanyl-ethoxymethyl)-5H-pyrrolo[2,3-b]pyrazin-2-yl]-urea.

1-((S)-1-Acetyl-pyrrolidin-3-yl)-3-(5H-pyrrolo[2,3-b]pyrazin-2-yl)-urea was prepared in the same manner from 1-((S)-1-acetyl-pyrrolidin-3-yl)-3-[5-(2-trimethylsilanyl-ethoxymethyl)-5H-pyrrolo[2,3-b]pyrazin-2-yl]-urea.

1-[(3S,5S)-5-M ethyl-1-(2-methyl-propane-1-sulfonyl)-piperidin-3-yl]-3-(5H-pyrrolo[2,3-b]pyrazin-2-yl)-urea was prepared in the same manner from 1-[(3S,5S)-5-methyl-1-(2-methyl-propane-1-sulfonyl)-piperidin-3-yl]-3-[5-(2-trimethylsilanyl-ethoxymethyl)-5H-pyrrolo[2,3-b]pyrazin-2-yl]-urea.

1-[(3S,5S)-5-Methyl-1-(propane-1-sulfonyl)-piperidin-3-yl]-3-(5H-pyrrolo[2,3-b]pyrazin-2-yl)-urea was prepared in the same manner from 1-[(3S,5S)-5-methyl-1-(propane-1-sulfonyl)-piperidin-3-yl]-3-[5-(2-trimethylsilanyl-ethoxymethyl)-5H-pyrrolo[2,3-b]pyrazin-2-yl]-urea.

1-[1-(2-Methyl-propane-1-sulfonyl)-azepan-3-yl]-3-(5H-pyrrolo[2,3-b]pyrazin-2-yl)-urea was prepared in the same manner from 1-[1-(2-methyl-propane-1-sulfonyl)-azepan-3-yl]-3-[5-(2-trimethylsilanyl-ethoxymethyl)-5H-pyrrolo[2,3-b]pyrazin-2-yl]-urea.

1-[1-(Propane-1-sulfonyl)-azepan-3-yl]-3-(5H-pyrrolo[2,3-b]pyrazin-2-yl)-urea was prepared in the same manner from 1-[1-(propane-1-sulfonyl)-azepan-3-yl]-3-[5-(2-trimethylsilanyl-ethoxymethyl)-5H-pyrrolo[2,3-b]pyrazin-2-yl]-urea.

1-[(S)-1-(2-Methyl-propane-1-sulfonyl)-pyrrolidin-3-yl]-3-(5H-pyrrolo[2,3-b]pyrazin-2-yl)-urea was prepared in the same manner from 1-[(S)-1-(2-methyl-propane-1-sulfonyl)-pyrrolidin-3-yl]-3-[5-(2-trimethylsilanyl-ethoxymethyl)-5H-pyrrolo[2,3-b]pyrazin-2-yl]-urea.

1-[(S)-1-(Propane-1-sulfonyl)-pyrrolidin-3-yl]-3-(5H-pyrrolo[2,3-b]pyrazin-2-yl)-urea was prepared in the same manner from 1-[(S)-1-(propane-1-sulfonyl)-pyrrolidin-3-yl]-3-[5-(2-trimethylsilanyl-ethoxymethyl)-5H-pyrrolo[2,3-b]pyrazin-2-yl]-urea.

1-((S)-1-Methanesulfonyl-pyrrolidin-3-yl)-3-(5H-pyrrolo[2,3-b]pyrazin-2-yl)-urea was prepared in the same manner from 1-((S)-1-methanesulfonyl-pyrrolidin-3-yl)-3-[5-(2-trimethylsilanyl-ethoxymethyl)-5H-pyrrolo[2,3-b]pyrazin-2-yl]-urea.

1-[(S)-1-(2-Methyl-propane-1-sulfonyl)-piperidin-3-yl]-3-(5H-pyrrolo[2,3-b]pyrazin-2-yl)-urea was prepared in the same manner from 1-[(S)-1-(2-methyl-propane-1-sulfonyl)-piperidin-3-yl]-3-[5-(2-trimethylsilanyl-ethoxymethyl)-5H-pyrrolo[2,3-b]pyrazin-2-yl]-urea.

1-[(S)-1-(Propane-1-sulfonyl)-piperidin-3-yl]-3-(5H-pyrrolo[2,3-b]pyrazin-2-yl)-urea was prepared in the same manner from 1-[(S)-1-(propane-1-sulfonyl)-piperidin-3-yl]-3-[5-(2-trimethylsilanyl-ethoxymethyl)-5H-pyrrolo[2,3-b]pyrazin-2-yl]-urea.

1-((S)-1-Methanesulfonyl-piperidin-3-yl)-3-(5H-pyrrolo[2,3-b]pyrazin-2-yl)-urea was prepared in the same manner from 1-((S)-1-methanesulfonyl-piperidin-3-yl)-3-[5-(2-trimethylsilanyl-ethoxymethyl)-5H-pyrrolo[2,3-b]pyrazin-2-yl]-urea.

4-[3-(5H-Pyrrolo[2,3-b]pyrazin-2-yl)-ureido]-piperidine-1-carboxylic acid methyl ester was prepared in the same manner from 4-[3-(5H-pyrrolo[2,3-b]pyrazin-2-yl)-ureido]-piperidine-1-carboxylic acid methyl ester.

1-[1-(Butane-2-sulfonyl)-piperidin-3-yl]-3-(5H-pyrrolo[2,3-b]pyrazin-2-yl)-urea was prepared in the same manner from 1-[1-(butane-2-sulfonyl)-piperidin-3-yl]-3-[5-(2-trimethylsilanyl-ethoxymethyl)-5H-pyrrolo[2,3-b]pyrazin-2-yl]-urea.

1-[1-(Ethanesulfonyl)-piperidin-3-yl]-3-(5H-pyrrolo[2,3-b]pyrazin-2-yl)-urea was prepared in the same manner from 1-[(1-ethanesulfonyl)-piperidin-3-yl]-3-[5-(2-trimethylsilanyl-ethoxymethyl)-5H-pyrrolo[2,3-b]pyrazin-2-yl]-urea.

1-[(1-Propane-1-sulfonyl)-piperidin-3-yl]-3-(5H-pyrrolo[2,3-b]pyrazin-2-yl)-urea was prepared in the same manner from 1-[1-(propane-1-sulfonyl)-piperidin-3-yl]-3-[5-(2-trimethylsilanyl-ethoxymethyl)-5H-pyrrolo[2,3-b]pyrazin-2-yl]-urea.

1-[1-(Propane-2-sulfonyl)-piperidin-3-yl]-3-(5H-pyrrolo[2,3-b]pyrazin-2-yl)-urea was prepared in the same manner from 1-[1-(propane-2-sulfonyl)-piperidin-3-yl]-3-[5-(2-trimethylsilanyl-ethoxymethyl)-5H-pyrrolo[2,3-b]pyrazin-2-yl]-urea.

1-(1-Acetyl-piperidin-4-yl)-3-(5H-pyrrolo[2,3-b]pyrazin-2-yl)-urea was prepared in the same manner from 1-(1-acetyl-piperidin-4-yl)-3-[5-(2-trimethylsilanyl-ethoxymethyl)-5H-pyrrolo[2,3-b]pyrazin-2-yl]-urea.

1-(1-Acetyl-piperidin-3-yl)-3-(5H-pyrrolo[2,3-b]pyrazin-2-yl)-urea was prepared in the same manner from 1-(1-acetyl-piperidin-3-yl)-3-[5-(2-trimethylsilanyl-ethoxymethyl)-5H-pyrrolo[2,3-b]pyrazin-2-yl]-urea.

1-(1-Methanesulfonyl-piperidin-4-yl)-3-(5H-pyrrolo[2,3-b]pyrazin-2-yl)-urea was prepared in the same manner from 1-(1-methanesulfonyl-piperidin-4-yl)-3-[5-(2-trimethylsilanyl-ethoxymethyl)-5H-pyrrolo[2,3-b]pyrazin-2-yl]-urea.

1-[1-(2-M ethyl-propane-1-sulfonyl)-piperidin-3-yl]-3-(5H-pyrrolo[2,3-b]pyrazin-2-yl)-urea was prepared in the same manner from 1-[1-(2-methyl-propane-1-sulfonyl)-piperidin-3-yl]-3-[5-(2-trimethylsilanyl-ethoxymethyl)-5H-pyrrolo[2,3-b]pyrazin-2-yl]-urea.

1-((3S,5S)-1-Acetyl-5-methyl-piperidin-3-yl)-3-(5H-pyrrolo[2,3-b]pyrazin-2-yl)-urea was prepared in the same manner from 1-((3S,5S)-1-acetyl-5-methyl-piperidin-3-yl)-3-[5-(2-trimethylsilanyl-ethoxymethyl)-5H-pyrrolo[2,3-b]pyrazin-2-yl]-urea.

Racemic trans 1-(3-M ethoxymethyl-cyclohexyl)-3-(5H-pyrrolo[2,3-b]pyrazin-2-yl)-urea was prepared in the same manner from racemic trans 1-(3-Methoxymethyl-cyclohexyl)-3-[5-(2-trimethylsilanyl-ethoxymethyl)-(5H-pyrrolo[2,3-b]pyrazin-2-yl]-urea.

1-((1S,2R)-2-Methyl-cyclohexyl)-3-(5H-pyrrolo[2,3-b]pyrazin-2-yl)-urea was prepared in the same manner from 1-((1S,2R)-2-methyl-cyclohexyl)-3-[5-(2-trimethylsilanyl-ethoxymethyl)-5H-pyrrolo[2,3-b]pyrazin-2-yl]-urea. The minor trans isomer 1-((1R,2R)-2-methyl-cyclohexyl)-3-(5H-pyrrolo[2,3-b]pyrazin-2-yl)-urea was separated from the major cis isomer by preparative Supercritical Fluid Chromatography performed on a Berger MultiGram II (TharSFC) Chiralcel OD-H preparative SFC column (30 mm×250 mm ID, 5 micron packing), 70% $CO_2$/30% MeOH1 at a flow rate of 70 mL/min. The material was dissolved in 100% MeOH to an estimated concentration of 20 mg/mL.

1-(5H-Pyrrolo[2,3-b]pyrazin-2-yl)-3-spiro[2.5]oct-5-yl-urea was prepared in the same manner from 1-spiro[2.5]oct-5-yl-3-[5-(2-trimethylsilanyl-ethoxymethyl)-5H-pyrrolo[2,3-b]pyrazin-2-yl]-urea.

Trans 1-(3-Hydroxymethyl-cyclohexyl)-3-(5H-pyrrolo[2,3-b]pyrazin-2-yl)-urea was prepared in the same manner from trans acetic acid 3-{3-[5-(2-trimethylsilanyl-ethoxymethyl)-5H-pyrrolo[2,3-b]pyrazin-2-yl]-ureido}-cyclohexylmethyl ester. During the final step of step 4 the reaction mixture was heated to 45° C. overnight to completely hydrolyze the acetate.

1-[(S)-1-(2-M ethoxy-ethanesulfonyl)-piperidin-3-yl]-3-(5H-pyrrolo[2,3-b]pyrazin-2-yl)-urea was prepared in the same manner from 1-[(S)-1-(2-methoxy-ethane sulfonyl)-piperidin-3-yl]-3-[5-(2-trimethylsilanyl-ethoxymethyl)-5H-pyrrolo[2,3-b]pyrazin-2-yl]-urea.

1-((S)-1-Acetyl-piperidin-3-yl)-3-(5H-pyrrolo[2,3-b]pyrazin-2-yl)-urea was prepared in the same manner from 1-((S)-1-acetyl-piperidin-3-yl)-3-[5-(2-trimethylsilanyl-ethoxymethyl)-5H-pyrrolo[2,3-b]pyrazin-2-yl]-urea.

1-((R)-1-Acetyl-piperidin-3-yl)-3-(5H-pyrrolo[2,3-b]pyrazin-2-yl)-urea was prepared in the same manner from 1-((R)-1-acetyl-piperidin-3-yl)-3-[5-(2-trimethylsilanyl-ethoxymethyl)-5H-pyrrolo[2,3-b]pyrazin-2-yl]-urea.

1-(1-Propionyl-piperidin-3-yl)-3-(5H-pyrrolo[2,3-b]pyrazin-2-yl)-urea was prepared in the same manner from 1-(1-propionyl-piperidin-3-yl)-3-[5-(2-trimethylsilanyl-ethoxymethyl)-5H-pyrrolo[2,3-b]pyrazin-2-yl]-urea.

1-(1-Isobutyryl-piperidin-3-yl)-3-(5H-pyrrolo[2,3-b]pyrazin-2-yl)-urea was prepared in the same manner from 1-(1-isobutyryl-piperidin-3-yl)-3-[5-(2-trimethylsilanyl-ethoxymethyl)-5H-pyrrolo[2,3-b]pyrazin-2-yl]-urea.

1-[1-(3-Methyl-butyryl)-piperidin-3-yl]-3-(5H-pyrrolo[2,3-b]pyrazin-2-yl)-urea was prepared in the same manner from 1-[1-(3-methyl-butyryl)-piperidin-3-yl]-3-[5-(2-trimethylsilanyl-ethoxymethyl)-5H-pyrrolo[2,3-b]pyrazin-2-yl]-urea.

1-(1-Cyclopropane carbonyl-piperidin-3-yl)-3-(5H-pyrrolo[2,3-b]pyrazin-2-yl)-urea was prepared in the same manner from 1-(1-cyclopropanecarbonyl-piperidin-3-yl)-3-[5-(2-trimethylsilanyl-ethoxymethyl)-5H-pyrrolo[2,3-b]pyrazin-2-yl]-urea.

1-(5H-Pyrrolo[2,3-b]pyrazin-2-yl)-3-(1-trifluoromethanesulfonyl-piperidin-3-yl)-urea was prepared in the same manner from 1-(1-trifluoromethanesulfonyl-piperidin-3-yl)-3-[5-(2-trimethylsilanyl-ethoxymethyl)-5H-pyrrolo[2,3-b]pyrazin-2-yl]-urea.

1-(5H-Pyrrolo[2,3-b]pyrazin-2-yl)-3-[1-(2,2,2-trifluoro-ethanesulfonyl)-piperidin-3-yl]-urea was prepared in the same manner from 1-[1-(2,2,2-trifluoro-ethanesulfonyl)-piperidin-3-yl]-3-[5-(2-trimethylsilanyl-ethoxymethyl)-5H-pyrrolo[2,3-b]pyrazin-2-yl]-urea.

1-[1-(2-Cyclopropyl-acetyl)-piperidin-3-yl]-3-(5H-pyrrolo[2,3-b]pyrazin-2-yl)-urea was prepared in the same manner from 1-[1-(2-cyclopropyl-acetyl)-piperidin-3-yl]-3-[5-(2-trimethylsilanyl-ethoxymethyl)-5H-pyrrolo[2,3-b]pyrazin-2-yl]-urea.

1-((R)-1-Methanesulfonyl-piperidin-3-yl)-3-(5H-pyrrolo[2,3-b]pyrazin-2-yl)-urea was prepared in the same manner from 1-((R)-1-methanesulfonyl-piperidin-3-yl)-3-[5-(2-trimethylsilanyl-ethoxymethyl)-5H-pyrrolo[2,3-b]pyrazin-2-yl]-urea.

1-[(R)-1-(Propane-1-sulfonyl)-piperidin-3-yl]-3-(5H-pyrrolo[2,3-b]pyrazin-2-yl)-urea was prepared in the same manner from 1-[(R)-1-(propane-1-sulfonyl)-piperidin-3-yl]-3-[5-(2-trimethylsilanyl-ethoxymethyl)-5H-pyrrolo[2,3-b]pyrazin-2-yl]-urea.

1-[1-(2-M ethyl-propane-1-sulfonyl)-piperidin-3-yl]-3-(5H-pyrrolo[2,3-b]pyrazin-2-yl)-urea was prepared in the same manner from 1-[1-(2-methyl-propane-1-sulfonyl)-piperidin-3-yl]-3-[5-(2-trimethylsilanyl-ethoxymethyl)-5H-pyrrolo[2,3-b]pyrazin-2-yl]-urea.

1-((3R,5R)-1-Acetyl-5-methyl-piperidin-3-yl)-3-(5H-pyrrolo[2,3-b]pyrazin-2-yl)-urea was prepared in the same manner from 1-((3R,5R)-1-acetyl-5-methyl-piperidin-3-yl)-3-[5-(2-trimethylsilanyl-ethoxymethyl)-5H-pyrrolo[2,3-b]pyrazin-2-yl]-urea.

1-[1-(Methanesulfonyl)-piperidin-3-yl]-3-(5H-pyrrolo[2,3-b]pyrazin-2-yl)-urea was prepared in the same manner from 1-[1-methanesulfonyl-piperidin-3-yl]-3-[5-(2-trimethylsilanyl-ethoxymethyl)-5H-pyrrolo[2,3-b]pyrazin-2-yl]-urea. Ethylenediamine was omitted in the second step.

3-[3-(5H-Pyrrolo[2,3-b]pyrazin-2-yl)-ureido]-piperidine-1-carboxylic acid methyl ester was prepared in the same manner from 3-{3-[5-(2-trimethylsilanyl-ethoxymethyl)-5H-pyrrolo[2,3-b]pyrazin-2-yl]-ureido}-piperidine-1-carboxylic acid methyl ester Ethylenediamine was omitted in the second step.

1-(5H-Pyrrolo[2,3-b]pyrazin-2-yl)-3-[1-(3,3,3-trifluoro-propionyl)-piperidin-3-yl]-urea was prepared in the same manner from 1-[1-(3,3,3-trifluoro-propionyl)-piperidin-3-yl]-3-[5-(2-trimethylsilanyl-ethoxymethyl)-5H-pyrrolo[2,3-b]pyrazin-2-yl]-urea. Ethylenediamine was omitted in the second step.

1-(5H-Pyrrolo[2,3-b]pyrazin-2-yl)-3-[1-(2,2,2-trifluoro-ethyl)-piperidin-3-yl]-urea was prepared in the same manner from 1-[1-(2,2,2-trifluoro-ethyl)-piperidin-3-yl]-3-[5-(2-trimethylsilanyl-ethoxymethyl)-5H-pyrrolo[2,3-b]pyrazin-2-yl]-urea. Ethylenediamine was omitted in the second step.

Racemic 1-(1-acetyl-piperidin-2-ylmethyl)-3-(5H-pyrrolo[2,3-b]pyrazin-2-yl)-urea was prepared in the same manner from 1-(1-acetyl-piperidin-2-ylmethyl)-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 2-{[3-(5H-pyrrolo[2,3-b]pyrazin-2-yl)-ureido]-methyl}-piperidine-1-carboxylic acid methyl ester was prepared in the same manner from 2-{3-[5-(2-trimethylsilanyl-ethoxymethyl)-5H-pyrrolo[2,3-b]pyrazin-2-yl]-ureidomethyl}-piperidine-1-carboxylic acid methyl ester. In this instance, the first step of the deprotection was run for 5 hours instead of 1.5 hours.

Racemic 1-(5H-pyrrolo[2,3-b]pyrazin-2-yl)-3-[1-(2,2,2-trifluoro-ethyl)-piperidin-2-ylmethyl]-urea was prepared in the same manner from 1-[1-(2,2,2-trifluoro-ethyl)-piperidin-2-ylmethyl]-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 1-[2-(1-acetyl-piperidin-2-yl)-ethyl]-3-(5H-pyrrolo[2,3-b]pyrazin-2-yl)-urea was prepared in the same manner from 1-[2-(1-acetyl-piperidin-2-yl)-ethyl]-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 1-[2-(1-methanesulfonyl-piperidin-2-yl)-ethyl]-3-(5H-pyrrolo[2,3-b]pyrazin-2-yl)-urea was prepared in the same manner from 1-[2-(1-methanesulfonyl-piperidin-2-yl)-ethyl]-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 2-{2-[3-(5H-pyrrolo[2,3-b]pyrazin-2-yl)-ureido]-ethyl}-piperidine-1-carboxylic acid methyl ester was prepared in the same manner from 2-(2-{3-[5-(2-trimethylsilanyl-ethoxymethyl)-5H-pyrrolo[2,3-b]pyrazin-2-yl]-ureido}-ethyl)-piperidine-1-carboxylic acid methyl ester. In this instance, the first step of the deprotection was run for 5 hours instead of 1.5 hours.

Racemic 1-(1-acetyl-piperidin-3-ylmethyl)-3-(5H-pyrrolo[2,3-b]pyrazin-2-yl)-urea was prepared in the same manner from 1-(1-acetyl-piperidin-3-ylmethyl)-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 1-(1-methanesulfonyl-piperidin-3-ylmethyl)-3-(5H-pyrrolo[2,3-b]pyrazin-2-yl)-urea was prepared in the same manner from 1-(1-methanesulfonyl-piperidin-3-ylmethyl)-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 3-{[3-(5H-pyrrolo[2,3-b]pyrazin-2-yl)-ureido]-methyl}-piperidine-1-carboxylic acid methyl ester was prepared in the same manner from 3-{3-[5-(2-trimethylsilanyl-ethoxymethyl)-5H-pyrrolo[2,3-b]pyrazin-2-yl]-ureidomethyl}-piperidine-1-carboxylic acid methyl ester. In this instance, the first step of the deprotection was run for 5 hours instead of 1.5 hours.

Racemic 1-(5H-pyrrolo[2,3-b]pyrazin-2-yl)-3-[1-(2,2,2-trifluoro-ethyl)-piperidin-3-ylmethyl]-urea was prepared in the same manner from racemic 1-[1-(2,2,2-trifluoro-ethyl)-piperidin-3-ylmethyl]-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 3-{[3-(5H-pyrrolo[2,3-b]pyrazin-2-yl)-ureido]-methyl}-pyrrolidine-1-carboxylic acid methyl ester was prepared in the same manner from racemic 3-{3-[5-(2-trimethylsilanyl-ethoxymethyl)-5H-pyrrolo[2,3-b]pyrazin-2-yl]-ureidomethyl}-pyrrolidine-1-carboxylic acid methyl ester. In this instance, the first step of the deprotection was run for 5 hours instead of 1.5 hours.

Racemic 2-{[3-(5H-pyrrolo[2,3-b]pyrazin-2-yl)-ureido]-methyl}-pyrrolidine-1-carboxylic acid methyl ester was prepared in the same manner from 2-{3-[5-(2-trimethylsilanyl-ethoxymethyl)-5H-pyrrolo[2,3-b]pyrazin-2-yl]-ureidomethyl}-pyrrolidine-1-carboxylic acid methyl ester. In this instance, the first step of the deprotection was run for 5 hours instead of 1.5 hours.

Racemic 1-(1-acetyl-pyrrolidin-2-ylmethyl)-3-(5H-pyrrolo[2,3-b]pyrazin-2-yl)-urea was prepared in the same manner from racemic 1-(1-acetyl-pyrrolidin-2-ylmethyl)-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 1-[2-(1-acetyl-pyrrolidin-2-yl)-ethyl]-3-(5H-pyrrolo[2,3-b]pyrazin-2-yl)-urea was prepared in the same manner from racemic 1-[2-(1-acetyl-pyrrolidin-2-yl)-ethyl]-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 1-[2-(1-methanesulfonyl-pyrrolidin-2-yl)-ethyl]-3-(5H-pyrrolo[2,3-b]pyrazin-2-yl)-urea was prepared in the same manner from racemic 1-[2-(1-methanesulfonyl-pyrrolidin-2-yl)-ethyl]-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 1-(5H-pyrrolo[2,3-b]pyrazin-2-yl)-3-{2-[1-(2,2,2-trifluoro-ethyl)-pyrrolidin-2-yl]-ethyl}-urea was prepared in the same manner from racemic 1-{2-[1-(2,2,2-trifluoro-ethyl)-pyrrolidin-2-yl]-ethyl}-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

Racemic 1-(1-ethanesulfonyl-pyrrolidin-2-ylmethyl)-3-(5H-pyrrolo[2,3-b]pyrazin-2-yl)-urea was prepared in the same manner from 1-(1-ethanesulfonyl-pyrrolidin-2-ylmethyl)-3-[5-(2-trimethylsilanyl-ethoxymethyl)-5H-pyrrolo[2,3-b]pyrazin-2-yl]-urea. In this instance, the first step of the deprotection was run for 5.5 hours instead of 1.5 hours.

Racemic 1-[1-(propane-2-sulfonyl)-pyrrolidin-2-ylmethyl]-3-(5H-pyrrolo[2,3-b]pyrazin-2-yl)-urea was prepared in the same manner from 1-[1-(propane-2-sulfonyl)-pyrrolidin-2-ylmethyl]-3-[5-(2-trimethylsilanyl-ethoxymethyl)-5H-pyrrolo[2,3-b]pyrazin-2-yl]-urea. In this instance, the first step of the deprotection was run for 5.5 hours instead of 1.5 hours.

Racemic 1-[1-(propane-1-sulfonyl)-pyrrolidin-2-ylmethyl]-3-(5H-pyrrolo[2,3-b]pyrazin-2-yl)-urea was prepared in the same manner from 1-[1-(propane-1-sulfonyl)-pyrrolidin-2-ylmethyl]-3-[5-(2-trimethylsilanyl-ethoxymethyl)-

5H-pyrrolo[2,3-b]pyrazin-2-yl]-urea. In this instance, the first step of the deprotection was run for 5.5 hours instead of 1.5 hours.

Racemic 1-[1-(2-methyl-propane-1-sulfonyl)-pyrrolidin-2-ylmethyl]-3-(5H-pyrrolo[2,3-b]pyrazin-2-yl)-urea was prepared in the same manner from 1-[1-(2-methyl-propane-1-sulfonyl)-pyrrolidin-2-ylmethyl]-3-[5-(2-trimethylsilanyl-ethoxymethyl)-5H-pyrrolo[2,3-b]pyrazin-2-yl]-urea. In this instance, the first step of the deprotection was run for 5.5 hours instead of 1.5 hours.

(1S,3S)-3-[3-(5H-Pyrrolo[2,3-b]pyrazin-2-yl)-ureido]-cyclopentanecarboxylic acid methylamide was prepared in the same manner from (1S,3S)-3-{3-[5-(2-trimethylsilanyl-ethoxymethyl)-5H-pyrrolo[2,3-b]pyrazin-2-yl]-ureido}-cyclopentanecarboxylic acid methylamide. In this instance, the first step of the deprotection was run for 3 hours instead of 1.5 hours.

(1S,3S)-3-[3-(5H-Pyrrolo[2,3-b]pyrazin-2-yl)-ureido]-cyclopentanecarboxylic acid ethylamide was prepared in the same manner from (1S,3S)-3-{3-[5-(2-Trimethylsilanyl-ethoxymethyl)-5H-pyrrolo[2,3-b]pyrazin-2-yl]-ureido}-cyclopentanecarboxylic acid ethylamide. In this instance, the first step of the deprotection was run for 3 hours instead of 1.5 hours.

Racemic trans 3-[3-(5H-pyrrolo[2,3-b]pyrazin-2-yl)-ureido]-cyclohexanecarboxylic acid dimethylamide was prepared in the same manner from racemic trans 3-{3-[5-(2-trimethylsilanyl-ethoxymethyl)-5H-pyrrolo[2,3-b]pyrazin-2-yl]-ureido}-cyclohexanecarboxylic acid dimethylamide. In this instance, the first step of the deprotection was run for 3 hours instead of 1.5 hours.

1-(2,2-Dimethyl-cyclopentyl)-3-(5H-pyrrolo[2,3-b]pyrazin-2-yl)-urea was prepared in the same manner from racemic 1-(2,2-dimethyl-cyclopentyl)-3-[5-(2-trimethylsilanyl-ethoxymethyl)-5H-pyrrolo[2,3-b]pyrazin-2-yl]-urea.

1-[(R)-1-(propane-2-sulfonyl)-pyrrolidin-3-yl]-3-(5H-pyrrolo[2,3-b]pyrazin-2-yl)-urea was prepared in the same manner from 1-[(R)-1-(propane-2-sulfonyl)-pyrrolidin-3-yl]-3-[5-(2-trimethylsilanyl-ethoxymethyl)-5H-pyrrolo[2,3-b)]pyrazin-2-yl]-urea.

1-((R)-1-M ethanesulfonyl-pyrrolidin-3-yl)-3-(5H-pyrrolo[2,3-b]pyrazin-2-yl)-urea was prepared in the same way from 1-[(R)-1-methanesulfonyl-pyrrolidin-3-yl]-3-[5-(2-trimethylsilanyl-ethoxymethyl)-5H-pyrrolo[2,3-b]pyrazin-2-yl]-urea.

1-(5H-Pyrrolo[2,3-b]pyrazin-2-yl)-3-((R)-1-trifluoromethanesulfonyl-pyrrolidin-3-yl)-urea was prepared in the same way from 1-((R)-1-trifluoromethanesulfonyl-pyrrolidin-3-yl)-3-[5-(2-trimethylsilanyl-ethoxymethyl)-5H-pyrrolo[2,3-b]pyrazin-2-yl]-urea.

1-((R)-1-Ethanesulfonyl-pyrrolidin-3-yl)-3-(5H-pyrrolo[2,3-b]pyrazin-2-yl)-urea was prepared in the same way from 1-((R)-1-ethanesulfonyl-pyrrolidin-3-yl)-3-[5-(2-trimethylsilanyl-ethoxymethyl)-5H-pyrrolo[2,3-b]pyrazin-2-yl]-urea.

1-[(R)-1-(Propane-1-sulfonyl)-pyrrolidin-3-yl]-3-(5H-pyrrolo[2,3-b]pyrazin-2-yl)-urea was prepared in the same way from 1-[(R)-1-(propane-1-sulfonyl)-pyrrolidin-3-yl]-3-[5-(2-trimethylsilanyl-ethoxymethyl)-5H-pyrrolo[2,3-b]pyrazin-2-yl]-urea.

1-[(R)-1-(2-Methyl-propane-1-sulfonyl)-pyrrolidin-3-yl]-3-(5H-pyrrolo[2,3-b]pyrazin-2-yl)-urea was prepared in the same way from 1-[(R)-1-(2-methyl-propane-1-sulfonyl)-pyrrolidin-3-yl]-3-[5-(2-trimethylsilanyl-ethoxymethyl)-5H-pyrrolo[2,3-b]pyrazin-2-yl]-urea.

1-(5H-Pyrrolo[2,3-b]pyrazin-2-yl)-3-[(R)-1-(3,3,3-trifluoro-propane-1-sulfonyl)-pyrrolidin-3-yl]-urea was prepared in the same way from 1-[(R)-1-(3,3,3-trifluoro-propane-1-sulfonyl)-pyrrolidin-3-yl]-3-[5-(2-trimethylsilanyl-ethoxymethyl)-5H-pyrrolo[2,3-b]pyrazin-2-yl]-urea.

(R)-3-[3-(5H-Pyrrolo[2,3-b]pyrazin-2-yl)-ureido]-pyrrolidine-1-carboxylic acid methyl ester was prepared in the same way from (R)-3-{3-[5-(2-trimethylsilanyl-ethoxymethyl)-5H-pyrrolo[2,3-b]pyrazin-2-yl]-ureido}-pyrrolidine-1-carboxylic acid methyl ester.

1-((R)-1-Acetyl-pyrrolidin-3-yl)-3-(5H-pyrrolo[2,3-b]pyrazin-2-yl)-urea was prepared in the same way from 1-((R)-1-acetyl-pyrrolidin-3-yl)-3-[5-(2-trimethylsilanyl-ethoxymethyl)-5H-pyrrolo[2,3-b]pyrazin-2-yl]-urea.

Racemic 1-(1-acetyl-azepan-3-yl)-3-(5H-pyrrolo[2,3-b]pyrazin-2-yl)-urea was prepared in the same way from racemic 1-(1-acetyl-azepan-3-yl)-3-[5-(2-trimethylsilanyl-ethoxymethyl)-5H-pyrrolo[2,3-b]pyrazin-2-yl]-urea.

Racemic 3-[3-(5H-pyrrolo[2,3-b]pyrazin-2-yl)-ureido]-azepane-1-carboxylic acid methyl ester was prepared in the same way from racemic 3-{3-[5-(2-trimethylsilanyl-ethoxymethyl)-5H-pyrrolo[2,3-b]pyrazin-2-yl]-ureido}-azepane-1-carboxylic acid methyl ester.

Racemic 1-(1-methanesulfonyl-azepan-3-yl)-3-(5H-pyrrolo[2,3-b]pyrazin-2-yl)-urea was prepared in the same way from racemic 1-(1-methanesulfonyl-azepan-3-yl)-3-[5-(2-trimethylsilanyl-ethoxymethyl)-5H-pyrrolo[2,3-b]pyrazin-2-yl]-urea.

Endo 1-bicyclo[2.2.1]hept-2-yl-3-(5H-pyrrolo[2,3-b]pyrazin-2-yl)-urea was prepared in the same way from endo 1-bicyclo[2.2.1]hept-2-yl-3-[5-(2-trimethylsilanyl-ethoxymethyl)-5H-pyrrolo[2,3-b]pyrazin-2-yl]-urea.

Exo 1-bicyclo[2.2.1]hept-2-yl-3-(5H-pyrrolo[2,3-b]pyrazin-2-yl)-urea was prepared in the same way from exo 1-bicyclo[2.2.1]hept-2-yl-3-[5-(2-trimethylsilanyl-ethoxymethyl)-5H-pyrrolo[2,3-b]pyrazin-2-yl]-urea.

1-(1-Methyl-cyclohexyl)-3-(5H-pyrrolo[2,3-b]pyrazin-2-yl)-urea was prepared in the same way from 1-(1-methyl-cyclohexyl)-3-[5-(2-trimethylsilanyl-ethoxymethyl)-5H-pyrrolo[2,3-b]pyrazin-2-yl]-urea.

Example 42

Variation B 1-(3-Methyl-tetrahydro-pyran-4-yl)-3-[5-(2-trimethylsilanyl-ethoxymethyl)-5H-pyrrolo[2,3-b]pyrazin-2-yl]-urea (0.065 g, 0.16 mmol) was suspended in MeOH and cooled down to 0° C. At that temperature the acetyl chloride (0.4 mL) was added. After the addition was complete the orange solution was allowed to warm up and stirred at 40° C. overnight. The solvent was evaporated and the remaining solid was dried under high vacuum. The orange solid was taken up in MeOH: $H_2O:Et_3N$ 8:1:1 and stirred at RT for 1 hour. The solvent was evaporated. The remaining off-white solid was absorbed onto $SiO_2$ and purified by $SiO_2$ chromatography (12 g $SiO_2$, DCM/magic (DCM:MeOH:$NH_4OH$ 60:10:1) 0-25% magic). Obtained 0.023 g of cis-1-(3-methyl-tetrahydro-pyran-4-yl)-3-(5H-pyrrolo[2,3-b]pyrazin-2-yl)-urea as an off-white solid, yield: 52%.

Racemic cis 1-((1R,2S)-2-methyl-cyclohexyl)-3-(5H-pyrrolo[2,3-b]pyrazin-2-yl)-urea was prepared in the same manner from 1-((1R,2S)-2-methyl-cyclohexyl)-3-[5-(2-trimethylsilanyl-ethoxymethyl)-5H-pyrrolo[2,3-b]pyrazin-2-yl]-urea. A preparative Supercritical Fluid Chromatography (SFC) was performed after the $SiO_2$ flash chromatography and the minor trans isomer 1-((1S,2S)-2-methyl-cyclohexyl)-3-(5H-pyrrolo[2,3-b]pyrazin-2-yl)-urea was also isolated. The purification was performed on a Berger MultiGram II (TharSFC) Chiralcel OD-H preparative SFC column (30 mm×250 mm ID, 5 micron packing), 70% CO$_2$/30% MeOH at a flow rate of 70 mL/min. The material was dissolved in 100% methanol to an estimated concentration of 20 mg/mL.

Racemic cis 1-(5H-pyrrolo[2,3-b]pyrazin-2-yl)-3-(2,5,5-trimethyl-cyclohexyl)-urea was prepared from racemic cis 1-(2,5,5-trimethyl-cyclohexyl)-3-[5-(2-trimethylsilanyl-ethoxymethyl)-5H-pyrrolo[2,3-b]pyrazin-2-yl]-urea.

Racemic 1-(5H-pyrrolo[2,3-b]pyrazin-2-yl)-3-{2-[1-(2,2,2-trifluoro-ethyl)-piperidin-3-yl]-ethyl}-urea was prepared in the same manner from 1-{2-[1-(2,2,2-trifluoro-ethyl)-piperidin-3-yl]-ethyl}-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

1-(1-Acetyl-piperidin-4-ylmethyl)-3-(5H-pyrrolo[2,3-b]pyrazin-2-yl)-urea was prepared in the same manner from 1-(1-acetyl-piperidin-4-ylmethyl)-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

1-(1-Methanesulfonyl-piperidin-4-ylmethyl)-3-(5H-pyrrolo[2,3-b]pyrazin-2-yl)-urea was prepared in the same manner from 1-(1-methanesulfonyl-piperidin-4-ylmethyl)-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

4-{[3-(5H-Pyrrolo[2,3-b]pyrazin-2-yl)-ureido]-methyl}-piperidine-1-carboxylic acid methyl ester was prepared in the same manner from 4-{3-[5-(2-trimethylsilanyl-ethoxymethyl)-5H-pyrrolo[2,3-b]pyrazin-2-yl]-ureidomethyl}-piperidine-1-carboxylic acid methyl ester. In this instance, the first step of the deprotection was run for 5 hours instead of 1.5 hours.

1-(5H-Pyrrolo[2,3-b]pyrazin-2-yl)-3-[1-(2,2,2-trifluoro-ethyl)-piperidin-4-ylmethyl]-urea was prepared in the same manner from 1-[1-(2,2,2-trifluoro-ethyl)-piperidin-4-ylmethyl]-3-[5-(2-trimethylsilanyl-ethoxymethyl)-5H-pyrrolo[2,3-b]pyrazin-2-yl]-urea. In this instance, the first step of the deprotection was run for 5 hours instead of 1.5 hours.

1-[2-(1-Acetyl-piperidin-4-yl)-ethyl]-3-(5H-pyrrolo[2,3-b]pyrazin-2-yl)-urea was prepared in the same manner from 1-[2-(1-acetyl-piperidin-4-yl)-ethyl]-3-[5-(2-trimethylsilanyl-ethoxymethyl)-5H-pyrrolo[2,3-b]pyrazin-2-yl]-urea.

1-[2-(1-M ethanesulfonyl-piperidin-4-yl)-ethyl]-3-(5H-pyrrolo[2,3-b]pyrazin-2-yl)-urea was prepared in the same manner from 1-[2-(1-methanesulfonyl-piperidin-4-yl)-ethyl]-3-[5-(2-trimethylsilanyl-ethoxymethyl)-5H-pyrrolo[2,3-b]pyrazin-2-yl]-urea.

4-{2-[3-(5H-Pyrrolo[2,3-b]pyrazin-2-yl)-ureido]-ethyl}-piperidine-1-carboxylic acid methyl ester was prepared in the same manner from 4-(2-{3-[5-(2-trimethylsilanyl-ethoxymethyl)-5H-pyrrolo[2,3-b]pyrazin-2-yl]-ureido}-ethyl)-piperidine-1-carboxylic acid methyl ester.

Example 43

Variation C 1-(3,3-Dimethyl-cyclohexyl)-3-[5-(2-trimethylsilanyl-ethoxymethyl)-5H-pyrrolo[2,3-b]pyrazin-2-yl]-urea (0.095 g, 0.227 mmol) was dissolved in 1M HCl in acetic acid (2 mL, 2.04 mmol) and the resulting yellow solution stirred at 50° C. for 1.5 hours. The reaction mixture was diluted with 2 mL of H$_2$O and basified with 3M NaOH. Light yellow precipitate forms. The solvent was evaporated. The yellow solid was taken up in MeOH:H$_2$O:Et$_3$N 8:1:1 and stirred at RT for 1 hour. The mixture was absorbed onto SiO$_2$ and purified by SiO$_2$ chromatography (12 g SiO$_2$, DCM/magic (DCM:MeOH:NH$_4$OH 60:10:1) 0-35% magic) to give 0.023 g of 1-(3,3-dimethyl-cyclohexyl)-3-(5H-pyrrolo[2,3-b]pyrazin-2-yl)-urea as an off-white solid (35% yield).

Racemic 1-(3-ethyl-cyclohexyl)-3-(5H-pyrrolo[2,3-b]pyrazin-2-yl)-urea was prepared in the same manner from 1-(3-methyl-cyclohexyl)-3-[5-(2-trimethylsilanyl-ethoxymethyl)-5H-pyrrolo[2,3-b]pyrazin-2-yl]-urea.

Racemic cis 1-(1-methanesulfonyl-4-methyl-azepan-5-yl)-3-(5H-pyrrolo[2,3-b]pyrazin-2-yl)-urea was prepared this way from 1-(1-methanesulfonyl-3-methyl-azepan-4-yl)-3-[5-(2-trimethylsilanyl-ethoxymethyl)-5H-pyrrolo[2,3-b]pyrazin-2-yl]-urea. In this instance, the reaction mixture was neutralized using a 1M aqueous NaOH instead of 3M and the crude reaction mixture was extracted with EtOAc.

Racemic cis 4-methyl-5-[3-(5H-pyrrolo[2,3-b]pyrazin-2-yl)-ureido]-azepane-1-carboxylic acid methyl ester was prepared this way from 3-methyl-4-{3-[5-(2-trimethylsilanyl-ethoxymethyl)-5H-pyrrolo[2,3-b]pyrazin-2-yl]-ureido}-azepane-1-carboxylic acid methyl ester. In this instance, the reaction mixture was neutralized using a 1M aqueous NaOH instead of 3M and the crude reaction mixture was extracted with EtOAc.

Racemic 1 1-[2-(1-acetyl-piperidin-3-yl)-ethyl]-3-(5H-pyrrolo[2,3-b]pyrazin-2-yl)-urea was prepared in the same manner from 1-[2-(1-acetyl-piperidin-3-yl)-ethyl]-3-[5-(2-trimethylsilanyl-ethoxymethyl)-5H-pyrrolo[2,3-b]pyrazin-2-yl]-urea. In this instance, the reaction mixture was stirred for 5 hours instead of 1.5 hours, it was neutralized using 2M aqueous NaOH instead of 3M, and was extracted with EtOAc.

Racemic 1-(1-methanesulfonyl-pyrrolidin-3-ylmethyl)-3-(5H-pyrrolo[2,3-b]pyrazin-2-yl)-urea was prepared in the same manner from racemic 1-(1-methanesulfonyl-pyrrolidin-3-ylmethyl)-3-[5-(2-trimethylsilanyl-ethoxymethyl)-5H-pyrrolo[2,3-b]pyrazin-2-yl]-urea. In this instance, the reaction mixture was stirred for 5 hours instead of 1.5 hours, it was neutralized using 2M aqueous NaOH instead of 3M, and was extracted with EtOAc.

Example 44

Variation D 1-(6-Methyl-spiro[2.5]oct-5-yl)-3-[5-(2-trimethylsilanyl-ethoxymethyl)-5H-pyrrolo[2,3-b]pyrazin-2-yl]-urea (0.1 g, 0.233 mmol) was dissolved in tetrabutylammonium fluoride 1M in THF (4.6 mL, 4.6 mmol) and ethylenediamine (0.31 mL, 4.6 mmol) was added. The resulting solution stirred at 70° C. for 5 hours. The solvent was mostly evaporated. The residue was partitioned between H$_2$O and EtOAc. The aqueous layer was extracted 2× with EtOAc; the organic layers were combined, dried over Na$_2$SO$_4$, filtered and evaporated. The remaining solid was purified by SiO$_2$ chromatography (23 g SiO$_2$, DCM:MeOH 0 to 5% MeOH). NMR of the off-white foam showed ~18% of the trans isomer. The major cis isomer was separated from the trans isomer by preparative TLC (DCM:MeOH 5% MeOH). Finally, 0.018 g of both cis enantiomers (51% yield), c is 1-(6-methyl-spiro[2.5]oct-5-yl)-3-(5H-pyrrolo[2,3-b]pyrazin-2-yl)-urea, were isolated by preparative Supercritical Fluid Chromatography performed on a Berger MultiGram II (TharSFC) Chiralcel OD-H preparative SFC column (30 mm×250 mm ID, 5 micron packing), 70% CO$_2$/30% MeOH at a flow rate of 70 mL/min. The material was dissolved in 100% methanol to an estimated concentration of 20 mg/mL.

1-(1-Cyclopropylmethanesulfonyl-piperidin-3-yl)-3-(5H-pyrrolo[2,3-b]pyrazin-2-yl)-urea was prepared in the same manner from 1-(1-cyclopropylmethanesulfonyl-piperidin-3-yl)-3-[5-(2-trimethylsilanyl-ethoxymethyl)-5H-pyrrolo[2,3-b]pyrazin-2-yl]-urea. In this instance, the second step of the purification was not performed.

1-(1-Cyclopropylesulfonyl-piperidin-3-yl)-3-(5H-pyrrolo[2,3-b]pyrazin-2-yl)-urea was prepared in the same manner from 1-(1-cyclopropylsulfonyl-piperidin-3-yl)-3-[5-(2-trimethylsilanyl-ethoxymethyl)-5H-pyrrolo[2,3-b]pyrazin-2-yl]-urea. In this instance, the second step of the purification was not performed.

1-[(R)-1-(2-Methyl-propane-1-sulfonyl)-piperidin-3-yl]-3-(5H-pyrrolo[2,3-b]pyrazin-2-yl)-urea was prepared in the same manner from 1-[(R)-1-(2-methyl-propane-1-sulfonyl)-piperidin-3-yl]-3-[5-(2-trimethylsilanyl-ethoxymethyl)-5H-pyrrolo[2,3-b]pyrazin-2-yl]-urea. In this instance, the second step of the purification was not performed.

1-[(S)-1-(3-M ethyl-oxetan-3-ylmethanesulfonyl)-piperidin-3-yl]-3-(5H-pyrrolo[2,3-b]pyrazin-2-yl)-urea was prepared in the same manner from 1-[(S)-1-(3-methyl-oxetan-3-ylmethanesulfonyl)-piperidin-3-yl]-3-[5-(2-trimethylsilanyl-ethoxymethyl)-5H-pyrrolo[2,3-b]pyrazin-2-yl]-urea. In this instance, the second step of the purification was not performed.

1-(5H-Pyrrolo[2,3-b]pyrazin-2-yl)-3-[(S)-1-(1-trifluoromethyl-cyclopropylmethanesulfonyl)-piperidin-3-yl]-urea was prepared in the same manner from 1-[(S)-1-(1-trifluoromethyl-cyclopropylmethanesulfonyl)-piperidin-3-yl]-3-[5-(2-trimethylsilanyl-ethoxymethyl)-5H-pyrrolo[2,3-b]pyrazin-2-yl]-urea. In this instance, the second step of the purification was not performed.

Racemic cis 1-(2-ethyl-cyclohexyl)-3-(5H-pyrrolo[2,3-b]pyrazin-2-yl)-urea was prepared this way from racemic cis 1-(2-ethyl-cyclohexyl)-3-[5-(2-trimethylsilanyl-ethoxymethyl)-5H-pyrrolo[2,3-b]pyrazin-2-yl]-urea. In this instance, the second step of the purification was not performed.

Racemic cis 1-(2-isopropyl-cyclohexyl)-3-(5H-pyrrolo[2,3-b]pyrazin-2-yl)-urea was prepared this way from racemic cis 1-(2-isopropyl-cyclohexyl)-3-[5-(2-trimethylsilanyl-ethoxymethyl)-5H-pyrrolo[2,3-b]pyrazin-2-yl]-urea. In this instance, the second step of the purification was not performed.

Racemic cis 1-(1-acetyl-3-methyl-piperidin-4-yl)-3-(5H-pyrrolo[2,3-b]pyrazin-2-yl)-urea was prepared this way from racemic cis 1-(1-acetyl-3-methyl-piperidin-4-yl)-3-[5-(2-trimethylsilanyl-ethoxymethyl)-5H-pyrrolo[2,3-b]pyrazin-2-yl]-urea. In this instance, the second step of the purification was not performed.

Racemic cis 1-(1-methanesulfonyl-3-methyl-piperidin-4-yl)-3-(5H-pyrrolo[2,3-b]pyrazin-2-yl)-urea was prepared this way from racemic cis 1-(1-methanesulfonyl-3-methyl-piperidin-4-yl)-3-[5-(2-trimethylsilanyl-ethoxymethyl)-5H-pyrrolo[2,3-b]pyrazin-2-yl]-urea. In this instance, the second step of the purification was not performed.

Racemic cis 3-methyl-4-[3-(5H-pyrrolo[2,3-b]pyrazin-2-yl)-ureido]-piperidine-1-carboxylic acid methyl ester was prepared this way from racemic cis 3-methyl-4-{3-[5-(2-trimethylsilanyl-ethoxymethyl)-5H-pyrrolo[2,3-b]pyrazin-2-yl]-ureido}-piperidine-1-carboxylic acid methyl ester. In this instance, the second step of the purification was not performed.

Racemic cis 1-(2-methyl-cycloheptyl)-3-(5H-pyrrolo[2,3-b]pyrazin-2-yl)-urea was prepared this way from racemic cis 1-(2-methyl-cycloheptyl)-3-[5-(2-trimethylsilanyl-ethoxymethyl)-5H-pyrrolo[2,3-b]pyrazin-2-yl]-urea. In this instance, the second step of the purification was not performed.

Racemic cis 1-(1-acetyl-4-methyl-azepan-5-yl)-3-(5H-pyrrolo[2,3-b]pyrazin-2-yl)-urea was prepared this way from 1-(1-acetyl-3-methyl-azepan-4-yl)-3-[5-(2-trimethylsilanyl-ethoxymethyl)-5H-pyrrolo[2,3-b]pyrazin-2-yl]-urea. In this instance, the second step of the purification was not performed.

Pyridin-2-ylmethyl-3-(5H-pyrrolo[2,3-b]pyrazin-2-yl)-urea was prepared this way from 1-pyridin-2-ylmethyl-3-[5-(2-trimethylsilanyl-ethoxymethyl)-5H-pyrrolo[2,3-b]pyrazin-2-yl]-urea. In this instance, the second step of the purification was not performed, but the final product was washed with hexanes/EtOAc 5% EtOAc.

Pyridin-3-ylmethyl-3-(5H-pyrrolo[2,3-b]pyrazin-2-yl)-urea was prepared this way from 1-pyridin-3-ylmethyl-3-[5-(2-trimethylsilanyl-ethoxymethyl)-5H-pyrrolo[2,3-b]pyrazin-2-yl]-urea. In this instance, the second step of the purification was not performed, but the final product was washed with hexanes/EtOAc 5% EtOAc.

1-(2-Pyridin-2-yl-ethyl)-3-(5H-pyrrolo[2,3-b]pyrazin-2-yl)-urea was prepared this way from 1-(2-pyridin-2-yl-ethyl)-3-[5-(2-trimethylsilanyl-ethoxymethyl)-5H-pyrrolo[2,3-b]pyrazin-2-yl]-urea. In this instance, the second step of the purification was not performed, but the final product was washed with hexanes/EtOAc 5% EtOAc.

1-(2-Pyridin-3-yl-ethyl)-3-(5H-pyrrolo[2,3-b]pyrazin-2-yl)-urea was prepared this way from 1-(2-pyridin-3-yl-ethyl)-3-[5-(2-trimethylsilanyl-ethoxymethyl)-5H-pyrrolo[2,3-b]pyrazin-2-yl]-urea. In this instance, the second step of the purification was not performed, but the final product was washed with hexanes/EtOAc 5% EtOAc.

Racemic 1-(1-methanesulfonyl-piperidin-2-ylmethyl)-3-(5H-pyrrolo[2,3-b]pyrazin-2-yl)-urea was prepared this way from racemic 1-(1-methanesulfonyl-piperidin-2-ylmethyl)-3-[5-(2-trimethylsilanyl-ethoxymethyl)-5H-pyrrolo[2,3-b]pyrazin-2-yl]-urea. In this instance, the second step of the purification was not performed.

Racemic 1-[2-(1-methanesulfonyl-piperidin-3-yl)-ethyl]-3-(5H-pyrrolo[2,3-b]pyrazin-2-yl)-urea was prepared in the same manner from 1-[2-(1-methanesulfonyl-piperidin-3-yl)-ethyl]-3-[5-(2-trimethylsilanyl-ethoxymethyl)-5H-pyrrolo[2,3-b]pyrazin-2-yl]-urea. In this instance, the reaction was stirred for 16 hours instead of 5 hours and the second step of the purification was not performed.

Racemic 3-{2-[3-(5H-pyrrolo[2,3-b]pyrazin-2-yl)-ureido]-ethyl}-piperidine-1-carboxylic acid methyl ester was prepared in the same manner from 3-(2-{3-[5-(2-trimethylsilanyl-ethoxymethyl)-5H-pyrrolo[2,3-b]pyrazin-2-yl]-ureido}-ethyl)-piperidine-1-carboxylic acid methyl ester. In this instance, the reaction was stirred for 16 hours instead of 5 hours and the second step of the purification was not performed.

Racemic 1-(1-methanesulfonyl-pyrrolidin-2-ylmethyl)-3-(5H-pyrrolo[2,3-b]pyrazin-2-yl)-urea was prepared in the same manner from 1-(1-methanesulfonyl-pyrrolidin-2-ylmethyl)-3-[5-(2-trimethylsilanyl-ethoxymethyl)-5H-pyrrolo[2,3-b]pyrazin-2-yl]-urea. In this instance, the reaction was stirred for 7.5 hours instead of 5 hours and the second step of the purification was not performed.

Example 45

Variation E

A mixture of 1-[1-(2-cyano-acetyl)-piperidin-3-yl]-3-[5-(2-trimethylsilanyl-ethoxymethyl)-5H-pyrrolo[2,3-b]pyrazin-2-yl]-urea (0.09 g, 0.197 mmol) and lithium tetrafluoroborate (0.184 g, 1.967 mmol) in 2 mL of a 9/1 mixture of acetonitrile and H₂O was stirred at 85° C. for 24 hours before being cooled to RT (almost no solvent left). The reaction mixture was diluted in 2 mL of a 9/1 mixture of acetonitrile and H₂O, ethylenediamine (0.066 mL, 0.983 mmol) was added and the resulting mixture was stirred at RT for 3 hours before being evaporated. The residue was partitioned between EtOAc and saturated aqueous NaHCO₃. The aqueous layer was back extracted twice with EtOAc. The combined organic layers were dried (Na₂SO₄), filtered, and evaporated. The fairly insoluble residue was adsorbed onto silica purified by SiO₂ flash chromatography (DCM/(DCM: MeOH:NH₄OH 60:10:1] 90% to 0% DCM) to give 0.008 g of (1-[1-(2-cyano-acetyl)-piperidin-3-yl]-3-(5H-pyrrolo[2,3-b] pyrazin-2-yl)-urea (14% yield).

Example 46

Synthesis of (1S,3S)-3-{3-[5-(2-Trimethylsilanyl-ethoxymethyl)-5H-pyrrolo[2,3-b]pyrazin-2-yl]-ureido}-cyclopentanecarboxylic acid methylamide

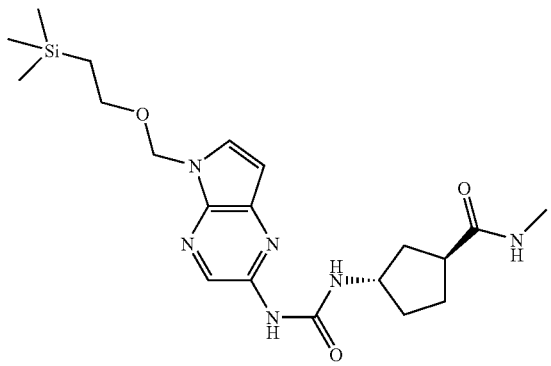

Step 1: A mixture of (1S,3S)-3-{3-[5-(2-trimethylsilanyl-ethoxymethyl)-5H-pyrrolo[2,3-b]pyrazin-2-yl]-ureido}-cyclopentanecarboxylic acid methyl (0.324 g, 0.75 mmol) and LiOH (0.036 g, 0.91 mmol) in 2 mL of THF, 2 mL of H₂O, and 0.5 mL of MeOH was stirred at RT for 24 hours. The reaction mixture was evaporated to give a waxy solid. The crude solid was triturated with H₂O and then suspended in ethyl acetate. The suspension was concentrated to dryness to give (1S,3S)-3-{3-[5-(2-trimethylsilanyl-ethoxymethyl)-5H-pyrrolo[2,3-b]pyrazin-2-yl]-ureido}-cyclopentanecarboxylic acid which was used as is in the following step.

Step 2: DIPEA (0.02 mL, 0.11 mmol) was added at RT to a mixture of (1S,3S)-3-{3-[5-(2-trimethylsilanyl-ethoxymethyl)-5H-pyrrolo[2,3-b]pyrazin-2-yl]-ureido}cyclopentanecarboxylic acid (0.075 g, 0.179 mmol), methylamine hydrochloride (0.024 g, 0.355 mmol), and EDCI (0.051 g, 0.266 mmol) in 1 mL of DCM. The resulting mixture was stirred at RT for 16 hours before being partitioned between H₂O and DCM. The aqueous layer was back extracted twice with DCM. The combined organic layers were dried (Na₂SO₄), filtered, and evaporated. The residue was purified by SiO₂ flash chromatography (DCM/MeOH 0 to 10% MeOH) to give 0.06 g of (1S,3S)-3-{3-[5-(2-trimethylsilanyl-ethoxymethyl)-5H-pyrrolo[2,3-b]pyrazin-2-yl]-ureido}-cyclopentanecarboxylic acid methylamide (76% yield).

(1S,3S)-3-{3-[5-(2-trimethylsilanyl-ethoxymethyl)-5H-pyrrolo[2,3-b]pyrazin-2-yl]-ureido}-cyclopentanecarboxylic acid ethylamide was prepared in the same manner using HATU instead of EDCI and DMF instead of DCM.

Example 47

Synthesis of trans 1-(3-Amino-cyclopentyl)-3-(5H-pyrrolo[2,3-b]pyrazin-2-yl)-urea trifluoroacetate

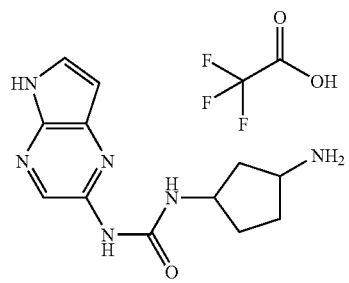

Step 1: In an oven dried flask was added 5-(2-trimethylsilanyl-ethoxymethyl)-5H pyrrolo[2,3-b]pyrazin-2-ylamine (0.118 g, 0.45 mmol), DIPEA (0.275 mL, 1.58 mmol) and 5 mL DCM and the flask cooled under N₂ in a dry ice acetone bath. A 20% solution of phosgene in toluene was added (0.284 mL, 0.54 mmol) and the purplish red solution was stirred for 20 minutes then warmed to −20° C. A solution of trans 2-(3-amino-cyclopentyl)-5,6-dichloro-isoindole-1,3-dione (0.143 g, est 0.5 mmol, mixture with monochloro derivative) in 8 mL DMF was added and stirred for 60 minutes, quench with MeOH and concentrated in vacuo. The residue was mixed with MeOH, filtered and the solid rinsed with MeOH and dried in vacuo to give trans 1-[3-(1,3-dioxo-1,3-dihydro-isoindol-2-yl)-cyclopentyl]-3-[5-(2-trimethylsilanyl-ethoxymethyl)-5H-pyrrolo[2,3-b]pyrazin-2-yl]-urea (0.196 g, 75% yield).

Step 2: Trans 1-[3-(1,3-Dioxo-1,3-dihydro-isoindol-2-yl)-cyclopentyl]-3-[5-(2-trimethylsilanyl-ethoxymethyl)-5H-pyrrolo[2,3-b]pyrazin-2-yl]-urea (0.288 g, 0.50 mmol) was dissolved with heating in DMF (10 mL) and placed in a 45° C. oil bath. The flask was evacuated and refilled with nitrogen three times. Hydrazine (0.16 mL, 5.1 mmol) was added via syringe. After 30 minutes AcOH (0.6 mL) was added and the mixture heated for 30 minutes more before being evaporated. MeOH was added, filtered and the filtrate was evaporated. H₂O was added, filtered and the filtrate was evaporated. The residue was purified by reverse phase column chromatography (20-80% MeOH in 0.1% aqueous AcOH) to give trans 1-(3-amino-cyclopentyl)-3-[5-(2-trimethylsilanyl-ethoxymethyl)-5H-pyrrolo[2,3-b]pyrazin-2-yl]-urea (0.134 g, 60% yield).

Step 3: In a flask trans 1-(3-amino-cyclopentyl)-3-[5-(2-trimethylsilanyl-ethoxymethyl)-5H-pyrrolo[2,3-b]pyrazin-2-yl]-urea (0.057 g, 0.127 mmol) in 1 M HCl in AcOH (1.3 mL) was heated in 65° C. oil bath for 2 hours, then 80° C. for 100 minutes, then concentrated in vacuo. To the residue was added MeOH (2 mL), H₂O (1 mL) and 2M aqueous dimethylamine (2 mL), stirred for 165 minutes and concentrated in vacuo. Purified on reverse phase column chromatography (MeOH/0.1 aqueous AcOH), concentrated in vacuo and purified again with (MeOH/0.1 aqueous TFA) to give trans 1-(3-Amino-cyclopentyl)-3-(5H-pyrrolo[2,3-b]pyrazin-2-yl)-urea trifluoroacetate (0.014 g, 29% yield).

JAK Assay Information
Determination of $IC_{50}$ of Janus Kinase (JAK) Inhibition:
  Enzymes and peptide substrate used are described below:
    JAK1: Recombinant human kinase domain (866-1154) from Invitrogen (Cat # PV4774)
    JAK3: Recombinant human kinase domain (810-1124) made in house by Roche Palo Alto
    JAK2: Recombinant human kinase domain (808-1132) from Millipore (Cat # 14-640)
    Substrate: N-terminally biotinylated 14-mer peptide derived from activation loop of JAK1 with sequence of the peptide substrate: Biotin-KAIETDKEYYTVKD
  Assay conditions used are described below:
    Assay Buffer: JAK Kinase Buffer: 50 mM Hepes [pH 7.2], 10 mM $MgCl_2$, 1 mM DTT, 1 mg/ml BSA. The assay is carried out in this buffer.
    Assay Format The kinase activity of all three JAK kinases is measured using a radioactive, end-point assay and with trace amounts of $^{33}$P-ATP. The assays are carried out in 96-well polypropylene plates.
Experimental Method:
  All concentrations are final in the reaction mixture and all incubations are carried at room temperature. Assay steps are described below:
  1) Compounds are serially diluted in 100% DMSO typically at a 10× starting concentration of 1 mM. Final concentration of DMSO in the reaction is 10%.
  2) Compounds are preincubated with enzyme (0.1 nM JAK3, 1 nM JAK2, 5 nM JAK1) for 10 minutes.
  3) Reactions are initiated by the addition of a cocktail of the two substrates (ATP and peptide premixed in the JAK Kinase Buffer). In the JAK1/JAK2/JAK3 assays, ATP and the peptide are used at concentrations of 1.5 uM and 50 uM, respectively. The duration of the assay for JAK2 and JAK3 is 20 minutes. JAK1 assay is carried out for 45 minutes. With all three enzymes, reactions are terminated by the addition of 0.5M EDTA to a final concentration of 100 mM.
  4) 25 ul of terminated reactions are transferred to 150 ul of a 7.5% (v/v) slurry of streptavidin-coated sepharose beads in $MgCl_2$- and $CaCl_2$-free 1× Phosphate Buffered Saline containing 50 mM of EDTA in 96-well, 1.2 um MultiScreen-BV filter plates.
  5) After a 30-minute incubation, the beads are washed under vacuum with the following buffers:
    a. 3 to 4 washes with 200 ul of 2M NaCl.
    b. 3 to 4 washes with 200 ul of 2M NaCl plus 1% (v/v) phosphoric acid.
    c. 1 wash with water.
  6) Washed plates are dried in a 60° C. oven for between 1 to 2 hours.
  7) 70 ul of Microscint 20 scintillation fluid is added to each well of filter plates and after at least 30 minutes of incubation, radioactive counts are measured in a Perkinelmer microplate scintillation counter.
Representative $IC_{50}$ results are in Table II below:

TABLE II

| Compound | Ic50 h-jak3-sf21-c: no additive |
|---|---|
| I-4 | 0.1422 |
| I-6 | 0.3264 |
| I-7 | 0.1155 |
| I-10 | 0.144 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:
1. A compound of Formula I

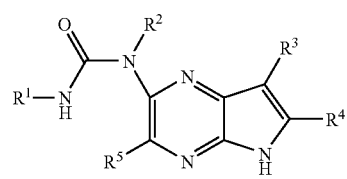

wherein:
$R^1$ is lower alkyl, cycloalkyl, cycloalkyl lower alkyl, phenyl, phenyl lower alkyl, heterocycloalkyl, heterocycloalkyl lower alkyl, heteroaryl, heteroaryl lower alkyl, or spirocycloalkyl, each optionally substituted with one or more $R^{1'}$;
  $R^{1'}$ is halogen, lower alkyl, hydroxy, lower hydroxyalkyl, lower alkoxy, lower haloalkyl, amino, —C(=O)N($R^{1a}$)$_2$, —C(=O)O($R^{1a}$), —C(=O)($R^{1a}$), —S(=O)$_2$($R^{1a}$), oxo, cyano, sulfonamido, cycloalkyl, or spirocycloalkyl;
    each $R^{1a}$ is H or $R^{1b}$;
      $R^{1b}$ is lower alkyl, lower haloalkyl, lower alkoxy, hydroxy lower alkyl, cyano lower alkyl, cycloalkyl, cycloalkyl lower alkyl, spirocycloalkyl, spirocycloalkyl lower alkyl, heterocycloalkyl, heterocycloalkyl lower alkyl, spiroheterocycloalkyl, or spiroheterocycloalkyl lower alkyl, each optionally substituted with one or more $R^{1b'}$;
        $R^{1b'}$ is halogen, hydroxy, lower alkyl, lower alkoxy, lower haloalkyl, or hydroxy lower alkyl;
$R^2$ is H or lower alkyl; and
$R^3$, $R^4$, and $R^5$ are independently selected from the group consisting of H, lower alkyl, halogen, hydroxy, lower hydroxyalkyl, lower alkoxy, and lower haloalkyl;
or a pharmaceutically acceptable salt thereof.
2. The compound of claim 1, wherein $R^1$ is cycloalkyl.
3. The compound of claim 1, wherein $R^2$ is H.
4. The compound of claim 3, wherein $R^1$ is cycloalkyl.
5. The compound of claim 3, wherein $R^3$ is H.
6. The compound of claim 5, wherein $R^1$ is cycloalkyl.
7. The compound of claim 5, wherein $R^4$ is H.
8. The compound of claim 7, wherein $R^1$ is cycloalkyl.
9. The compound of claim 7, wherein $R^5$ is H.
10. The compound of claim 9, wherein $R^1$ is cycloalkyl lower alkyl.
11. The compound of claim 9, wherein $R^1$ is phenyl lower alkyl.
12. The compound of claim 11, wherein $R^1$ is phenylethyl.

13. The compound of claim 9, wherein $R^1$ is cycloalkyl.
14. The compound of claim 13, wherein $R^1$ is cyclohexyl.
15. The compound of claim 14, wherein $R^{1'}$ is lower alkyl.
16. The compound of claim 15, wherein $R^{1'}$ is methyl.
17. The compound of claim 1, wherein $R^1$ is cycloalkyl, cycloalkyl lower alkyl, heterocycloalkyl, or heterocycloalkyl lower alkyl, each optionally substituted with one or more $R^{1'}$.
18. The compound of claim 17, wherein $R^2$ is H, $R^3$ is H, $R^4$ is H, and $R^5$ is H.
19. The compound of claim 18, wherein $R^1$ is pyrrolidine and $R^{1'}$ is —S(=O)$_2$(R$^{1a}$).
20. The compound of claim 18, wherein $R^1$ is heterocycloalkyl lower alkyl.
21. The compound of claim 20, wherein $R^1$ is pyrrolidinyl methylene and $R^{1'}$ is —S(=O)$_2$(R$^{1a}$).
22. The compound of claim 18, wherein $R^1$ is heterocycloalkyl.
23. The compound of claim 22, wherein $R^1$ is piperidine.
24. The compound of claim 23, wherein $R^{1'}$ is —S(=O)$_2$(R$^{1a}$).
25. The compound of claim 24, wherein $R^{1a}$ is lower alkyl.
26. A pharmaceutical composition comprising the compound of claim 1, admixed with at least one pharmaceutically acceptable carrier, excipient or diluent.
27. A method for inhibiting JAK3 activity comprising administering the compound of claim 1, wherein the compound exhibits an IC$_{50}$ of 50 micromolar or less in an in vitro biochemical assay of JAK3 activity.
28. The method of claim 27 wherein the compound exhibits an IC$_{50}$ of 100 nanomolar or less in an in vitro biochemical assay of JAK3 activity.
29. The method of claim 28 wherein the compound exhibits an IC$_{50}$ of 10 nanomolar or less in an in vitro biochemical assay of JAK3 activity.
30. A compound of the following formula:

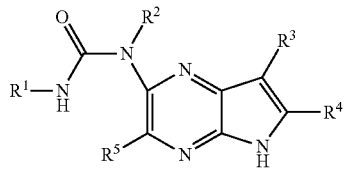

wherein:
 $R^1$ is cycloalkyl, cycloalkyl lower alkyl, phenyl lower alkyl, heterocycloalkyl, heterocycloalkyl lower alkyl, heteroaryl, or heteroaryl lower alkyl, optionally substituted with one or more $R^{1'}$;
  $R^{1'}$ is halogen, lower alkyl, hydroxy, lower hydroxyalkyl, lower alkoxy, lower haloalkyl, amino, amido, oxo, cyano, sulfonamido, or cycloalkyl; and
 $R^2$ is H or lower alkyl;
each of $R^3$, $R^4$, and $R^5$ are independently selected from the group consisting of H, lower alkyl, halogen, hydroxy, lower hydroxyalkyl, lower alkoxy, and lower haloalkyl; or a pharmaceutically acceptable salt thereof.
31. A compound selected from the group consisting of:
1-Cyclohexyl-3-(5H-pyrrolo[2,3-b]pyrazin-2-yl)-urea;
1-Phenyl-3-(5H-pyrrolo[2,3-b]pyrazin-2-yl)-urea;
1-Cyclopentyl-3-(5H-pyrrolo[2,3-b]pyrazin-2-yl)-urea;
1-Cycloheptyl-3-(5H-pyrrolo[2,3-b]pyrazin-2-yl)-urea;
1-Benzyl-3-(5H-pyrrolo[2,3-b]pyrazin-2-yl)-urea;
1-Cyclohexylmethyl-3-(5H-pyrrolo[2,3-b]pyrazin-2-yl)-urea;
1-((1S,2R)-2-Methyl-cyclohexyl)-3-(5H-pyrrolo[2,3-b]pyrazin-2-yl)-urea;
1-(2-Chloro-phenyl)-3-(5H-pyrrolo[2,3-b]pyrazin-2-yl)-urea;
1-((R)-1-Phenyl-ethyl)-3-(5H-pyrrolo[2,3-b]pyrazin-2-yl)-urea;
1-Phenethyl-3-(5H-pyrrolo[2,3-b]pyrazin-2-yl)-urea;
1-((S)-1-Phenyl-ethyl)-3-(5H-pyrrolo[2,3-b]pyrazin-2-yl)-urea;
1-(5H-Pyrrolo[2,3-b]pyrazin-2-yl)-3-o-tolyl-urea;
1-(5H-Pyrrolo[2,3-b]pyrazin-2-yl)-3-(2-trifluoromethyl-phenyl)-urea;
1-Ethyl-3-(5H-pyrrolo[2,3-b]pyrazin-2-yl)-urea;
1-tert-Butyl-3-(5H-pyrrolo[2,3-b]pyrazin-2-yl)-urea;
1-Isopropyl-3-(5H-pyrrolo[2,3-b]pyrazin-2-yl)-urea;
[3-(5H-Pyrrolo[2,3-b]pyrazin-2-yl)-ureido]-acetic acid ethyl ester;
N-Methyl-2-[3-(5H-pyrrolo[2,3-b]pyrazin-2-yl)-ureido]-acetamide;
(S)-3-Methyl-2-[3-(5H-pyrrolo[2,3-b]pyrazin-2-yl)-ureido]-butyric acid methyl ester;
(S)-3,N-Dimethyl-2-[3-(5H-pyrrolo[2,3-b]pyrazin-2-yl)-ureido]-butyramide;
1-((3S,4S)-3-Methyl-tetrahydro-pyran-4-yl)-3-(5H-pyrrolo[2,3-b]pyrazin-2-yl)-urea;
1-(5H-Pyrrolo[2,3-b]pyrazin-2-yl)-3-((1S,2R)-2,5,5-trimethyl-cyclohexyl)-urea;
1-(1-Acetyl-piperidin-3-yl)-3-(5H-pyrrolo[2,3-b]pyrazin-2-yl)-urea;
1-(3,3-Dimethyl-cyclohexyl)-3-(5H-pyrrolo[2,3-b]pyrazin-2-yl)-urea;
1-(3-Methyl-cyclohexyl)-3-(5H-pyrrolo[2,3-b]pyrazin-2-yl)-urea;
1-((1R,2S)-2-Methyl-cyclohexyl)-3-(5H-pyrrolo[2,3-b]pyrazin-2-yl)-urea;
1-(5H-Pyrrolo[2,3-b]pyrazin-2-yl)-3-spiro[2.5]oct-5-yl-urea;
3-Cyclohexyl-1-methyl-1-(5H-pyrrolo[2,3-b]pyrazin-2-yl)-urea;
1-[1-(2-Cyano-acetyl)-piperidin-3-yl]-3-(5H-pyrrolo[2,3-b]pyrazin-2-yl)-urea;
1-(2,2-Dimethyl-cyclopentyl)-3-(5H-pyrrolo[2,3-b]pyrazin-2-yl)-urea;
1-(5H-Pyrrolo[2,3-b]pyrazin-2-yl)-3-[1-(2,2,2-trifluoroethyl)-piperidin-3-yl]-urea;
1-(1-Methanesulfonyl-piperidin-3-yl)-3-(5H-pyrrolo[2,3-b]pyrazin-2-yl)-urea;
3-[3-(5H-Pyrrolo[2,3-b]pyrazin-2-yl)-ureido]-piperidine-1-carboxylic acid methyl ester;
1-((S)-1-Acetyl-piperidin-3-yl)-3-(5H-pyrrolo[2,3-b]pyrazin-2-yl)-urea;
1-((1R,3R)-3-Amino-cyclopentyl)-3-(5H-pyrrolo[2,3-b]pyrazin-2-yl)-urea;
1-(5H-Pyrrolo[2,3-b]pyrazin-2-yl)-3-[1-(3,3,3-trifluoropropionyl)-piperidin-3-yl]-urea;
1-((R)-1-Acetyl-piperidin-3-yl)-3-(5H-pyrrolo[2,3-b]pyrazin-2-yl)-urea;
3-[3-(5H-Pyrrolo[2,3-b]pyrazin-2-yl)-ureido]-piperidine-1-carboxylic acid ethyl Ester;
1-(1-Propionyl-piperidin-3-yl)-3-(5H-pyrrolo[2,3-b]pyrazin-2-yl)-urea;
1-(1-Isobutyryl-piperidin-3-yl)-3-(5H-pyrrolo[2,3-b]pyrazin-2-yl)-urea;
1-[1-(3-Methyl-butyryl)-piperidin-3-yl]-3-(5H-pyrrolo[2,3-b]pyrazin-2-yl)-urea;
1-Cyclohexyl-3-(6-methyl-5H-pyrrolo[2,3-b]pyrazin-2-yl)-urea;

1-Cyclohexyl-3-(7-methyl-5H-pyrrolo[2,3-b]pyrazin-2-yl)-urea;
1-(1-Ethanesulfonyl-piperidin-3-yl)-3-(5H-pyrrolo[2,3-b]pyrazin-2-yl)-urea;
1-[1-(Propane-2-sulfonyl)-piperidin-3-yl]-3-(5H-pyrrolo[2,3-b]pyrazin-2-yl)-urea;
1-((S)-1-Acetyl-pyrrolidin-3-yl)-3-(5H-pyrrolo[2,3-b]pyrazin-2-yl)-urea;
1-((S)-1-Methanesulfonyl-pyrrolidin-3-yl)-3-(5H-pyrrolo[2,3-b]pyrazin-2-yl)-urea;
(S)-3-[3-(5H-Pyrrolo[2,3-b]pyrazin-2-yl)-ureido]-pyrrolidine-1-carboxylic acid methyl ester;
1-((3S,5S)-1-Acetyl-5-methyl-piperidin-3-yl)-3-(5H-pyrrolo[2,3-b]pyrazin-2-yl)-urea;
1-(1-Cyclopropanesulfonyl-piperidin-3-yl)-3-(5H-pyrrolo[2,3-b]pyrazin-2-yl)-urea;
1-[1-(Propane-1-sulfonyl)-piperidin-3-yl]-3-(5H-pyrrolo[2,3-b]pyrazin-2-yl)-urea;
1-((5R,6S)-6-Methyl-spiro[2.5]oct-5-yl)-3-(5H-pyrrolo[2,3-b]pyrazin-2-yl)-urea;
1-((5S,6R)-6-Methyl-spiro[2.5]oct-5-yl)-3-(5H-pyrrolo[2,3-b]pyrazin-2-yl)-urea;
1-Pyridin-2-ylmethyl-3-(5H-pyrrolo[2,3-b]pyrazin-2-yl)-urea;
1-Pyridin-3-ylmethyl-3-(5H-pyrrolo[2,3-b]pyrazin-2-yl)-urea;
1-(2-Pyridin-2-yl-ethyl)-3-(5H-pyrrolo[2,3-b]pyrazin-2-yl)-urea;
1-(2-Pyridin-3-yl-ethyl)-3-(5H-pyrrolo[2,3-b]pyrazin-2-yl)-urea;
1-(2-Isopropyl-cyclohexyl)-3-(5H-pyrrolo[2,3-b]pyrazin-2-yl)-urea;
1-((1S,2R)-2-Methyl-cycloheptyl)-3-(5H-pyrrolo[2,3-b]pyrazin-2-yl)-urea;
1-((1R,2R)-2-Methyl-cyclohexyl)-3-(5H-pyrrolo[2,3-b]pyrazin-2-yl)-urea;
1-((1S,2S)-2-Methyl-cyclohexyl)-3-(5H-pyrrolo[2,3-b]pyrazin-2-yl)-urea;
(R)-3-[3-(5H-Pyrrolo[2,3-b]pyrazin-2-yl)-ureido]-pyrrolidine-1-carboxylic acid methyl ester;
1-((R)-1-Methanesulfonyl-pyrrolidin-3-yl)-3-(5H-pyrrolo[2,3-b]pyrazin-2-yl)-urea;
1-((R)-1-Acetyl-pyrrolidin-3-yl)-3-(5H-pyrrolo[2,3-b]pyrazin-2-yl)-urea;
1-(1-Cyclopropanecarbonyl-piperidin-3-yl)-3-(5H-pyrrolo[2,3-b]pyrazin-2-yl)-urea;
1-(5H-Pyrrolo[2,3-b]pyrazin-2-yl)-3-(1-trifluoromethanesulfonyl-piperidin-3-yl)-urea;
1-(5H-Pyrrolo[2,3-b]pyrazin-2-yl)-3-[1-(2,2,2-trifluoro-ethanesulfonyl)-piperidin-3-yl]-urea;
1-(2-Ethyl-cyclohexyl)-3-(5H-pyrrolo[2,3-b]pyrazin-2-yl)-urea;
1-(1-Acetyl-3-methyl-piperidin-4-yl)-3-(5H-pyrrolo[2,3-b]pyrazin-2-yl)-urea;
1-(1-Methanesulfonyl-3-methyl-piperidin-4-yl)-3-(5H-pyrrolo[2,3-b]pyrazin-2-yl)-urea;
3-Methyl-4-[3-(5H-pyrrolo[2,3-b]pyrazin-2-yl)-ureido]-piperidine-1-carboxylic acid methyl ester;
1-(1-Methanesulfonyl-pyrrolidin-2-ylmethyl)-3-(5H-pyrrolo[2,3-b]pyrazin-2-yl)-urea;
1-[1-(2-Cyclopropyl-acetyl)-piperidin-3-yl]-3-(5H-pyrrolo[2,3-b]pyrazin-2-yl)-urea;
1-(1-Methanesulfonyl-azepan-3-yl)-3-(5H-pyrrolo[2,3-b]pyrazin-2-yl)-urea;
3-[3-(5H-Pyrrolo[2,3-b]pyrazin-2-yl)-ureido]-azepane-1-carboxylic acid methyl ester;
1-(1-Acetyl-azepan-3-yl)-3-(5H-pyrrolo[2,3-b]pyrazin-2-yl)-urea;
1-[1-(2-Methyl-propane-1-sulfonyl)-piperidin-3-yl]-3-(5H-pyrrolo[2,3-b]pyrazin-2-yl)-urea;
1-(1-Methanesulfonyl-piperidin-4-yl)-3-(5H-pyrrolo[2,3-b]pyrazin-2-yl)-urea;
1-(1-Acetyl-piperidin-4-yl)-3-(5H-pyrrolo[2,3-b]pyrazin-2-yl)-urea;
1-[1-(Butane-2-sulfonyl)-piperidin-3-yl]-3-(5H-pyrrolo[2,3-b]pyrazin-2-yl)-urea;
1-((R)-1-Methanesulfonyl-piperidin-3-yl)-3-(5H-pyrrolo[2,3-b]pyrazin-2-yl)-urea;
1-[(R)-1-(Propane-1-sulfonyl)-piperidin-3-yl]-3-(5H-pyrrolo[2,3-b]pyrazin-2-yl)-urea;
4-[3-(5H-Pyrrolo[2,3-b]pyrazin-2-yl)-ureido]-piperidine-1-carboxylic acid methyl ester;
1-(1R,2R,4S)-Bicyclo [2.2.1]hept-2-yl-3-(5H-pyrrolo[2,3-b]pyrazin-2-yl)-urea;
1-(1R,2S,4S)-Bicyclo [2.2.1]hept-2-yl-3-(5H-pyrrolo[2,3-b]pyrazin-2-yl)-urea;
1-(1-Methyl-cyclohexyl)-3-(5H-pyrrolo[2,3-b]pyrazin-2-yl)-urea;
1-(1-Cyclopropylmethanesulfonyl-piperidin-3-yl)-3-(5H-pyrrolo[2,3-b]pyrazin-2-yl)-urea;
1-((1S,3S)-3-Hydroxymethyl-cyclohexyl)-3-(5H-pyrrolo[2,3-b]pyrazin-2-yl)-urea;
1-[(R)-1-(2-Methyl-propane-1-sulfonyl)-piperidin-3-yl]-3-(5H-pyrrolo[2,3-b]pyrazin-2-yl)-urea;
1-((S)-1-Methanesulfonyl-piperidin-3-yl)-3-(5H-pyrrolo[2,3-b]pyrazin-2-yl)-urea;
1-[(S)-1-(Propane-1-sulfonyl)-piperidin-3-yl]-3-(5H-pyrrolo[2,3-b]pyrazin-2-yl)-urea;
1-[(S)-1-(2-Methyl-propane-1-sulfonyl)-piperidin-3-yl]-3-(5H-pyrrolo[2,3-b]pyrazin-2-yl)-urea;
1-(7-Chloro-5H-pyrrolo[2,3-b]pyrazin-2-yl)-3-cyclohexyl-urea;
1-[(S)-1-(Propane-1-sulfonyl)-pyrrolidin-3-yl]-3-(5H-pyrrolo[2,3-b]pyrazin-2-yl)-urea;
1-[(S)-1-(2-Methyl-propane-1-sulfonyl)-pyrrolidin-3-yl]-3-(5H-pyrrolo[2,3-b]pyrazin-2-yl)-urea;
1-[1-(Propane-1-sulfonyl)-azepan-3-yl]-3-(5H-pyrrolo[2,3-b]pyrazin-2-yl)-urea;
1-[1-(2-Methyl-propane-1-sulfonyl)-azepan-3-yl]-3-(5H-pyrrolo[2,3-b]pyrazin-2-yl)-urea;
1-[(3S,5S)-5-Methyl-1-(propane-1-sulfonyl)-piperidin-3-yl]-3-(5H-pyrrolo[2,3-b]pyrazin-2-yl)-urea;
1-[(3S,5S)-5-Methyl-1-(2-methyl-propane-1-sulfonyl)-piperidin-3-yl]-3-(5H-pyrrolo[2,3-b]pyrazin-2-yl)-urea;
1-((R)-1-Ethanesulfonyl-pyrrolidin-3-yl)-3-(5H-pyrrolo[2,3-b]pyrazin-2-yl)-urea;
1-[(R)-1-(Propane-2-sulfonyl)-pyrrolidin-3-yl]-3-(5H-pyrrolo[2,3-b]pyrazin-2-yl)-urea;
1-[(R)-1-(Propane-1-sulfonyl)-pyrrolidin-3-yl]-3-(5H-pyrrolo[2,3-b]pyrazin-2-yl)-urea;
1-[(R)-1-(2-Methyl-propane-1-sulfonyl)-pyrrolidin-3-yl]-3-(5H-pyrrolo[2,3-b]pyrazin-2-yl)-urea;
1-(5H-Pyrrolo[2,3-b]pyrazin-2-yl)-3-((R)-1-trifluoromethanesulfonyl-pyrrolidin-3-yl)-urea;
1-(1-Methanesulfonyl-piperidin-2-ylmethyl)-3-(5H-pyrrolo[2,3-b]pyrazin-2-yl)-urea;
1-[2-(1-Methanesulfonyl-pyrrolidin-2-yl)-ethyl]-3-(5H-pyrrolo[2,3-b]pyrazin-2-yl)-urea;
2-{2-[3-(5H-Pyrrolo[2,3-b]pyrazin-2-yl)-ureido]-ethyl}-pyrrolidine-1-carboxylic acid methyl ester;
4-[3-(5H-Pyrrolo[2,3-b]pyrazin-2-yl)-ureido]-azepane-1-carboxylic acid methyl ester;

1-(1-Methanesulfonyl-azepan-4-yl)-3-(5H-pyrrolo[2,3-b]pyrazin-2-yl)-urea;
1-[2-(1-Methanesulfonyl-piperidin-3-yl)-ethyl]-3-(5H-pyrrolo[2,3-b]pyrazin-2-yl)-urea;
3-{2-[3-(5H-Pyrrolo[2,3-b]pyrazin-2-yl)-ureido]-ethyl}-piperidine-1-carboxylic acid methyl ester;
1-(1-Acetyl-azepan-4-yl)-3-(5H-pyrrolo[2,3-b]pyrazin-2-yl)-urea;
1-[1-(3-Methyl-butane-1-sulfonyl)-piperidin-3-yl]-3-(5H-pyrrolo[2,3-b]pyrazin-2-yl)-urea;
1-(5H-Pyrrolo[2,3-b]pyrazin-2-yl)-3-[1-(3,3,3-trifluoro-propane-1-sulfonyl)-piperidin-3-yl]-urea;
1-(5H-Pyrrolo[2,3-b]pyrazin-2-yl)-3-[(R)-1-(3,3,3-trifluoro-propane-1-sulfonyl)-pyrrolidin-3-yl]-urea;
1-((3R,5R)-1-Acetyl-5-methyl-piperidin-3-yl)-3-(5H-pyrrolo[2,3-b]pyrazin-2-yl)-urea;
1-[(S)-1-(2,2-Dimethyl-propane-1-sulfonyl)-piperidin-3-yl]-3-(5H-pyrrolo[2,3-b]pyrazin-2-yl)-urea;
1-[(S)-1-(2-Methoxy-ethanesulfonyl)-piperidin-3-yl]-3-(5H-pyrrolo[2,3-b]pyrazin-2-yl)-urea;
1-(1-Methanesulfonyl-5-methyl-azepan-4-yl)-3-(5H-pyrrolo[2,3-b]pyrazin-2-yl)-urea;
4-Methyl-5-[3-(5H-pyrrolo[2,3-b]pyrazin-2-yl)-ureido]-azepane-1-carboxylic acid methyl ester;
1-(1-Acetyl-piperidin-2-ylmethyl)-3-(5H-pyrrolo[2,3-b]pyrazin-2-yl)-urea;
2-{[3-(5H-Pyrrolo[2,3-b]pyrazin-2-yl)-ureido]-methyl}-piperidine-1-carboxylic acid methyl ester;
1-[2-(1-Acetyl-piperidin-2-yl)-ethyl]-3-(5H-pyrrolo[2,3-b]pyrazin-2-yl)-urea;
2-{2-[3-(5H-Pyrrolo[2,3-b]pyrazin-2-yl)-ureido]-ethyl}-piperidine-1-carboxylic acid methyl ester;
1-(1-Acetyl-piperidin-4-ylmethyl)-3-(5H-pyrrolo[2,3-b]pyrazin-2-yl)-urea;
1-(1-Methanesulfonyl-piperidin-4-ylmethyl)-3-(5H-pyrrolo[2,3-b]pyrazin-2-yl)-urea;
1-((1S,3S)-3-Methoxymethyl-cyclohexyl)-3-(5H-pyrrolo[2,3-b]pyrazin-2-yl)-urea;
1-(1-Acetyl-5-methyl-azepan-4-yl)-3-(5H-pyrrolo[2,3-b]pyrazin-2-yl)-urea;
1-[2-(1-Methanesulfonyl-piperidin-2-yl)-ethyl]-3-(5H-pyrrolo[2,3-b]pyrazin-2-yl)-urea;
1-[2-(1-Acetyl-piperidin-3-yl)-ethyl]-3-(5H-pyrrolo[2,3-b]pyrazin-2-yl)-urea;
4-{[3-(5H-Pyrrolo[2,3-b]pyrazin-2-yl)-ureido]-methyl}-piperidine-1-carboxylic acid methyl ester;
2-{[3-(5H-Pyrrolo[2,3-b]pyrazin-2-yl)-ureido]-methyl}-pyrrolidine-1-carboxylic acid methyl ester;
1-(5H-Pyrrolo[2,3-b]pyrazin-2-yl)-3-[(S)-1-(1-trifluoromethyl-cyclopropylmethanesulfonyl)-piperidin-3-yl]-urea;
1-Cyclohexyl-3-(7-isopropyl-5H-pyrrolo[2,3-b]pyrazin-2-yl)-urea;
1-[(S)-1-(3-Methyl-oxetan-3-ylmethanesulfonyl)-piperidin-3-yl]-3-(5H-pyrrolo[2,3-b]pyrazin-2-yl)-urea;
1-(1-Acetyl-piperidin-3-ylmethyl)-3-(5H-pyrrolo[2,3-b]pyrazin-2-yl)-urea;
1-(1-Methanesulfonyl-piperidin-3-ylmethyl)-3-(5H-pyrrolo[2,3-b]pyrazin-2-yl)-urea;
1-[2-(1-Acetyl-piperidin-4-yl)-ethyl]-3-(5H-pyrrolo[2,3-b]pyrazin-2-yl)-urea;
1-[2-(1-Acetyl-pyrrolidin-2-yl)-ethyl]-3-(5H-pyrrolo[2,3-b]pyrazin-2-yl)-urea;
1-[1-(Propane-1-sulfonyl)-pyrrolidin-2-ylmethyl]-3-(5H-pyrrolo[2,3-b]pyrazin-2-yl)-urea;
1-[2-(1-Methanesulfonyl-piperidin-4-yl)-ethyl]-3-(5H-pyrrolo[2,3-b]pyrazin-2-yl)-urea;
4-{2-[3-(5H-Pyrrolo[2,3-b]pyrazin-2-yl)-ureido]-ethyl}-piperidine-1-carboxylic acid methyl ester;
1-(1-Ethanesulfonyl-pyrrolidin-2-ylmethyl)-3-(5H-pyrrolo[2,3-b]pyrazin-2-yl)-urea;
1-[1-(Propane-2-sulfonyl)-pyrrolidin-2-ylmethyl]-3-(5H-pyrrolo[2,3-b]pyrazin-2-yl)-urea;
3-{[3-(5H-Pyrrolo[2,3-b]pyrazin-2-yl)-ureido]-methyl}-piperidine-1-carboxylic acid methyl ester;
1-(1-Methanesulfonyl-pyrrolidin-3-ylmethyl)-3-(5H-pyrrolo[2,3-b]pyrazin-2-yl)-urea;
1-(1-Acetyl-pyrrolidin-2-ylmethyl)-3-(5H-pyrrolo[2,3-b]pyrazin-2-yl)-urea;
1-[1-(2-Methyl-propane-1-sulfonyl)-pyrrolidin-2-ylmethyl]-3-(5H-pyrrolo[2,3-b]pyrazin-2-yl)-urea;
1-(5H-Pyrrolo[2,3-b]pyrazin-2-yl)-3-[1-(2,2,2-trifluoro-ethyl)-piperidin-2-ylmethyl]-urea;
1-(5H-Pyrrolo[2,3-b]pyrazin-2-yl)-3-[1-(2,2,2-trifluoro-ethyl)-piperidin-4-ylmethyl]-urea;
(1S,3S)-3-[3-(5H-Pyrrolo[2,3-b]pyrazin-2-yl)-ureido]-cyclohexanecarboxylic acid dimethylamide;
1-(5H-Pyrrolo[2,3-b]pyrazin-2-yl)-3-[1-(2,2,2-trifluoro-ethyl)-piperidin-3-ylmethyl]-urea;
1-(5H-Pyrrolo[2,3-b]pyrazin-2-yl)-3-{2-[1-(2,2,2-trifluoro-ethyl)-piperidin-3-yl]-ethyl}-urea;
3-{[3-(5H-Pyrrolo[2,3-b]pyrazin-2-yl)-ureido]-methyl}-pyrrolidine-1-carboxylic acid methyl ester;
1-(5H-Pyrrolo[2,3-b]pyrazin-2-yl)-3-{2-[1-(2,2,2-trifluoro-ethyl)-pyrrolidin-2-yl]-ethyl}-urea;
(1S,3S)-3-[3-(5H-Pyrrolo[2,3-b]pyrazin-2-yl)-ureido]-cyclopentanecarboxylic acid methylamide; and
(1S,3S)-3-[3-(5H-Pyrrolo[2,3-b]pyrazin-2-yl)-ureido]-cyclopentanecarboxylic acid ethylamide.

\* \* \* \* \*